(12) United States Patent
Biggadike et al.

(10) Patent No.: US 8,765,772 B2
(45) Date of Patent: *Jul. 1, 2014

(54) PURINE DERIVATIVES FOR USE IN THE TREATMENT OF ALLERGIC, INFLAMMATORY AND INFECTIOUS DISEASES

(75) Inventors: Keith Biggadike, Stevenage (GB); Diane Mary Coe, Stevenage (GB); Xiao Qing Lewell, Stevenage (GB); Charlotte Jane Mitchell, Stevenage (GB); Stephen Allan Smith, Stevenage (GB); Naimisha Trivedi, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 600 days.

This patent is subject to a terminal disclaimer.

(21) Appl. No.: 13/058,470

(22) PCT Filed: Aug. 7, 2009

(86) PCT No.: PCT/EP2009/060265
§ 371 (c)(1),
(2), (4) Date: Apr. 29, 2011

(87) PCT Pub. No.: WO2010/018133
PCT Pub. Date: Feb. 18, 2010

(65) Prior Publication Data
US 2011/0229500 A1    Sep. 22, 2011

Related U.S. Application Data

(60) Provisional application No. 61/087,777, filed on Aug. 11, 2008.

(51) Int. Cl.
*A61K 31/522*    (2006.01)
*C07D 473/34*    (2006.01)

(52) U.S. Cl.
USPC ..................................... 514/263.22; 544/276

(58) Field of Classification Search
USPC ..................................... 544/276; 514/263.22
See application file for complete search history.

(56) References Cited

U.S. PATENT DOCUMENTS

| 2001/0020030 A1 | 9/2001 | Stewart et al. |
| 2003/0236216 A1 | 12/2003 | Devos et al. |
| 2008/0269240 A1* | 10/2008 | Hashimoto et al. ...... 514/252.16 |

FOREIGN PATENT DOCUMENTS

| EP | 0773023 A1 | 5/1997 |
| EP | 1043021 A1 | 7/1999 |
| EP | 1939198 A1 | 7/2008 |
| WO | 9533750 A1 | 12/1995 |
| WO | 0043394 A1 | 7/2000 |
| WO | 0149688 A1 | 7/2001 |
| WO | 2005002520 A2 | 1/2005 |
| WO | 2005020892 A2 | 3/2005 |
| WO | 2005025583 A2 | 3/2005 |
| WO | 2006117670 A1 | 11/2006 |
| WO | 2007028129 A1 | 3/2007 |
| WO | 2007041863 A1 | 4/2007 |
| WO | 2007093901 A1 | 8/2007 |
| WO | 2007142755 A2 | 12/2007 |
| WO | 2008101867 A1 | 8/2008 |
| WO | 2008114008 A1 | 9/2008 |
| WO | 2010018130 A1 | 2/2010 |
| WO | 2010018131 A1 | 2/2010 |
| WO | 2010018132 A1 | 2/2010 |
| WO | 2010018134 A1 | 2/2010 |

OTHER PUBLICATIONS

WebMD. Allergic Health Center: Allergic Rhinitis-Prevention. Jun. 30, 2011 <http://www.webmd.com/allergies/tc/allergic-rhinitis-prevention>.*
WebMD. Asthma Health Center: Asthma Prevention. May 13, 2012. <http://www.webmd.com/asthma/guide/asthma-prevention>.*
Cryz, Stanley J. Immunotherapy and Vaccines. Ullmann's Encyclopedia of Industrial Chemistry. (2000) vol. 18. 647-722.*
Hirota et al; "Discovery of 8-Hydroxyadenines as a Novel Type of Interferon Inducer"; J. Med. Chem.; 2002; vol. 45, No. 25; pp. 5419-5422; American Chemical Society.

(Continued)

*Primary Examiner* — Golam M M Shameem
*Assistant Examiner* — Laura Daniel
(74) *Attorney, Agent, or Firm* — Kathryn L. Coulter

(57) ABSTRACT

The present invention relates to compounds of formula (I):

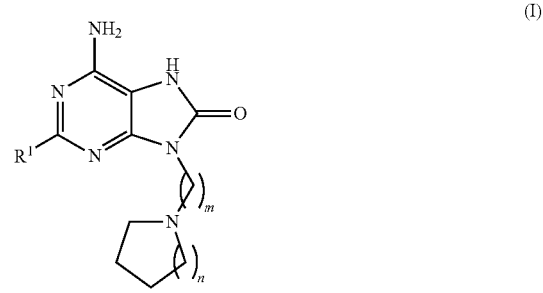

wherein $R^1$ is $C_{1-6}$alkylamino, $C_{1-6}$alkoxy, or $C_{3-7}$cycloalkyloxy; m is an integer having a value of 3 to 6; n is an integer having a value of 0 to 4; and salts thereof are inducers of human interferon. Compounds which induce human interferon may be useful in the treatment of various disorders, for example the treatment of allergic diseases and other inflammatory conditions for example allergic rhinitis and asthma, the treatment of infectious diseases and cancer, and may also be useful as vaccine adjuvants.

6 Claims, 1 Drawing Sheet

(56) References Cited

OTHER PUBLICATIONS

Isobe et al.; "Synthesis and Biological Evaluation of Novel 9-Substituted-8-hydroxyadenine Derivatives asPotent Interferon Inducers"; J. Med. Chem.; 2006; vol. 49, No. 6; pp. 2088-2095; American Chemical Society.

Kurimoto et al.; "Prodrugs of 9-Benzyl-8-hydroxy-2-(2-hydroxyethylthio)adenine: Potent Interferon Inducing Agents in Monkeys"; Chem. Pharm. Bull.; 2004; vol. 52, No. 4; pp. 466-469; Pharmaceutical Society of Japan.

* cited by examiner

Fig. 1: XRPD diffractogram of 6-amino-2-{[(1S)-1-methylbutyl]oxy}-9-[5-(1-piperidinyl)pentyl]-7,9-dihydro-8H-purin-8-one
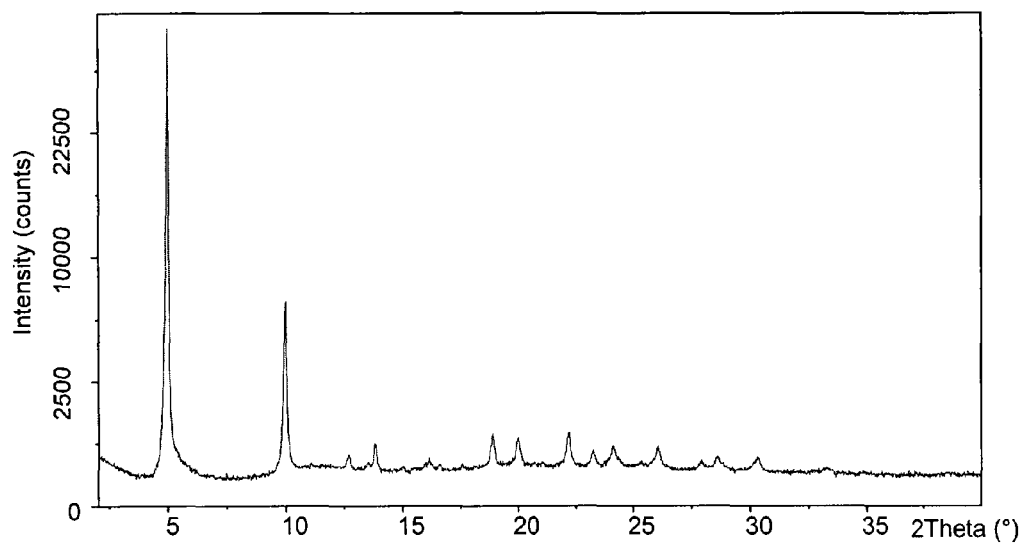
Fig. 2: DSC thermogram of 6-amino-2-{[(1S)-1-methylbutyl]oxy}-9-[5-(1-piperidinyl)pentyl]-7,9-dihydro-8H-purin-8-one
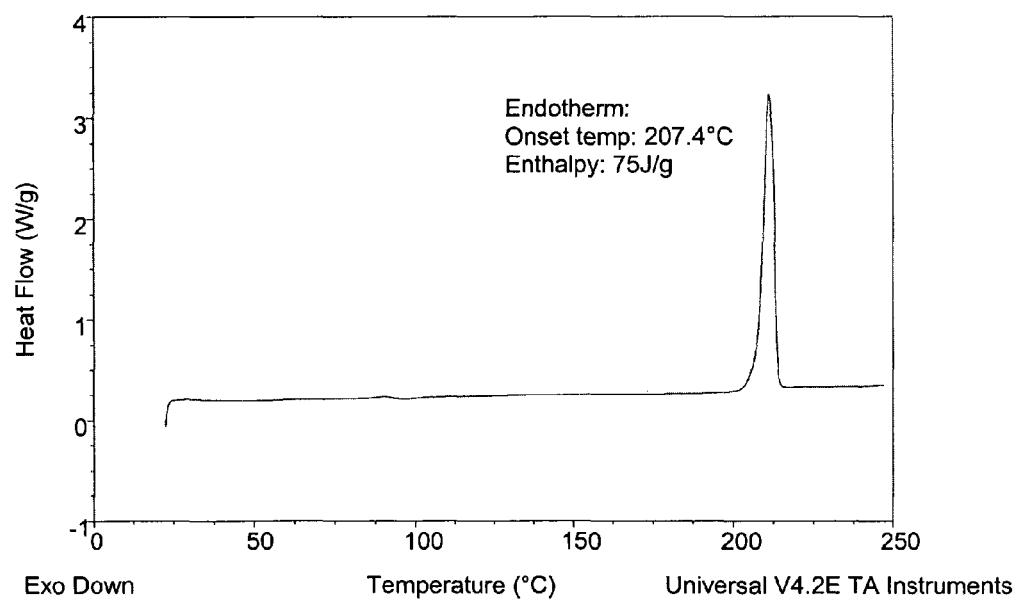

PURINE DERIVATIVES FOR USE IN THE TREATMENT OF ALLERGIC, INFLAMMATORY AND INFECTIOUS DISEASES

CROSS-REFERENCE TO RELATED APPLICATIONS

This application is filed pursuant to 35 U.S.C. §371 as a U.S. National Phase Application of International Patent Application Serial No. PCT/EP2009/060265filed Aug. 7, 2009, which claims priority from U.S. Provisional Application No. 61/087,777filed on Aug. 11, 2008.

BACKGROUND OF THE INVENTION

The present invention relates to compounds, processes for their preparation, compositions containing them, to their use in the treatment of various disorders in particular allergic diseases and other inflammatory conditions for example allergic rhinitis and asthma, infectious diseases, cancer, and as vaccine adjuvants.

Vertebrates are constantly threatened by the invasion of microorganisms and have evolved mechanisms of immune defence to eliminate infective pathogens. In mammals, this immune system comprises two branches; innate immunity and acquired immunity. The first line of host defence is the innate immune system, which is mediated by macrophages and dendritic cells. Acquired immunity involves the elimination of pathogens at the late stages of infection and also enables the generation of immunological memory. Acquired immunity is highly specific, due to the vast repertoire of lymphocytes with antigen-specific receptors that have undergone gene rearrangement.

The innate immune response was originally thought to be non-specific, but is now known to be able to discriminate between self and a variety of pathogens. The innate immune system recognises microbes via a limited number of germline-encoded Pattern-Recognition Receptors (PRRs) which have a number of important characteristics.

Toll-like receptors (TLRs) are a family of ten Pattern Recognition Receptors described in man. TLRs are expressed predominantly by innate immune cells where their role is to monitor the environment for signs of infection and, on activation, mobilise defence mechanisms aimed at the elimination of invading pathogens. The early innate immune-responses triggered by TLRs limit the spread of infection, while the pro-inflammatory cytokines and chemokines that they induce lead to recruitment and activation of antigen presenting cells, B cells, and T cells. The TLRs can modulate the nature of the adaptive immune-responses to give appropriate protection via dendritic cell-activation and cytokine release (Akira S. et al, *Nat. Immunol.*, 2001: 2, 675-680). The profile of the response seen from different TLR agonists depends on the cell type activated.

TLR7 is a member of the subgroup of TLRs (TLRs 3, 7, 8, and 9), localised in the endosomal compartment of cells which have become specialised to detect non-self nucleic acids. TLR7 plays a key role in anti-viral defence via the recognition of ssRNA (Diebold S. S. et al, *Science*, 2004: 303, 1529-1531; and Lund J. M. et al, *PNAS*, 2004: 101, 5598-5603). TLR7 has a restricted expression-profile in man and is expressed predominantly by B cells and plasmacytoid dendritic cells (pDC), and to a lesser extent by monocytes. Plasmacytoid DCs are a unique population of lymphoid-derived dendritic cells (0.2-0.8% of Peripheral Blood Mononuclear Cells (PBMCs)) which are the primary type I interferon-producing cells secreting high levels of interferon-alpha (IFNα) and interferon-beta (IFNβ) in response to viral infections (Liu Y-J, *Annu. Rev. Immunol.*, 2005: 23, 275-306).

Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis. In healthy individuals the immune-response to allergens is more balanced with a mixed Th2/Th1 and regulatory T cell response. TLR7 ligands have been shown to reduce Th2 cytokine and enhance Th1 cytokine release in vitro and to ameliorate Th2-type inflammatory responses in allergic lung models in vivo (Fili L. et al, *J. All. Clin. Immunol.*, 2006: 118, 511-517; Moisan J. et al, *Am. J. Physiol. Lung Cell Mol. Physiol.*, 2006: 290, L987-995; Tao et al, *Chin. Med. J.*, 2006: 119, 640-648). Thus TLR7 ligands have the potential to rebalance the immune-response seen in allergic individuals and lead to disease modification.

Central to the generation of an effective innate immune response in mammals are mechanisms which bring about the induction of interferons and other cytokines which act upon cells to induce a number of effects. These effects can include the activation of anti-infective gene expression, the activation of antigen presentation in cells to drive strong antigen-specific immunity and the promotion of phagocytosis in phagocytic cells.

Interferon was first described as a substance which could protect cells from viral infection (Isaacs & Lindemann, *J. Virus Interference. Proc. R. Soc. Lon. Ser. B. Biol. Sci.* 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

As a first-line therapy for hepatitis C virus (HCV) disease, interferon combinations can be highly effective at reducing viral load and in some subjects in eliminating viral replication. However, many patients fail to show a sustained viral response and in these patients viral load is not controlled. Additionally, therapy with injected interferon may be associated with a number of unwanted adverse effects which are shown to affect compliance (Dudley T, et al, Gut., 2006: 55(9), 1362-3).

Administration of a small molecule compound which could stimulate the innate immune response, including the activation of type I interferons and other cytokines, could become an important strategy for the treatment or prevention of human diseases including viral infections. This type of immunomodulatory strategy has the potential to identify compounds which may be useful not only in infectious diseases but also in cancer (Krieg. *Curr. Oncol. Rep.*, 2004: 6(2), 88-95), allergic diseases (Moisan J. et al, *Am. J. Physiol. Lung Cell Mol. Physiol.*, 2006: 290, L987-995), other inflammatory conditions such as irritable bowel disease (Rakoff-Nahoum S., *Cell.*, 2004, 23, 118(2): 229-41), and as vaccine adjuvants (Persing et al. *Trends Microbiol.* 2002: 10(10 Suppl), S32-7).

In animal models, imiquimod demonstrated adjuvant activities either topically (Adams S. et al, *J. Immunol.*, 2008, 181:776-84; Johnston D. et al, *Vaccine*, 2006, 24:1958-65), or systemically (Fransen F. et al, *Infect. Immun.*, 2007, 75:5939-46). Resiquimod and other related TLR7/8 agonists have also been shown to display adjuvant activity (Ma R. et al, *Biochem. Biophys. Res. Commun.*, 2007, 361:537-42; Wille-Reece U. et al, *Proc. Natl. Acad. Sci. USA*, 2005, 102:15190-4; Wille-Reece U. et al, US2006045885 A1).

Mechanisms which lead to induction of type I interferons are only partly understood. One mechanism which can lead to the induction of interferon in many cell types is the recognition of double-stranded viral RNA by the RNA helicases RIG-I and MDA5. This mechanism is thought to be the primary mechanism by which interferons are induced by Sendai virus infection of cells.

Further mechanisms for the induction of interferons are via TLR-dependent signalling events. In man, plasmacytoid dendritic cells (pDCs) are professional interferon-producing cells, able to make large amounts of interferons in response to, for example, viral infection. These pDCs are shown to preferentially express TLR7 and TLR9 and stimulation of these receptors with viral RNA or DNA respectively can induce expression of interferon alpha.

Oligonucleotide agonists of TLR7 and TLR9, and small molecule purine-based agonists of TLR7 have been described which can induce interferon alpha from these cell types in animals and in man (Takeda K. et al, *Annu. Rev. Immunol.*, 2003: 21, 335-76). TLR7 agonists include imidazoquinoline compounds such as imiquimod and resiquimod, oxoadenine analogues and also nucleoside analogues such as loxoribine and 7-thia-8-oxoguanosine which have long been known to induce interferon alpha. International Patent Application publication number WO 2008/114008 (AstraZeneca AB/Dainippon Sumitomo Pharma Co. Ltd.) discloses 9-substituted-8-oxoadenine compounds as TLR7 modulators.

It remains unclear how small molecule purine-like compounds can induce type I interferons and other cytokines since the molecular targets of these known inducers have not been identified. However, an assay strategy has been developed to characterise small molecule inducers of human interferon IFNα (regardless of mechanism) which is based on stimulation of primary human donor cells with compounds, and is disclosed herein.

BRIEF DESCRIPTION OF THE INVENTION

Certain compounds of the invention have been shown to be inducers of human interferon and may possess an improved profile with respect to known inducers of human interferon, for example enhanced potency, and may show enhanced selectivity for IFNα with respect to TNFα. For example, certain compounds of the invention indicate greater than 1000-fold selectivity for IFNα induction over TNFα induction. Compounds which induce human interferon may be useful in the treatment of various disorders, for example the treatment of allergic diseases and other inflammatory conditions for example allergic rhinitis and asthma, the treatment of infectious diseases and cancer, and may also be useful as vaccine adjuvants.

Certain compounds of the invention are potent immunomodulators and accordingly, care should be exercised in their handling.

SUMMARY OF THE INVENTION

In a first aspect, there are provided compounds of formula (I):

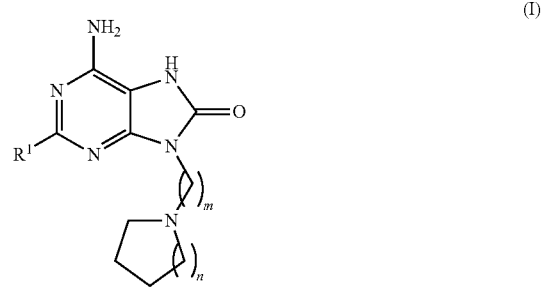

(I)

wherein;
$R^1$ is $C_{1-6}$alkylamino, $C_{1-6}$alkoxy, or $C_{3-7}$cycloalkyloxy;
m is an integer having a value of 3 to 6;
n is an integer having a value of 0 to 4;
with the proviso that, when m is 3 and n is 1, then $R^1$ is other than n-butyloxy; and salts thereof.

In a further embodiment, $R^1$ is $C_{1-6}$alkylamino or $C_{1-6}$alkoxy.
In a further embodiment, $R^1$ is n-butyloxy.
In a further embodiment, $R^1$ is n-butylamino.
In a further embodiment, $R^1$ is (1S)-1-methylbutyloxy.
In a further embodiment, $R^1$ is (1S)-1-methylpropyloxy.
In a further embodiment, $R^1$ is (1S)-1-methylpentyloxy.
In a further embodiment, $R^1$ is 1-methylethyloxy.
In a further embodiment, $R^1$ is cyclobutyloxy.
In a further embodiment, $R^1$ is cyclopentyloxy.
In a further embodiment, $R^1$ is cyclohexyloxy.
In a further embodiment, $R^1$ is (1R)-1-methylbutylamino.
In a further embodiment, $R^1$ is (1S)-1-methylbutylamino.
In a further embodiment, m is 3.
In a further embodiment, m is 4.
In a further embodiment, m is 5.
In a further embodiment, m is an integer having a value of 4 to 6.
In a further embodiment, m is 6.
In a further embodiment, n is 0.
In a further embodiment, n is 1.
In a further embodiment, n is 2.
In a further embodiment, n is 3.
In a further embodiment, n is 4.
In a further embodiment, n is an integer having a value of 2 to 4.

In a further aspect, there is provided a subset of compounds of formula (I) being compounds of formula (IA):

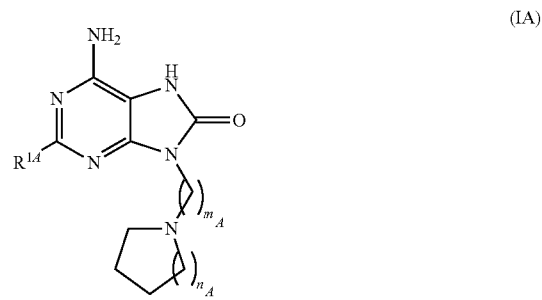

(IA)

wherein;
$R^{14}$ is $C_{1-6}$alkylamino or $C_{1-6}$alkoxy;
$m_A$ is an integer having a value of 3 to 6;
$n_A$ is an integer having a value of 0 to 4;
and salts thereof.

In a further embodiment, $R^{14}$ is n-butyloxy.
In a further embodiment, $R^{14}$ is n-butylamino.
In a further embodiment, $R^{14}$ is (1S)-1-methylbutyloxy.
In a further embodiment, $R^{14}$ is (1S)-1-methylpropyloxy.
In a further embodiment, $R^{14}$ is (1S)-1-methylpentyloxy.
In a further embodiment, $R^{14}$ is 1-methylethyloxy.
In a further embodiment, $R^{14}$ is (1R)-1-methylbutylamino.
In a further embodiment, $R^{14}$ is (1S)-1-methylbutylamino.
In a further embodiment, $m_A$ is 4.
In a further embodiment, $m_A$ is 5.
In a further embodiment, $m_A$ is 6.
In a further embodiment, $n_A$ is 0.
In a further embodiment, $n_A$ is 1.
In a further embodiment, $n_A$ is 2.
In a further embodiment, $n_A$ is 3.
In a further embodiment, $n_A$ is 4.

In a further aspect, there are provided compounds of formula (IA) and salts thereof as hereinbefore defined, wherein m is an integer having a value of 4 to 6.

In a further aspect, there are provided compounds of formula (IA) and salts thereof as hereinbefore defined, with the proviso that 6-amino-2-(butyloxy)-9-[3-(1-pyrrolidinyl)propyl]-7,9-dihydro-8H-purin-8-one is excluded.

In a further aspect, there are provided compounds of formula (I) and salts thereof with the proviso that 6-amino-2-{[(1S)-1-methylbutyl]oxy}-9-[5-(1-piperidinyl)pentyl]-7,9-dihydro-8H-purin-8-one and salts thereof are excluded.

In a further aspect, there are provided compounds of formula (IA) and salts thereof as hereinbefore defined, wherein m is an integer having a value of 4 to 6 and 6-amino-2-{[(1S)-1-methylbutyl]oxy}-9-[5-(1-piperidinyl)pentyl]-7,9-dihydro-8H-purin-8-one and salts thereof are excluded.

In a further aspect, there are provided compounds of formula (IA) and salts thereof as hereinbefore defined, with the proviso that 6-amino-2-(butyloxy)-9-[3-(1-pyrrolidinyl)propyl]-7,9-dihydro-8H-purin-8-one, and 6-amino-2-{[(1S)-1-methylbutyl]oxy}-9-[5-(1-piperidinyl)pentyl]-7,9-dihydro-8H-purin-8-one and salts thereof are excluded.

Examples of compounds of formula (I) are provided in the following list, and form a further aspect of the invention:
6-amino-9-[3-(1-azetidinyl)propyl]-2-(butyloxy)-7,9-dihydro-8H-purin-8-one;
6-amino-2-(butyloxy)-9-[3-(1-pyrrolidinyl)propyl]-7,9-dihydro-8H-purin-8-one;
6-amino-2-(butyloxy)-9-[3-(hexahydro-1H-azepin-1-yl)propyl]-7,9-dihydro-8H-purin-8-one;
6-amino-9-[4-(1-azetidinyl)butyl]-2-(butyloxy)-7,9-dihydro-8H-purin-8-one;
6-amino-2-(butyloxy)-9-[4-(1-pyrrolidinyl)butyl]-7,9-dihydro-8H-purin-8-one;
6-amino-2-(butyloxy)-9-[4-(1-piperidinyl)butyl]-7,9-dihydro-8H-purin-8-one;
6-amino-2-(butyloxy)-9-[4-(hexahydro-1H-azepin-1-yl)butyl]-7,9-dihydro-8H-purin-8-one;
6-amino-9-[5-(1-azetidinyl)pentyl]-2-(butyloxy)-7,9-dihydro-8H-purin-8-one;
6-amino-2-(butyloxy)-9-[5-(1-pyrrolidinyl)pentyl]-7,9-dihydro-8H-purin-8-one;
6-amino-2-(butyloxy)-9-[5-(1-piperidinyl)pentyl]-7,9-dihydro-8H-purin-8-one;
6-amino-2-(butyloxy)-9-[5-(hexahydro-1H-azepin-1-yl)pentyl]-7,9-dihydro-8H-purin-8-one;
6-amino-2-(butyloxy)-9-[5-(hexahydro-1(2H)-azocinyl)pentyl]-7,9-dihydro-8H-purin-8-one;
6-amino-2-(butyloxy)-9-[6-(1-pyrrolidinyl)hexyl]-7,9-dihydro-8H-purin-8-one;
6-amino-2-(butyloxy)-9-[6-(1-piperidinyl)hexyl]-7,9-dihydro-8H-purin-8-one;
6-amino-2-(butyloxy)-9-[6-(hexahydro-1H-azepin-1-yl)hexyl]-7,9-dihydro-8H-purin-8-one;
6-amino-2-(butylamino)-9-[3-(1-piperidinyl)propyl]-7,9-dihydro-8H-purin-8-one;
6-amino-2-(butylamino)-9-[4-(1-piperidinyl)butyl]-7,9-dihydro-8H-purin-8-one;
6-amino-2-(butylamino)-9-[4-(hexahydro-1H-azepin-1-yl)butyl]-7,9-dihydro-8H-purin-8-one;
6-amino-2-(butylamino)-9-[5-(hexahydro-1H-azepin-1-yl)pentyl]-7,9-dihydro-8H-purin-8-one;
6-amino-2-{[(1S)-1-methylbutyl]oxy}-9-[4-(1-piperidinyl)butyl]-7,9-dihydro-8H-purin-8-one;
6-amino-9-[4-(hexahydro-1H-azepin-1-yl)butyl]-2-{[(1S)-1-methylbutyl]oxy}-7,9-dihydro-8H-purin-8-one;
6-amino-2-{[(1S)-1-methylbutyl]oxy}-9-[5-(1-piperidinyl)pentyl]-7,9-dihydro-8H-purin-8-one;
6-amino-9-[5-(hexahydro-1H-azepin-1-yl)pentyl]-2-{[(1S)-1-methylbutyl]oxy}-7,9-dihydro-8H-purin-8-one;
6-amino-2-{[(1S)-1-methylpropyl]oxy}-9-[4-(1-piperidinyl)butyl]-7,9-dihydro-8H-purin-8-one;
6-amino-2-{[(1S)-1-methylpentyl]oxy}-9-[4-(1-piperidinyl)butyl]-7,9-dihydro-8H-purin-8-one;
6-amino-2-[(1-methylethyl)oxy]-9-[5-(1-piperidinyl)pentyl]-7,9-dihydro-8H-purin-8-one;
6-amino-2-(cyclobutyloxy)-9-[4-(1-piperidinyl)butyl]-7,9-dihydro-8H-purin-8-one;
6-amino-2-(cyclopentyloxy)-9-[4-(1-piperidinyl)butyl]-7,9-dihydro-8H-purin-8-one;
6-amino-2-(cyclohexyloxy)-9-[4-(1-piperidinyl)butyl]-7,9-dihydro-8H-purin-8-one;
6-amino-2-{[(1R)-1-methylbutyl]amino}-9-[4-(1-piperidinyl)butyl]-7,9-dihydro-8H-purin-8-one;
6-amino-2-{[(1S)-1-methylbutyl]amino}-9-[4-(1-piperidinyl)butyl]-7,9-dihydro-8H-purin-8-one;
6-amino-2-{[(1S)-1-methylbutyl]oxy}-9-[3-(1-piperidinyl)propyl]-7,9-dihydro-8H-purin-8-one;
6-amino-2-{[(1S)-1-methylpropyl]oxy}-9-[5-(1-piperidinyl)pentyl]-7,9-dihydro-8H-purin-8-one, and;
6-amino-2-(butyloxy)-9-[3-(1-piperidinyl)propyl]-7,9-dihydro-8H-purin-8-one;
and salts thereof.

In a further embodiment, there is provided 6-amino-2-{[(1S)-1-methylbutyl]oxy}-9-[5-(1-piperidinyl)pentyl]-7,9-dihydro-8H-purin-8-one or a salt thereof.

In a further embodiment, there is provided 6-amino-2-{[(1S)-1-methylbutyl]oxy}-9-[5-(1-piperidinyl)pentyl]-7,9-dihydro-8H-purin-8-one or a pharmaceutically acceptable salt thereof.

In a further embodiment, there is provided 6-amino-2-{[(1S)-1-methylbutyl]oxy}-9-[5-(1-piperidinyl)pentyl]-7,9-dihydro-8H-purin-8-one as a free base.

There is thus provided as a further aspect of the invention a compound of formula (I), or a pharmaceutically acceptable salt thereof, for use in therapy.

There is also therefore provided 6-amino-2-{[(1S)-1-methylbutyl]oxy}-9-[5-(1-piperidinyl)pentyl]-7,9-dihydro-8H-purin-8-one, or a pharmaceutically acceptable salt thereof, for use in therapy.

There is also therefore provided 6-amino-2-{[(1S)-1-methylbutyl]oxy}-9-[5-(1-piperidinyl)pentyl]-7,9-dihydro-8H-purin-8-one, as a free base, for use in therapy.

It will be appreciated that, when a compound of formula (I) or a pharmaceutically acceptable salt thereof is used in therapy, it is used as an active therapeutic agent.

There is also therefore provided a compound of formula (I), or a pharmaceutically acceptable salt thereof, for use in the treatment of allergic diseases and other inflammatory conditions, infectious diseases, and cancer.

There is also therefore provided 6-amino-2-{[(1S)-1-methylbutyl]oxy}-9-[5-(1-piperidinyl)pentyl]-7,9-dihydro-8H-purin-8-one, or a pharmaceutically acceptable salt thereof, for use in the treatment of allergic diseases and other inflammatory conditions, infectious diseases, and cancer.

There is also therefore provided 6-amino-2-{[(1S)-1-methylbutyl]oxy}-9-[5-(1-piperidinyl)pentyl]-7,9-dihydro-8H-purin-8-one, as a free base, for use in the treatment of allergic diseases and other inflammatory conditions, infectious diseases, and cancer.

There is also therefore provided a compound of formula (I), or a pharmaceutically acceptable salt thereof, for use in the treatment of allergic rhinitis.

There is also therefore provided 6-amino-2-{[(1S)-1-methylbutyl]oxy}-9-[5-(1-piperidinyl)pentyl]-7,9-dihydro-8H-purin-8-one, or a pharmaceutically acceptable salt thereof, for use in the treatment of allergic rhinitis.

There is also therefore provided 6-amino-2-{[(1S)-1-methylbutyl]oxy}-9-[5-(1-piperidinyl)pentyl]-7,9-dihydro-8H-purin-8-one, as a free base, for use in the treatment of allergic rhinitis.

There is also therefore provided a compound of formula (I), or a pharmaceutically acceptable salt thereof, for use in the treatment of asthma.

There is also therefore provided 6-amino-2-{[(1S)-1-methylbutyl]oxy}-9-[5-(1-piperidinyl)pentyl]-7,9-dihydro-8H-purin-8-one, or a pharmaceutically acceptable salt thereof, for use in the treatment of asthma.

There is also therefore provided 6-amino-2-{[(1S)-1-methylbutyl]oxy}-9-[5-(1-piperidinyl)pentyl]-7,9-dihydro-8H-purin-8-one, as a free base, for use in the treatment of asthma.

There is also therefore provided a vaccine adjuvant comprising a compound of formula (I), or a pharmaceutically acceptable salt thereof.

There is further provided an immunogenic composition comprising an antigen or antigen composition and a compound of formula (I), or a pharmaceutically acceptable salt thereof.

There is further provided a vaccine composition comprising an antigen or antigen composition and a compound of formula (I), or a pharmaceutically acceptable salt thereof.

There is further provided a method of treating or preventing disease comprising the administration to a human subject suffering from or susceptible to disease, an immunogenic composition comprising an antigen or antigen composition and a compound of formula (I), or a pharmaceutically acceptable salt thereof.

There is further provided a method of treating or preventing disease comprising the administration to a human subject suffering from or susceptible to disease, a vaccine composition comprising an antigen or antigen composition and a compound of formula (I), or a pharmaceutically acceptable salt thereof.

There is further provided the use of a compound of formula (I), or a pharmaceutically acceptable salt thereof, for the manufacture of an immunogenic composition comprising an antigen or antigen composition, for the treatment or prevention of disease.

There is further provided the use of a compound of formula (I), or a pharmaceutically acceptable salt thereof, for the manufacture of a vaccine composition comprising an antigen or antigen composition, for the treatment or prevention of disease.

There is further provided the use of a compound of formula (I), or a pharmaceutically acceptable salt thereof, for the manufacture of a medicament for the treatment of allergic diseases and other inflammatory conditions, infectious diseases, and cancer.

There is further provided the use of 6-amino-2-{[(1S)-1-methylbutyl]oxy}-9-[5-(1-piperidinyl)pentyl]-7,9-dihydro-8H-purin-8-one, or a pharmaceutically acceptable salt thereof, for the manufacture of a medicament for the treatment of allergic diseases and other inflammatory conditions, infectious diseases, and cancer.

There is further provided the use of 6-amino-2-{[(1S)-1-methylbutyl]oxy}-9-[5-(1-piperidinyl)pentyl]-7,9-dihydro-8H-purin-8-one, as a free base, for the manufacture of a medicament for the treatment of allergic diseases and other inflammatory conditions, infectious diseases, and cancer.

There is further provided the use of a compound of formula (I), or a pharmaceutically acceptable salt thereof, for the manufacture of a medicament for the treatment of allergic rhinitis.

There is further provided the use of 6-amino-2-{[(1S)-1-methylbutyl]oxy}-9-[5-(1-piperidinyl)pentyl]-7,9-dihydro-8H-purin-8-one, or a pharmaceutically acceptable salt thereof, for the manufacture of a medicament for the treatment of allergic rhinitis.

There is further provided the use of 6-amino-2-{[(1S)-1-methylbutyl]oxy}-9-[5-(1-piperidinyl)pentyl]-7,9-dihydro-8H-purin-8-one, as a free base, for the manufacture of a medicament for the treatment of allergic rhinitis.

There is further provided the use of a compound of formula (I), or a pharmaceutically acceptable salt thereof, for the manufacture of a medicament for the treatment of asthma.

There is further provided the use of 6-amino-2-{[(1S)-1-methylbutyl]oxy}-9-[5-(1-piperidinyl)pentyl]-7,9-dihydro-8H-purin-8-one, or a pharmaceutically acceptable salt thereof, for the manufacture of a medicament for the treatment of asthma.

There is further provided the use of 6-amino-2-{[(1S)-1-methylbutyl]oxy}-9-[5-(1-piperidinyl)pentyl]-7,9-dihydro-8H-purin-8-one, as a free base, for the manufacture of a medicament for the treatment of asthma.

There is further provided a method of treatment of allergic diseases and other inflammatory conditions, infectious diseases, and cancer, which method comprises administering to a human subject in need thereof, a therapeutically effective amount of a compound of formula (I), or a pharmaceutically acceptable salt thereof.

There is further provided a method of treatment of allergic diseases and other inflammatory conditions, infectious diseases, and cancer, which method comprises administering to a human subject in need thereof, a therapeutically effective amount of 6-amino-2-{[(1S)-1-methylbutyl]oxy}-9-[5-(1-piperidinyl)pentyl]-7,9-dihydro-8H-purin-8-one, or a pharmaceutically acceptable salt thereof.

There is further provided a method of treatment of allergic diseases and other inflammatory conditions, infectious diseases, and cancer, which method comprises administering to a human subject in need thereof, a therapeutically effective amount of 6-amino-2-{[(1S)-1-methylbutyl]oxy}-9-[5-(1-piperidinyl)pentyl]-7,9-dihydro-8H-purin-8-one as a free base.

There is further provided a method of treatment of allergic rhinitis, which method comprises administering to a human subject in need thereof, a therapeutically effective amount of a compound of formula (I), or a pharmaceutically acceptable salt thereof.

There is further provided a method of treatment of allergic rhinitis, which method comprises administering to a human subject in need thereof, a therapeutically effective amount of 6-amino-2-{[(1S)-1-methylbutyl]oxy}-9-[5-(1-piperidinyl)pentyl]-7,9-dihydro-8H-purin-8-one, or a pharmaceutically acceptable salt thereof.

There is further provided a method of treatment of allergic rhinitis, which method comprises administering to a human subject in need thereof, a therapeutically effective amount of 6-amino-2-{[(1S)-1-methylbutyl]oxy}-9-[5-(1-piperidinyl)pentyl]-7,9-dihydro-8H-purin-8-one as a free base.

There is further provided a method of treatment of asthma, which method comprises administering to a human subject in need thereof, a therapeutically effective amount of a compound of formula (I), or a pharmaceutically acceptable salt thereof.

There is further provided a method of treatment of asthma, which method comprises administering to a human subject in need thereof, a therapeutically effective amount of 6-amino-2-{[(1S)-1-methylbutyl]oxy}-9-[5-(1-piperidinyl)pentyl]-7,9-dihydro-8H-purin-8-one, or a pharmaceutically acceptable salt thereof.

There is further provided a method of treatment of asthma, which method comprises administering to a human subject in need thereof, a therapeutically effective amount of 6-amino-2-{[(1S)-1-methylbutyl]oxy}-9-[5-(1-piperidinyl)pentyl]-7,9-dihydro-8H-purin-8-one as a free base.

The invention provides in a further aspect, a combination comprising a compound of formula (I), or a pharmaceutically acceptable salt thereof, together with at least one other therapeutically-active agent.

The invention provides in a further aspect, a combination comprising 6-amino-2-{[(1S)-1-methylbutyl]oxy}-9-[5-(1-piperidinyl)pentyl]-7,9-dihydro-8H-purin-8-one, or a pharmaceutically acceptable salt thereof, together with at least one other therapeutically-active agent.

The invention provides in a further aspect, a combination comprising 6-amino-2-{[(1S)-1-methylbutyl]oxy}-9-[5-(1-piperidinyl)pentyl]-7,9-dihydro-8H-purin-8-one, as a free base, together with at least one other therapeutically-active agent.

There is further provided a pharmaceutical composition comprising a compound of formula (I), or a pharmaceutically acceptable salt thereof, and one or more pharmaceutically acceptable diluents or carriers.

There is further provided a pharmaceutical composition comprising 6-amino-2-{[(1S)-1-methylbutyl]oxy}-9-[5-(1-piperidinyl)pentyl]-7,9-dihydro-8H-purin-8-one, or a pharmaceutically acceptable salt thereof, and one or more pharmaceutically acceptable diluents or carriers.

There is further provided a pharmaceutical composition comprising 6-amino-2-{[(1S)-1-methylbutyl]oxy}-9-[5-(1-piperidinyl)pentyl]-7,9-dihydro-8H-purin-8-one, as a free base, and one or more pharmaceutically acceptable diluents or carriers.

There is also provided a process for preparing a pharmaceutical composition which comprises admixing a compound of formula (I), or a pharmaceutically acceptable salt thereof, with one or more pharmaceutically acceptable diluents or carriers.

There is also provided a process for preparing a pharmaceutical composition which comprises admixing 6-amino-2-{[(1S)-1-methylbutyl]oxy}-9-[5-(1-piperidinyl)pentyl]-7,9-dihydro-8H-purin-8-one, or a pharmaceutically acceptable salt thereof, with one or more pharmaceutically acceptable diluents or carriers.

There is also provided a process for preparing a pharmaceutical composition which comprises admixing 6-amino-2-{[(1S)-1-methylbutyl]oxy}-9-[5-(1-piperidinyl)pentyl]-7,9-dihydro-8H-purin-8-one, as a free base, with one or more pharmaceutically acceptable diluents or carriers.

The compounds of formula (I) and salts thereof may be prepared by the methodology described herein, which constitutes a further aspect of this invention.

Accordingly, there is provided a process for the preparation of a compound of formula (I), which process comprises the deprotection of a compound of formula (II):

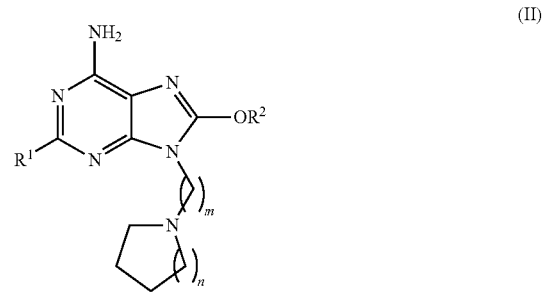

(II)

wherein $R^1$, m, and n are as hereinbefore defined for a compound of formula (I) and $R^2$ is $C_{1-6}$alkyl, and thereafter, if required, carrying out one or more of the following optional steps:
(i). removing any necessary protecting group;
(ii). preparing a salt of the compound so-formed.

The present invention covers all combinations of embodiments and aspects herein described.

BRIEF DESCRIPTION OF THE SEVERAL VIEWS OF THE DRAWINGS

FIG. 1 illustrates the XRPD diffractogram of 6-amino-2-{[(1S)-1-methylbutyl]oxy}-9-[5-(1-piperidinyhpentyl]-7,9-dihydro-8H-purin-8-one.

FIG. 2 illustrates the DSC thermogram of 6-amino-2-{[(1S)-1-methylbutyl]oxy}-9-[5-(1-piperidinyl)pentyl]-7,9-dihydro-8H-purin-8-one.

DETAILED DESCRIPTION OF THE INVENTION

The present invention is described in terms known and appreciated by those skilled in the art. For ease of reference certain terms hereinafter are defined. The fact that certain terms are defined, however, should not be considered as indicative that defined terms are used in a manner inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention. The following definitions are meant to clarify, but not limit, the terms defined.

References to 'alkyl' include references to both straight-chain and branched-chain aliphatic isomers of the corresponding alkyl containing up to six carbon atoms, for example up to four carbon atoms or up to two carbon atoms. Such references to 'alkyl' are also applicable when an alkyl group is part of another group, for example an alkylamino or alkoxy group. Examples of such alkyl groups and groups containing alkyl groups are $C_{1-6}$alkyl, $C_{1-6}$alkylamino, and $C_{1-6}$alkoxy.

References to 'cycloalkyl' refer to monocyclic alkyl groups containing between three and seven carbon atoms, for example four carbon atoms, or five carbon atoms, or six carbon atoms. Such references to 'cycloalkyl' are also applicable when a cycloalkyl group is part of another group, for example a cycloalkoxy group. Examples of such cycloalkyl groups are cyclobutyl, cyclopentyl, and cyclohexyl.

References to 'heterocycle' or 'heterocycly' refer to a monocyclic saturated heterocyclic aliphatic ring containing 3-7 carbon atoms and one heteroatom, which heteroatom is nitrogen. Such heterocyclic ring are azetidine or azetidinyl, pyrrolidine or pyrrolidinyl, piperidine or piperidinyl, hexahydroazepine or hexahydroazepinyl, and octahydroazocine or hexahydro-(2H)-azocinyl.

References to 'halogen' refer to iodine, bromine, chlorine or fluorine, typically bromine, chlorine, or fluorine. References to 'halo' refer to iodo, bromo, chloro or fluoro, typically bromo, chloro, or fluoro.

It is to be understood that references herein to compounds of the invention mean a compound of formula (I) as the free base, or as a salt, for example a pharmaceutically acceptable salt.

Salts of the compounds of formula (I) include pharmaceutically acceptable salts and salts which may not be pharmaceutically acceptable but may be useful in the preparation of compounds of formula and pharmaceutically acceptable salts thereof. Salts may be derived from certain inorganic or organic acids, or certain inorganic or organic bases.

The invention includes within its scope all possible stoichiometric and non-stoichiometric forms of the salts of the compounds of formula (I).

Examples of salts are pharmaceutically acceptable salts. Pharmaceutically acceptable salts include acid addition salts and base addition salts. For a review on suitable salts see Berge et al., *J. Pharm. Sci.*, 66:1-19 (1977).

Examples of pharmaceutically acceptable acid addition salts of a compound of formula (I) include hydrobromide, hydrochloride, sulphate, p-toluenesulphonate, methanesulphonate, naphthalenesulphonate, and phenylsulphonate salts.

Salts may be formed using techniques well-known in the art, for example by precipitation from solution followed by filtration, or by evaporation of the solvent.

Typically, a pharmaceutically acceptable acid addition salt can be formed by reaction of a compound of formula (I) with a suitable strong acid (such as hydrobromic, hydrochloric, sulphuric, p-toluenesulphonic, methanesulphonic or naphthalenesulphonic acids), optionally in a suitable solvent such as an organic solvent, to give the salt which is usually isolated for example by crystallisation and filtration.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methylpyrrolidinone may be used to form solvates. Methods for the identification of solvated include, but are not limited to, NMR and microanalysis. Solvates of the compounds of formula (I) are within the scope of the invention. As used herein, the term solvate encompasses solvates of both a free base compound as well as any salt thereof.

Certain of the compounds of the invention may contain chiral atoms and/or multiple bonds, and hence may exist in one or more stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

It will be appreciated from the foregoing that included within the scope of the invention are solvates, hydrates, isomers and polymorphic forms of the compounds of formula (I) and salts and solvates thereof.

Examples of disease states in which the compounds of formula (I) and pharmaceutically acceptable salts thereof have potentially beneficial effects include allergic diseases and other inflammatory conditions for example allergic rhinitis and asthma, infectious diseases, and cancer. The compounds of formula (I) and pharmaceutically acceptable salts thereof are also of potential use as vaccine adjuvants.

As modulators of the immune response the compounds of formula (I) and pharmaceutically acceptable salts thereof may also be useful, as stand-alone or in combination as an adjuvant, in the treatment and/or prevention of immune-mediated disorders, including but not limited to inflammatory or allergic diseases such as asthma, allergic rhinitis and rhinoconjuctivitis, food allergy, hypersensitivity lung diseases, eosinophilic pneumonitis, delayed-type hypersensitivity disorders, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

The compounds of formula (I) and pharmaceutically acceptable salts thereof may also be useful in the treatment and/or prevention of reactions against respiratory infections, including but not limited to airways viral exacerbations and tonsillitis. The compounds may also be useful in the treatment and/or prevention of autoimmune diseases including but not limited to rheumatoid arthritis, psoriatic arthritis, systemic lupus erythematosus, Sjöegrens disease, ankylosing spondylitis, scleroderma, dermatomyositis, diabetes, graft rejection, including graft-versus-host disease, inflammatory bowel diseases including, but not limited to, Crohn's disease and ulcerative colitis.

The compounds of formula (I) and pharmaceutically acceptable salts thereof may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

The compounds of formula (I) and pharmaceutically acceptable salts thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy may, depending on the condition, extend to prophylaxis as well as the treatment of established conditions.

As mentioned herein, compounds of formula (I) and pharmaceutically acceptable salts thereof may be useful as therapeutic agents.

The compounds of formula (I) and pharmaceutically acceptable salts thereof may be formulated for administration in any convenient way.

The compounds of formula (I) and pharmaceutically acceptable salts thereof may, for example, be formulated for oral, topical, inhaled, intranasal, buccal, parenteral (for example intravenous, subcutaneous, intradermal, or intramuscular) or rectal administration. In one aspect, the compounds of formula (I) and pharmaceutically acceptable salts thereof are formulated for oral administration. In a further aspect, the compounds of formula (I) and pharmaceutically acceptable salts thereof are formulated for topical administration, for example intranasal or inhaled administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or (a) pharmaceutically acceptable salt(s) thereof to be delivered to all areas of the nasal cavities (the target tissue) and further, may permit the compound(s) of formula (I) or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO2007/138084 (Glaxo Group Limited), for example as disclosed with reference to FIGS. 22-46 thereof, or as disclosed in United Kingdom patent application number GB0723418.0 (Glaxo Group Limited), for example as disclosed with reference to FIGS. 7-32 thereof. The pump may be actuated by an actuator as disclosed in FIGS. 1-6 of GB0723418.0.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (Astra-Zeneca), TWISTHALER™ (Schering) and CLICK-HALER™ (Innovate.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDI-HALER™ (Boehringer Ingelheim.)

Pressurised aerosol compositions suitable for inhalation can be either a suspension or a solution and may contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligolactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds of formula (I) and pharmaceutically acceptable salts thereof may, for example, be formulated for transdermal delivery by composition into patches or other devices (e.g. pressurised gas devices) which deliver the active component into the skin.

For buccal administration the compositions may take the form of tablets or lozenges formulated in the conventional manner.

The compounds of formula (I) and pharmaceutically acceptable salts thereof may also be formulated as suppositories, e.g. containing conventional suppository bases such as cocoa butter or other glycerides.

The compounds of formula (I) and pharmaceutically acceptable salts thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as anti-oxidants, buffers, anti-microbial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds of formula (I) and pharmaceutically acceptable salts thereof may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order. The amounts of the compound(s) of formula (I) or (a) pharmaceutically acceptable salt(s) thereof and the other pharmaceutically active agent(s) and the relative timings of administration will be selected in order to achieve the desired combined therapeutic effect. The administration of a combination of a compound of formula (I) or a pharmaceutically acceptable salt thereof with other treatment agents may be by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of formula (I) and pharmaceutically acceptable salts thereof may be used in combination with one or more agents useful in the prevention or treatment of viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCHSO3034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents. The compounds of formula (I) and pharmaceutically acceptable salts thereof may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or NSAIDs (non-steroidal anti-inflammatory agents) and similar agents.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, antihistamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

The compounds of formula (I) and pharmaceutically acceptable salts thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes in a further aspect a combination comprising a compound of formula (I), or a pharmaceutically acceptable salt thereof, together with at least one other therapeutically active agent.

The combinations referred to above may conveniently be presented for use in the form of a pharmaceutical composition and thus pharmaceutical compositions comprising a combination as defined above together with at least one pharmaceutically acceptable diluent or carrier thereof represent a further aspect of the invention.

A therapeutically effective amount of a compound of formula (I) or a pharmaceutically acceptable salt thereof will depend upon a number of factors. For example, the species, age, and weight of the recipient, the precise condition requiring treatment and its severity, the nature of the composition, and the route of administration are all factors to be considered. The therapeutically effective amount ultimately should be at the discretion of the attendant physician. Regardless, an effective amount of a compound of the present invention for the treatment of humans suffering from frailty, generally, should be in the range of 0.0001 to 100 mg/kg body weight of recipient per day. More usually the effective amount should be in the range of 0.001 to 10 mg/kg body weight per day. Thus, for a 70 kg adult one example of an actual amount per day would usually be from 7 to 700 mg. For intranasal and inhaled routes of administration, typical doses for a 70 kg adult should be in the range of 1 microgramme to 1 mg per day. This amount may be given in a single dose per day or in a number (such as two, three, four, five, or more) of sub-doses per day such that the total daily dose is the same. An effective amount of a pharmaceutically acceptable salt of a compound of formula (I) may be determined as a proportion of the effective amount of the compound of formula (I) or a pharmaceutically acceptable salt thereof per se. Similar dosages should be appropriate for treatment of the other conditions referred to herein.

Compounds of formula (I) and pharmaceutically acceptable salts thereof may also be administered at any appropriate frequency e.g. 1-7 times per week. The precise dosing regimen will of course depend on factors such as the therapeutic indication, the age and condition of the patient, and the particular route of administration chosen.

Pharmaceutical compositions may be presented in unit-dose forms containing a predetermined amount of active ingredient per unit dose. Such a unit may contain, as a non-limiting example, 0.5 mg to 1 g of a compound of formula (I) or a pharmaceutically acceptable salt thereof, depending on the condition being treated, the route of administration, and the age, weight, and condition of the patient. Preferred unit-dosage compositions are those containing a daily dose or sub-dose, as herein above recited, or an appropriate fraction thereof, of an active ingredient. Such pharmaceutical compositions may be prepared by any of the methods well-known in the pharmacy art.

There is thus further provided a pharmaceutical composition comprising a compound of formula (I), or a pharmaceutically acceptable salt thereof, and one or more pharmaceutically acceptable diluents or carriers.

There is also provided a process for preparing such a pharmaceutical composition which comprises admixing a compound of formula (I), or a pharmaceutically acceptable salt thereof, with one or more pharmaceutically acceptable diluents or carriers.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The compounds of formula (I) and salts thereof may be prepared by the methodology described hereinafter, constituting further aspects of this invention.

Accordingly, there is provided a process for the preparation of a compound of formula (I), which process comprises the deprotection of a compound of formula (II):

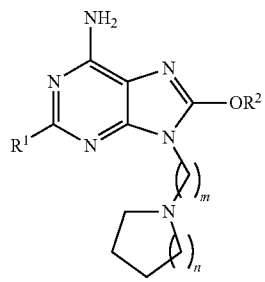

(II)

wherein $R^1$, m, and n are as hereinbefore defined for a compound of formula (I) and $R^2$ is $C_{1-6}$alkyl, and thereafter, if required, carrying out one or more of the following optional steps:
(i). removing any necessary protecting group;
(ii). preparing a salt of the compound so-formed.

For example, a compound of formula (II) is dissolved in a suitable solvent in the presence of a solution of a suitable acid, for example a solution of hydrogen chloride in 1,4-dioxane and stirred at a suitable temperature, for example ambient temperature for a suitable period of time, for example 12-24 hours. The solvent is removed under reduced pressure and the residue is dissolved in a suitable solvent, for example methanol, and loaded onto an ion-exchange cartridge, for example an aminopropyl SPE cartridge. The cartridge is eluted with a suitable solvent, for example methanol and the solvent removed to give a compound of formula (I).

A compound of formula (II) may be prepared by reaction of a compound of formula (III):

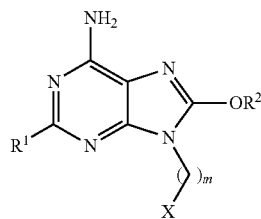

(III)

wherein $R^1$ and m are as hereinbefore defined for a compound of formula (I), $R^2$ is as hereinbefore defined for a compound of formula (II), and X is a leaving group, for example a halo group such as bromo or chloro, with a compound of formula (IV):

(IV)

wherein n is as defined for a compound of formula (I).

For example, a compound of formula (III), a compound of formula (IV) and a suitable base, for example N,N-diisopropylethylamine, are dissolved in a suitable solvent, for example DMF, and heated at a suitable temperature, for example 50-60° C. for a suitable period of time, for example 46-50 hours. If necessary additional compound of formula (IV) and base are added and the reaction mixture heated at a suitable temperature, for example 50-60° C. for a suitable period of time, for example 46-50 hours. The product is then extracted from the reaction using conventional means, for example by partitioning between a suitable organic solvent and water, followed by isolation of the organic phase and removal of the solvent, and purification if required.

A compound of formula (III) may be prepared by reaction of a compound of formula (V), for example a salt of a compound of formula (V) such as the trifluoroacetate salt:

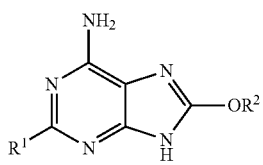

(V)

wherein $R^1$ is as hereinbefore defined for a compound of formula (I) and $R^2$ is as hereinbefore defined for a compound of formula (II), with a compound of formula (VI):

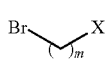

(VI)

wherein m is as hereinbefore defined for a compound of formula (I) and X is as hereinbefore defined for a compound of formula (III).

For example, the trifluoroacetate salt of a compound of formula (V) and a suitable base, for example potassium carbonate, are suspended in a suitable solvent, for example DMF, and heated to a suitable temperature, for example 50-60° C., under a suitable atmosphere, for example an atmosphere of nitrogen, for a suitable period of time, for example 20-120 minutes. The mixture is cooled to a suitable temperature, for example ambient temperature, and a compound of formula (VI) added and stirring continued at ambient temperature for a suitable period of time, for example 18-24 hours. The solvent is evaporated under reduced pressure and the residue partitioned between a suitable solvent, for example DCM, and water. The crude product is then isolated from the organic phase and purified by conventional techniques such as column chromatography.

Alternatively, a compound of formula (II) may be prepared by reaction of a compound of formula (V), for example a salt of a compound of formula (V) such as the trifluoroacetate salt, a compound of formula (VI) wherein X is bromo, and a compound of formula (IV) as a 'one-pot' process.

For example, the trifluoroacetate salt of a compound of formula (V) is dissolved in a suitable solvent, for example DMF and a suitable base, for example potassium carbonate, added. The reaction mixture is stirred at a suitable temperature, for example 45-60° C. under a suitable atmosphere, for example an atmosphere of nitrogen, for a suitable period of time, for example 1-2 hours and then cooled to a suitable temperature, for example ambient temperature. A compound of formula (VI) wherein X is bromo is then added and, after stirring for a suitable period of time, for example 40-60 minutes, a compound of formula (IV) and a suitable base, for example triethylamine, in a suitable solvent, for example DMF are added. The reaction mixture is then stirred for a suitable period of time, for example 12-24 hours. The solvent is removed and the residue is partitioned between a suitable organic solvent, for example dichloromethane, and water. The crude product of formula (II) is isolated by conventional means and purified by, for example, chromatography.

A salt of a compound of formula (V) may be prepared by deprotection of a compound of formula (VII):

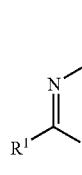

(VII)

wherein $R^1$ is as hereinbefore defined for a compound of formula (I), $R^2$ is as hereinbefore defined for a compound of formula (II), and P is a protecting group, for example a tetrahydro-2H-pyran-2-yl group, in the presence of a suitable acid, for example trifluoroacetic acid.

For example, a suitable acid, for example trifluoroacetic acid, is added to a solution of a compound of formula (VII) in a suitable solvent, for example methanol. The mixture is stirred at a suitable temperature, for example ambient temperature, for a suitable period of time, for example 48-72 hours. The reaction mixture is then concentrated under reduced pressure before being diluted with a suitable solvent, for example ethyl acetate. The resultant mixture is filtered and washed with a small volume of a suitable solvent, for example ethyl acetate until the filtrate is colourless. The residue is dried in air and then under reduced pressure to give the salt of a compound of formula (V). The filtrate may be concentrated and the concentrate diluted with a small volume of a suitable solvent, for example ethyl acetate, and then filtered and dried to yield a second crop of the salt of a compound of formula (V).

A salt of a compound of formula (V), for example the trifluoroacetate salt, may also be prepared by reaction of a compound of formula (IX):

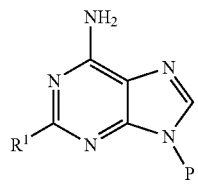

(IX)

wherein $R^1$ is as hereinbefore defined for a compound of formula (I) and P is as hereinbefore defined for a compound of formula (VII), with a suitable halogenating agent, for example N-bromosuccinimide, followed by reaction with an alkoxide anion, for example a methoxide anion, and then isolated in the presence of a suitable acid, for example trifluoroacetic acid.

For example, to a solution of crude compound of formula (IX) in a suitable dry solvent, for example dry chloroform, at a suitable temperature, for example ambient temperature, is added a suitable halogenating agent, for example N-bromosuccinimide, in portions over a suitable period of time, for example 5 minutes. The solution is stirred at a suitable temperature, for example ambient temperature, for a suitable period of time, for example 25-35 minutes. The reaction mixture is then washed with water and the organic phase dried by, for example, passing through a hydrophobic frit and concentrated under reduced pressure. The resultant solid is dissolved in a suitable dry solvent, for example dry methanol, and a suitable alkoxide, for example a solution of sodium methoxide in methanol, is added at a suitable temperature, for example ambient temperature, under an inert atmosphere, for example an atmosphere of nitrogen. The reaction mixture is heated at a suitable temperature, for example 60-70° C., with a condenser attached, for a suitable period of time, for example 12-18 hours. The reaction mixture is then cooled and concentrated under reduced pressure. The residue is then taken up in a suitable solvent, for example ethyl acetate, and poured into a suitable aqueous medium, for example saturated aqueous ammonium chloride solution. The organic layer is separated and washed further with water, dried, for example over magnesium sulphate, filtered and concentrated under reduced pressure. To a solution of this material in a suitable dry solvent, such as dry methanol, at a suitable temperature, for example ambient temperature, is added a suitable acid, for example trifluoroacetic acid. The reaction is stirred for a suitable period of time, for example 25-35 hours, and concentrated under reduced pressure to give a compound of formula (V).

A compound of formula (VII) may be prepared by reaction of a compound of formula (VIII):

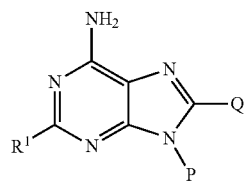

(VIII)

wherein $R^1$ is as hereinbefore defined for a compound of formula (I), P is as hereinbefore defined for a compound of formula (VII), and Q is a halogen atom, for example a bromine atom, with an alkoxide anion, for example methoxide anion.

For example, a solution of a compound of formula (VIII) in a suitable solvent, for example methanol, is heated to reflux with a solution of a suitable alkoxide, for example sodium methoxide, in a suitable solvent, for example methanol, for a suitable period of time, for example 4-5 hours. The reaction mixture is concentrated under reduced pressure and partitioned between a suitable organic solvent, for example ethyl acetate, and a suitable aqueous medium, for example saturated aqueous ammonium chloride solution. The organic phase is separated, washed, for example with brine, and dried by, for example passing through a hydrophobic frit. The solvent is then removed under reduced pressure to give a compound of formula (VII).

A compound of formula (VIII) may be prepared by reaction of a compound of formula (IX) with a suitable halogenating agent, such as N-bromosuccinimide.

For example, a compound of formula (IX) is dissolved in a suitable solvent, for example chloroform, and cooled to a suitable temperature, for example 0-0.5° C. To this solution is added a suitable halogenating agent, such as N-bromosuccinimide, while maintaining the temperature below about 3° C. The solution is stirred at a suitable temperature, for example 2-3° C. for a suitable period of time, for example 30-45 minutes then allowed to warm to a suitable temperature, for example ambient temperature, and stirred for a suitable period of time, for example 5-7 hours. The reaction mixture is then washed with water and the organic phase dried and separated from the aqueous phase using, for example, a hydrophobic frit. The organic solvent is then removed and the crude product purified by, for example, chromatography, to give a compound of formula (VIII).

A compound of formula (IX) wherein $R^1$ is $C_{1-6}$alkoxy may be prepared by reaction of a compound of formula (X):

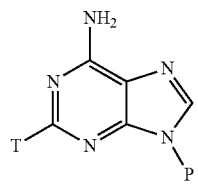

(X)

wherein P is as hereinbefore defined for a compound of formula (VII), and T is a suitable leaving group, for example a halogen atom, for example a chlorine atom, or a fluorine atom, with a solution of a compound of formula (XIII):

(XIII)

wherein $R^1$ is $C_{1-6}$alkoxy and M is a suitable alkali metal ligand such as sodium, prepared in a solvent of formula (IIIS):

(XIIIS)

wherein the $R^1$ group in the compound of formula (XIII) is the same as the $R^1$ group in the solvent of formula (XIIIS).

For example, a compound of formula (XIII) such as sodium t-butoxide, is added to a solvent of formula (XIIIS). The mixture is stirred until homogeneous, then a compound of formula (VII) is added. The reaction mixture is heated to a suitable temperature, for example 100° C., for a suitable period of time, for example 12-18 hours. The solvent is substantially removed under reduced pressure and partitioned between a suitable solvent, for example diethyl ether, and water. The organic phase is separated and the aqueous phase re-extracted with further solvent. The organic layers are then isolated, combined, dried using a suitable drying agent, for example anhydrous magnesium sulphate. The drying agent is removed by filtration and the solvent removed from the product under reduced pressure to give a compound of formula (IX) wherein $R^1$ is $C_{1-6}$alkoxy.

A compound of formula (IX) wherein $R^1$ is $C_{1-6}$alkylamino may be prepared by reaction of a compound of formula (X) with a compound of formula (XIV):

(XIV)

wherein $R^1$ is $C_{1-6}$alkylamino.

For example, a compound of formula (XIV) is added to a solution of a compound of formula (X) in a suitable dry solvent, for example dry ethylene glycol, at a suitable temperature, for example ambient temperature, under a suitable inert atmosphere, for example an atmosphere of nitrogen. The reaction mixture is heated at a suitable temperature, for example 110-130° C., for a suitable period of time, for example 12-18 hours. The reaction is then cooled to a suitable temperature, for example ambient temperature, diluted with a suitable solvent, for example ethyl acetate, and washed with water. The organic layer is dried with a suitable drying agent, for example anhydrous magnesium sulphate, filtered and concentrated under reduced pressure to yield a compound of formula (IX) wherein $R^1$ is $C_{1-6}$alkylamino.

A compound of formula (X) may be prepared by reaction of a compound of formula (XI):

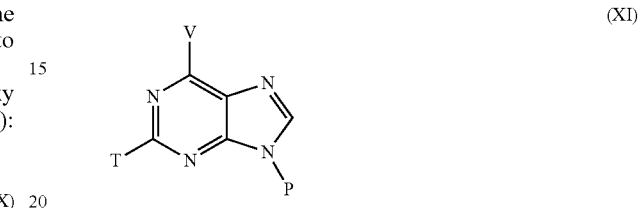

(XI)

wherein P is as hereinbefore defined for a compound of formula (VII), and T is as hereinbefore defined for a compound of formula (X), and V is a suitable leaving group, for example a halogen atom, for example a chlorine atom, with an alcoholic solution of ammonia, for example a solution of ammonia in iso-propyl alcohol.

For example, a compound of formula (XI) is heated with an alcoholic solution of ammonia, for example a 2M solution of ammonia in iso-propyl alcohol, at a suitable temperature, for example 50-60° C., for a suitable period of time, for example 5-6 hours. The reaction mixture is then left to stand at a suitable temperature, for example ambient temperature, for a suitable period of time, for example 12-18 hours. A further quantity of the alcoholic solution of ammonia, for example a 2M solution of ammonia in iso-propyl alcohol, is added to break up the resultant cake and the reaction mixture heated for a further period of time, for example 8-10 hours, until the reaction is complete. Water is added to the reaction mixture and the solid removed by filtration, washed with a suitable washing medium, for example a mixture of iso-propyl alcohol and water, and then dried, for example by air-drying under suction to give a first crop of a compound of formula (X). The filtrate is allowed to stand for a further period of time, for example 12-18 hours and the resultant second crop of a compound of formula (X) isolated by filtration and dried.

A compound of formula (X) may also be prepared by reaction of a compound of formula (XII):

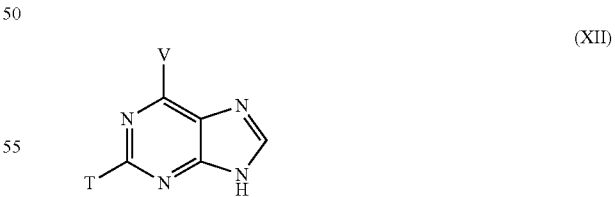

(XII)

wherein T is as hereinbefore defined for a compound of formula (X), and V is as hereinbefore defined for a compound of formula (XI), with a compound of formula (XV):

(XV)

wherein $P^U$ is a suitable precursor to the protecting group P, for example a 3,4-dihydro-2H-pyranyl group, followed by reaction with an alcoholic solution of ammonia, for example a solution of ammonia in iso-propyl alcohol.

For example, p-toluenesulfonic acid monohydrate is added to a solution of a compound of formula (XII) in a suitable dry solvent, for example dry ethyl acetate. The reaction mixture is heated to a suitable temperature, for example 50-60° C., and a compound of formula (XV) added. The reaction is stirred at a suitable temperature, for example 50-60° C., for a suitable period of time, for example 1-2 hours, and the solvent removed under reduced pressure. A suspension of the resultant solid in an alcoholic solution of ammonia, for example a 2M solution of ammonia in iso-propyl alcohol is heated under a suitable inert atmosphere, for example an atmosphere of nitrogen, at a suitable temperature, for example 60-70° C., for a suitable period of time, for example 4-5 hours with an attached condenser. The reaction mixture is poured into water and allowed to cool for a suitable period of time, for example 12-18 hours. The resultant precipitate is isolated by filtration and dried to give a compound of formula (X).

A compound of formula (X) may also be prepared by reaction of a compound of formula (XIA):

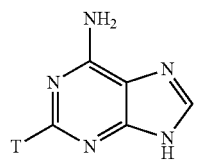

(XIA)

wherein T is a fluorine atom, with a suitable protecting agent, for example a silylating agent such as N,O-bis(trimethylsilyl)acetamide, followed by reaction of the protected compound of formula (XIA) with a compound of formula (XVE):

$$P^U\text{-E} \qquad (XVE)$$

wherein $P^U$ is a suitable precursor to the protecting group P, for example a 3,4-dihydro-2H-pyranyl group and E is an acyloxy group, for example an acetate group.

For example, a suitable protecting agent, for example N,O-bis(trimethylsilyl)acetamide is added to a stirred suspension of a compound of formula (XIA), for example 2-fluoro-1H-purin-6-amine, in a suitable anhydrous solvent, for example anhydrous acetonitrile, and the resulting mixture heated to reflux for a suitable period of time, for example 2-3 hours. The reaction mixture is then cooled to a suitable temperature, for example 0-5° C. A solution of a compound of formula (XVE), for example tetrahydropyranyl acetate, in a suitable anhydrous solvent, for example anhydrous acetonitrile, is then added slowly followed by the dropwise addition of a Lewis acid, for example trimethylsilyl trifluoromethanesulfonate. The reaction temperature is adjusted to a suitable temperature, for example 8-15° C., and stirring maintained for a further period of time, for example 1-2 hours. The mixture is then quenched by addition of 1M sodium carbonate. The organic layer is cooled to 0° C. with stirring. The precipitated solid is then collected by, for example, filtration and dried.

A compound of formula (XI) may be prepared by reaction of a compound of formula (XII) with a compound of formula (XV).

For example, to a compound of formula (XII) is added a suitable organic solvent, for example ethyl acetate, followed by p-toluenesulfonic acid. The mixture is heated to a suitable temperature, for example 50-60° C., and then 3,4-dihydro-2H-pyran added. The reaction mixture is then heated at a suitable temperature, for example 50-60° C. for a suitable period of time, for example 4-5 hours. The solvent is then removed from the reaction mixture under reduced pressure to yield a compound of formula (XI).

Abbreviations

The following list provides definitions of certain abbreviations as used herein. It will be appreciated that the list is not exhaustive, but the meaning of those abbreviations not herein below defined will be readily apparent to those skilled in the art.

DCM Dichloromethane
DMF N,N-Dimethylformamide
DMSO Dimethylsulphoxide
EtOAc Ethyl acetate
$Et_2O$ Diethyl ether
HCl Hydrochloric acid
HPLC High performance liquid chromatography
ISCO Companion Automated flash chromatography equipment with fraction analysis by UV absorption available from Presearch Limited, Basingstoke, Hants., RG24 8PZ, UK
MDAP HPLC Reverse phase HPLC on a $C_{18}$ column using a two-solvent gradient and analysis of the fractions by electrospray mass spectroscopy.
SPE Solid phase extraction
MeOH Methanol
mins minutes
Stripped Removal of solvent under reduced pressure
TFA Trifluoroacetic acid
iPr iso-Propyl
t-Bu tert-Butyl
Ms Mesyl
Ac Acetyl
n-Bu n-Butyl
Ph Phenyl
rt room temperature The synthetic processes hereinbefore described are summarised in Scheme 1.

Scheme 1

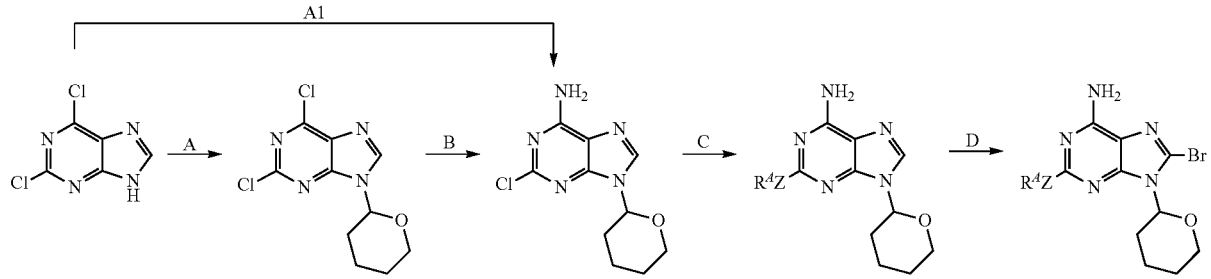

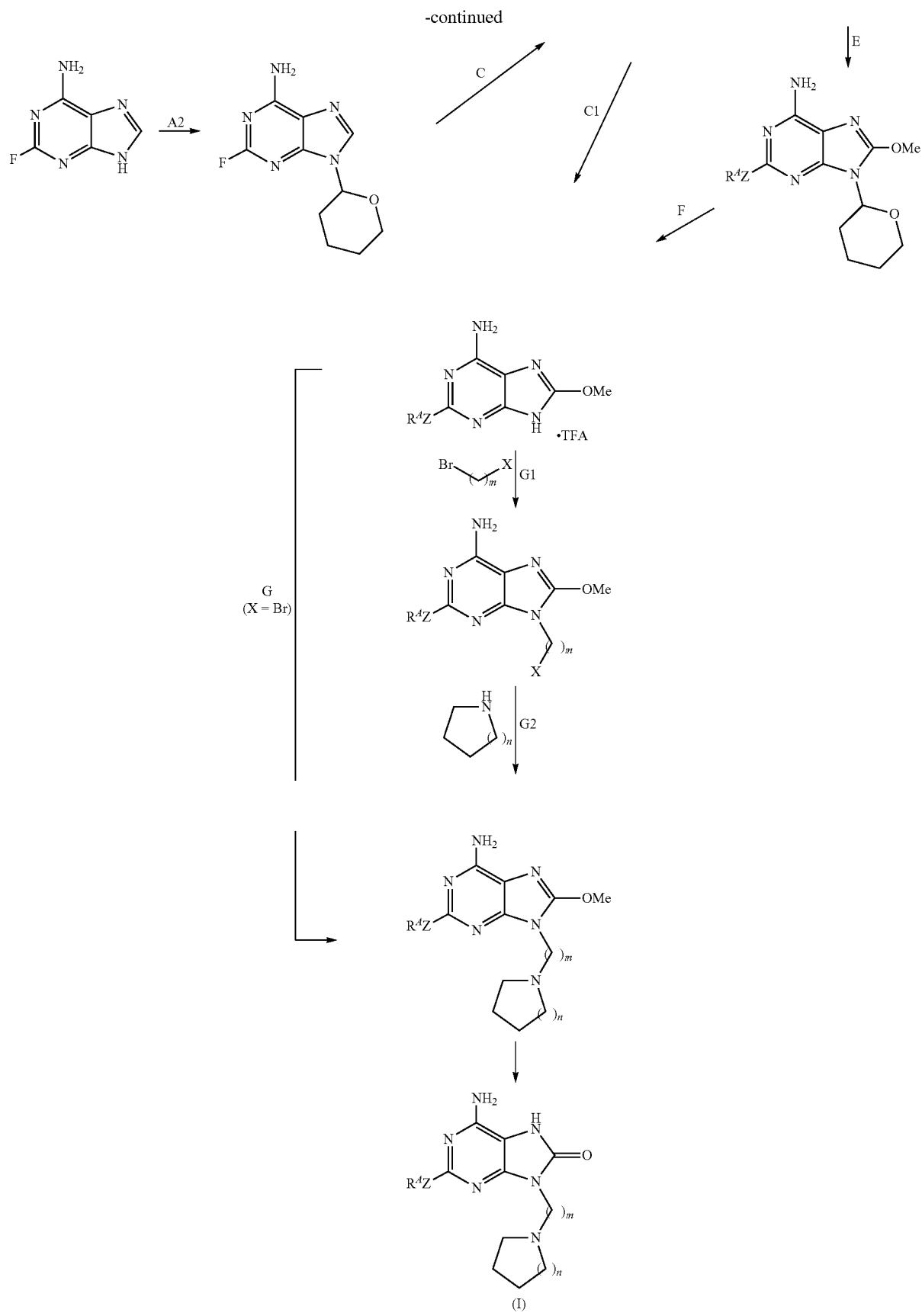

Typical reaction conditions for each of the synthetic steps of Scheme 1 are provided below:

A Dihydropyran/paratoluene sulphonic acid, e.g. 50° C. for 3-6 hours.

A1 Dihydropyran/paratoluene sulphonic acid, e.g. 50° C. for 1 hour, then ammonia/iPrOH, e.g. 60° C. for 4 hours, then add water and cool to ambient temperature over 12-18 hours.

A2 BSA in MeCN, reflux, cool to 0° C., then THP acetate in MeCN, warm to 10° C., then NaHCO$_3$ (aq.)

B Ammonia/iPrOH, e.g. 50° C. for 5 hours, then ambient temperature for 12-18 hours, then 50° C. for 9 hours.

C For X=NH, $R^4$=C$_{1-6}$alkyl: $R^4$NH$_2$/ethylene glycol e.g. 120° C. for 12-18 hours. For Z=O, $R^4$=C$_{1-6}$alkyl: $R^4$ONa/BuOH/dimethoxyethane e.g. 93-110° C. for 12-18 hours.

C1 NBS in CHCl$_3$ e.g. 0-5° C. for 30 minutes then ambient temperature for 0.5-1 hour, then e.g. NaOMe/methanol under N$_2$/60-70° C./12-18 hours, then TFA/MeOH e.g. ambient temperature for 18-65 hours.

D NBS in CHCl$_3$ e.g. 0-5° C. for 30 minutes then ambient temperature for 36-48 hours.

E NaOMe/MeOH e.g. reflux 4-6 hours.

F TFA/MeOH e.g. ambient temperature for 18-65 hours.

G K$_2$CO$_3$/DMF then 50° C. for 1-1.5 hours, then add (VI), stir 40 min, then add (IV)/Et$_3$N, then ambient temperature for 18 hours.

G1 K$_2$CO$_3$/DMF, then 50° C. under N$_2$ for 30 minutes, then ambient temperature, add (VI), stir for 20 hours.

G2 Solution in DMF with N,N-diisopropylethylamine, then 50° C. for 48 hours, then more (IV) added then further 50° C. for 48 hours.

H HCl/methanol, then ambient temperature for 18 hours.

Compounds of formulae (IV), (VI), (XIA), (XII), (XIII), (XIV), and (XV), are either known in the literature or are commercially available, for example from Sigma-Aldrich, UK, or may be prepared by analogy with known procedures, for example those disclosed in standard reference texts of synthetic methodology such as *J. March, Advanced Organic Chemistry, 6th Edition* (2007), *WileyBlackwell*, or *Comprehensive Organic Synthesis* (Trost B. M. and Fleming I., (Eds.), *Pergamon Press*, 1991), each incorporated herein by reference as it relates to such procedures.

Examples of other protecting groups that may be employed in the synthetic routes described herein and the means for their removal can be found in T. W. Greene *'Protective Groups in Organic Synthesis', 4th Edition, J. Wiley and Sons*, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulphate, or anhydrous sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

Aspects of the invention are illustrated by reference to, but are in no way limited by, the following Examples.

General Experimental Details

Compounds were named using ACD/Name PRO 6.02 chemical naming software from Advanced Chemistry Developments Inc., Toronto, Ontario, M5H2L3, Canada.

Experimental details of LCMS systems A-D as referred to herein are as follows:

System A

Column: 50 mm×2.1 mm ID, 1.7m Acquity UPLC BEH C$_{18}$
Flow Rate: 1 mL/min.
Temp.: 40° C.
UV detection range: 210 to 350 nm
Mass spectrum: Recorded on a mass spectrometer using alternative-scan positive and negative mode electrospray ionisation.
Solvents: A: 0.1% v/v formic acid in water
B: 0.1% v/v formic acid in acetonitrile
Gradient:

| Time (min.) | A % | B % |
|---|---|---|
| 0 | 97 | 3 |
| 0.1 | 97 | 3 |
| 1.4 | 0 | 100 |
| 1.9 | 0 | 100 |
| 2.0 | 97 | 3 |

System B

Column: 30 mm×4.6 mm ID, 3.5 μm Sunfire C$_{18}$ column
Flow Rate: 3 mL/min.
Temp: 30° C.
UV detection range: 210 to 350 nm
Mass spectrum: Recorded on a mass spectrometer using alternative-scan positive and negative mode electrospray ionisation
Solvents: A: 0.1% v/v solution of formic acid in water
B: 0.1% v/v solution of formic acid in acetonitrile
Gradient:

| Time (min.) | A % | B % |
|---|---|---|
| 0 | 97 | 3 |
| 0.1 | 97 | 3 |
| 4.2 | 0 | 100 |
| 4.8 | 0 | 100 |
| 4.9 | 97 | 3 |
| 5.0 | 97 | 3 |

System C

Column: 50 mm×2.1 mm ID, 1.7 μm Acquity HPLC BEH C$_{18}$
Flow Rate: 1 mL/min.
Temp: 40° C.
UV detection range: 210 to 350 nm
Mass spectrum: Recorded on a mass spectrometer using alternative-scan positive and negative mode electrospray ionisation Solvents: A: 10 mM ammonium bicarbonate in water adjusted to pH10 with ammonia solution B: acetonitrile Gradient:

| Time (min.) | A % | B % |
|---|---|---|
| 0 | 99 | 1 |
| 1.5 | 3 | 97 |
| 1.9 | 3 | 97 |
| 2.0 | 0 | 100 |

System D

Column: 50 mm×4.6 mm ID, 3.5 µn XBridge $C_{18}$ column

Flow Rate: 3 mL/min.

Temp: 30° C.

UV detection range: 210 to 350 nm

Mass spectrum: Recorded on a mass spectrometer using alternative-scan positive and negative mode electrospray ionisation Solvents: A: 10 mM ammonium bicarbonate in water adjusted to pH10 with ammonia solution B: acetonitrile Gradient:

| Time (min.) | A % | B % |
|---|---|---|
| 0 | 99 | 1 |
| 0.1 | 99 | 1 |
| 4.0 | 3 | 97 |
| 5.0 | 3 | 97 |

Chromatographic purification was typically performed using pre-packed silica gel cartridges. The Flashmaster II is an automated multi-user flash chromatography system, available from Argonaut Technologies Ltd, which utilises disposable, normal phase, Solid Phase Extraction (SPE) cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

Solvent removal using a stream of nitrogen was performed at 30-40° C. on a GreenHouse Blowdown system available from Radleys Discovery Technologies Saffron Walden, Essex, CB11 3AZ, UK $^1$H NMR spectra were recorded in either $CDCl_3$ or DMSO-$d_6$ on either a Bruker DPX 400 or Bruker Avance DRX or Varian Unity 400 spectrometer all working at 400 MHz. The internal standard used was either tetramethylsilane or the residual protonated solvent at 7.25 ppm for $CDCl_3$ or 2.50 ppm for DMSO-$d_6$.

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A

Method A was conducted on an XBridge $C_{18}$ column (typically 150 mm×19 mm i.d. 5 µm packing diameter) at ambient temperature. The solvents employed were:

A=10 mM aqueous ammonium bicarbonate adjusted to pH 10 with ammonia solution.

B=acetonitrile.

Method B

Method B was conducted on a Sunfire $C_{18}$ column (typically 150 mm×30 mm i.d. 5 µm packing diameter) at ambient temperature. The solvents employed were:

A=0.1% v/v solution of formic acid in water

B=0.1% v/v solution of formic acid in acetonitrile.

Method C

Method C was conducted on a Sunfire $C_{18}$ column (typically 150 mm×30 mm i.d. 5 µm packing diameter) at ambient temperature. The solvents employed were:

A=0.1% v/v solution of trifluoroacetic acid in water

B=0.1% v/v solution of trifluoroacetic acid in acetonitrile.

Method D

Method D was conducted on an Atlantis $C_{18}$ column (typically 100 mm×30 mm i.d. 5 µm packing diameter) at ambient temperature. The solvents employed were:

A=0.1% v/v solution of formic acid in water

B=0.1% v/v solution of formic acid in acetonitrile.

Method E

Method E was conducted on a Supelcosil ABZ+Plus column (typically 100 mm×21.2 mm i.d. 5 µm packing diameter) at ambient temperature. The solvents employed were:

A=0.1% v/v solution of formic acid in water

B=acetonitrile:water 95:5+0.05% formic acid

EXAMPLES

Intermediate 1: 2,6-Dichloro-9-(tetrahydro-2H-pyran-2-yl)-9H-purine

To 2,6-dichloropurine (25.0 g) (available from, for example, Aldrich, UK) was added ethyl acetate (260 ml), followed by p-toluenesulfonic acid (0.253 g). The mixture was heated to 50° C. and then 3,4-dihydro-2H-pyran (16.8 g) was added. The reaction mixture was then heated at 50° C. for 4 hours. The reaction mixture was evaporated in vacuo to give the title compound as a yellow solid (36.9 g).

1H NMR (CDCl$_3$): 8.35 (1H, s), 5.77 (1H, dd), 4.20 (1H, m), 3.79 (1H, m), 2.20-1.65 (6H, m).

Intermediate 2: 2-Chloro-9-(tetrahydro-2H-pyran-2-yl)-9H-purin-6-amine

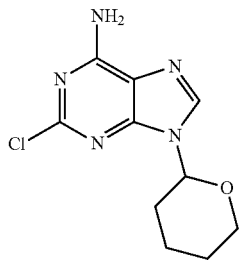 [SMILES: Nc1nc(Cl)nc2c1ncn2C1CCCCO1]

2,6-Dichloro-9-(tetrahydro-2H-pyran-2-yl)-9H-purine (36.9 g) was heated with 2M ammonia in isopropanol (250 ml) at 50° C. for 5 hours. After standing at ambient temperature overnight, a further quantity of 2M ammonia in isopropanol (100 ml) was added to break up the resultant cake and the reaction mixture was heated for a further 9 hours until the reaction was complete. To the reaction mixture was added water (70 ml) and the yellow solid filtered off. The solid was washed with isopropyl alcohol:water (5:1 (v/v), 60 ml) and then air-dried under suction to give a first crop. The filtrate was re-filtered after standing overnight to isolate precipitate and both solids were dried in vacuo. The first crop was pure with the second crop material showing a very minor impurity (isolated broad signal 3.5 ppm not seen in first crop) but was otherwise identical. Solid first crop (28.4 g), solid second crop (3.42 g).

1H NMR (CDCl$_3$): 8.01 (1H, s), 5.98 (2H, broad s), 5.70 (1H, dd), 4.16 (1H, m), 3.78 (1H, m), 2.15-1.60 (6H, overlapping m).

Intermediate 2 (Alternative Method): 2-Chloro-9-(tetrahydro-2H-pyran-2-yl)-9H-purin-6-amine

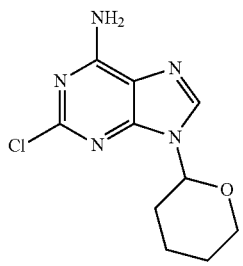 [SMILES: Nc1nc(Cl)nc2c1ncn2C1CCCCO1]

To a solution of 2,6-dichloropurine (25 g) (available from, for example, Aldrich, UK) in dry ethyl acetate (200 ml) was added p-toluenesulfonic acid monohydrate (235 mg). The reaction was heated to 50° C. and 3,4-dihydro-2H-pyran (18.1 ml) was added in one go. The reaction was allowed to stir at 50° C. for 1 hour and the solvent was removed under reduced pressure. This afforded a yellow solid. A suspension of this solid (~36 g) in 2.0M ammonia in isopropanol (460 ml) was heated under nitrogen at 60° C. for 4 hours with an attached condenser. The reaction was poured into water (50 ml) and left to cool overnight. The precipitate was filtered and dried on a rotary evaporator (60° C.) for 30 min. to afford the title compound as an off-white solid, 31 g (93%, 2 steps).

MS calcd for $(C_{10}H_{12}ClN_5O)^+$=254, 256
MS found (electrospray): $(M)^+$=254, 256 (3:1)
$^1$H NMR ((CD$_3$)$_2$SO): δ 8.43 (1H, s), 7.82 (2H, s), 5.55 (1H, dd), 4.00 (1H, m), 3.69 (1H, m), 2.21 (1H, m), 1.95 (2H, m), 1.74 (1H, m), 1.56 (2H, m).

Intermediate 3: 2-(Butyloxy)-9-(tetrahydro-2H-pyran-2-yl)-9H-burin-6-amine

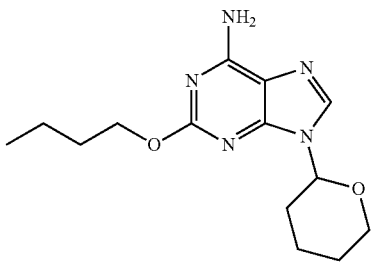 [SMILES: CCCCOc1nc(N)c2ncn(C3CCCCO3)c2n1]

To butan-1-ol (76 mL) was added portion wise sodium tert-butoxide (15.2 g) (Note: reaction mixture gets warm). The above was stirred until homogeneous (ca. 15 min) before 2-chloro-9-(tetrahydro-2H-pyran-2-yl)-9H-purin-6-amine (10.0 g) was then added to the resultant pale yellow solution. The reaction mixture was then heated to 100° C., overnight. The reaction mixture was stripped to remove as much butan-1-ol as possible before being partitioned between diethyl ether and water. The diethyl ether phase was separated and the aqueous re-extracted further with diethyl ether. Combined organic layers dried over magnesium sulphate (anhydrous). Magnesium sulphate was filtered off and filtrate stripped to give brown viscous oil which was azeotroped with toluene (3 times) and placed under high vacuum overnight, transferred to new flask with dichloromethane and stripped, placed under high vacuum to give the title compound as a brown glass (9.45 g).

1H NMR (CDCl$_3$): 7.85 (1H, s), 5.92 (2H, broad s), 5.64 (1H, d), 4.32 (2H, t), 4.14 (1H, m), 3.75 (1H, m), 2.10-1.95 (3H, overlapping m), 1.81-1.58 (5H, overlapping m), 1.50 (2H, m), 0.97 (3H, t).

Intermediate 4: 8-Bromo-2-(butyloxy)-9-(tetrahydro-2H-byran-2-yl)-9H-burin-6-amine

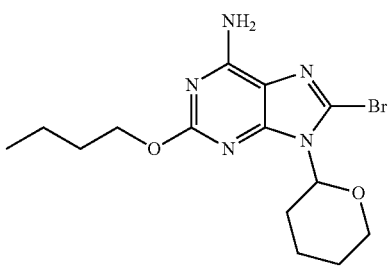 [SMILES: CCCCOc1nc(N)c2nc(Br)n(C3CCCCO3)c2n1]

2-(Butyloxy)-9-(tetrahydro-2H-pyran-2-yl)-9H-purin-6-amine (9.45 g) was dissolved in chloroform (50 ml) and cooled to 0° C. (ice-bath). To this solution was added portion wise N-bromosuccinimide (6.07 g) keeping the temperature below 3° C. This gave a dark green solution, stirred at 2.5° C.

for 30 mins. before allowing to warm to room temperature and then stirring for 6 hours. The reaction mixture was then washed with water (100 ml, twice). Organic phase was dried/separated using a hydrophobic frit and evaporated to give a dark brown gum which was purified by silica chromatography (120 g) (ISCO) using a gradient elution of 0-50% ethyl acetate: cyclohexane to afford the title compound as a pale yellow solid (8.37 g).

1H NMR (CDCl$_3$): 5.61 (1H, dd), 5.49 (2H, broad s), 4.32 (2H, m), 4.17 (1H, m), 3.71 (1H, m), 3.04 (1H, m), 2.11 (1H, broad d), 1.89-1.45 (6H, overlapping m), 1.50 (2H, m), 0.97 (3H, t).

Intermediate 5: 2-(Butyloxy)-8-(methyloxy)-9-(tetrahydro-2H-pyran-2-yl)-9H-purin-6-amine

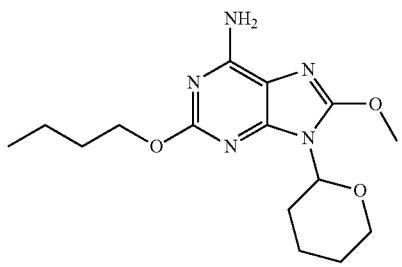 [SMILES: CCCCOc1nc(N)c2nc(OC)n(C3CCCCO3)c2n1]

8-Bromo-2-(butyloxy)-9-(tetrahydro-2H-pyran-2-yl)-9H-purin-6-amine (8.37 g) was heated to reflux with 25% sodium methoxide in methanol (14.4 ml) and methanol (65 ml) for 4.5 hours. The reaction mixture was concentrated under reduced pressure and partitioned between ethyl acetate and saturated ammonium chloride solution. Separated organic phase and repeated extraction into ethyl acetate. Combined organic phases and washed with brine (twice). The organic phase was passed through a hydrophobic frit after separating aqueous and was evaporated to give a light brown gum which was placed under high vacuum to give a foam (7.52 g) which collapsed to a gum (7.34 g) at ambient pressure and solidified overnight to give the title compound as a yellow amorphous solid.

MS calcd for $(C_{15}H_{23}N_5O_3)^+$=321
MS found (electrospray): $(M+H)^+$=322
1H NMR (CDCl$_3$): 5.50 (1H, dd), 5.17 (2H, broad s), 4.29 (2H, t), 4.12 (3H, s and 1H, m), 3.70 (1H, m), 2.77 (1H, m), 2.05 (1H, m), 1.82-1.63 (6H, overlapping m), 1.50 (2H, m), 0.97 (3H, t).

Intermediate 6: 2-(Butyloxy)-8-(methyloxy)-9H-purin-6-amine trifluoroacetate salt

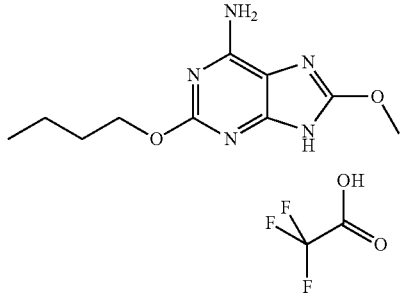 [SMILES: CCCCOc1nc(N)c2nc(OC)[nH]c2n1 ; O=C(O)C(F)(F)F]

To a solution of 2-(butyloxy)-8-(methyloxy)-9-(tetrahydro-2H-pyran-2-yl)-9H-purin-6-amine (7.34 g) in methanol (100 ml) was added trifluoroacetic acid (10 ml). The mixture was stirred at ambient temperature over the weekend to give a suspension. The reaction mixture was concentrated to a small volume (thick slurry) before being diluted with ethyl acetate (50 ml). The resultant slurry was filtered and washed with a small volume of ethyl acetate until the filtrate was colourless. The solid remaining was dried by air and then in vacuo to give the title compound as a white solid (6.20 g). The filtrate obtained previously was concentrated to give a slurry which was diluted with a small volume of ethyl acetate (10 ml) and then filtered and dried as above. This second crop was isolated as a white solid (0.276 g). Both crops were identical by NMR.

MS calcd for $(C_{10}H_{15}N_5O_2)^+$=237
MS found (electrospray): $(M+H)^+$=238
1H NMR (CD$_3$OD): 4.47 (2H, t), 4.15 (3H, s), 1.80 (2H, m), 1.50 (2H, m), 0.99 (3H, t) (exchangeable NH$_2$, NH and COOH protons not observed).

Intermediate 7: N$^2$-Butyl-9-(tetrahydro-2H-pyran-2-yl)-9H-purine-2,6-diamine

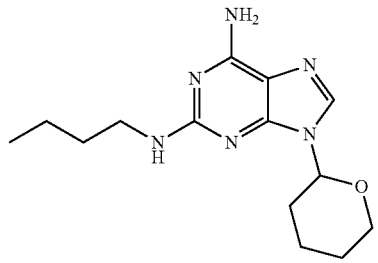 [SMILES: CCCCNc1nc(N)c2ncn(C3CCCCO3)c2n1]

To a solution of 2-chloro-9-(tetrahydro-2H-pyran-2-yl)-9H-purin-6-amine (10 g) in dry ethylene glycol (50 ml) at room temperature and under nitrogen was added n-butylamine (16 ml) in one go. The reaction was heated at 120° C. overnight. The reaction was cooled to room temperature, diluted with ethyl acetate (150 ml) and washed with water (2×50 ml). The organic layer was dried over MgSO$_4$, filtered and concentrated in vacuo. This afforded the title compound as a viscous green oil (10.2 g) that was used in the next step without further purification.

MS calcd for $(C_{14}H_{22}N_6O)^+$=290
MS found (electrospray): $(M+H)^+$=291
$^1$H NMR ((CD$_3$)$_2$SO): δ 7.8 (1H, s), 6.6 (2H, s), 6.2 (1H, t), 5.4 (1H, dd), 4.0 (1H, m), 3.6 (1H, m), 3.2 (2H, m), 2.2 (1H, m), 1.9 (1H, m), 1.8 (1H, m), 1.7 (1H, m), 1.5 (2H, m), 1.4 (2H, m), 1.3 (2H, m), 0.9 (3H, t).

Intermediate 8: N$^2$-Butyl-8-(methyloxy)-9H-purine-2,6-diamine trifluoroacetic acid salt

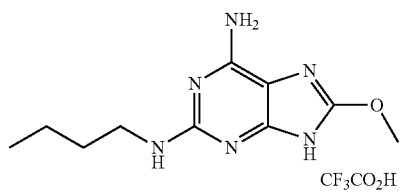

To a solution of crude N$^2$-butyl-9-(tetrahydro-2H-pyran-2-yl)-9H-purine-2,6-diamine (ca. 10.2 g) in dry chloroform (100 ml) at room temperature was added N-bromosuccinimide (6.3 g) in portions over 5 mins. The dark solution was allowed to stir at room temperature for 30 mins. The reaction mixture was washed with water (20 ml). The organic phase was passed through a hydrophobic frit and concentrated in vacuo. This afforded a beige solid which was dissolved in dry methanol (100 ml) and at room temperature under nitrogen was added sodium methoxide solution (25 wt. % in methanol, 24 ml) in one go. The reaction was heated at 65° C., with a condenser attached, overnight. The reaction was cooled and concentrated in vacuo. The resultant orange residue was taken up in ethyl acetate (150 ml) and poured into saturated aqueous ammonium chloride (50 ml). The organic layer was separated and washed further with water (50 ml). The organic layer was dried over $MgSO_4$, filtered and concentrated in vacuo. To this material in dry methanol (70 ml) at room temperature was added trifluoroacetic acid (7 ml) in one go. The reaction was stirred for 30 hours and concentrated in vacuo to yield a dark brown solid. This was taken up in diethyl ether (20 ml) and triturated. The solid was filtered to afford the title compound as a beige solid (3.3 g, 35%, 4 steps).

MS calcd for $(C_{10}H_{16}N_8O)^+$=236
MS found (electrospray): $(M+H)^+$=237
$^1$H NMR $((CD_3)_2SO)$: δ 13.3-12.3 (1H, br.m), 8.6-7.3 (2H, m), 4.05 (3H, s), 3.28 (2H, m), 1.52 (2H, m), 1.33 (2H, m), 0.89 (3H, t) (remaining exchangeable protons not clear).

Intermediate 9: 2-{[(1S)-1-Methylbutyl]oxy}-9-(tetrahydro-2H-pyran-2-yl)-9H-purin-6-amine

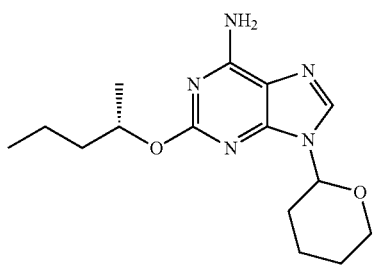

Method A

Sodium t-butoxide (48.5 g, 505 mmol) was added portionwise to (S)-2-pentanol (185 ml) (available from, for example, Julich Chiral Solutions, Germany) at room temperature stirred until homogeneous (Note: reaction is exothermic). 2-Chloro-9-(tetrahydro-2H-pyran-2-yl)-9H-purin-6-amine (32 g, 126 mmol) was added and the reaction mixture heated at 70° C. for 72 hours. The reaction was cooled to room temperature and partitioned between ethyl acetate (500 ml) and water (500 ml). The organic phase was washed with saturated sodium chloride solution (100 ml), dried ($MgSO_4$), filtered and evaporated. The residue was triturated with ether and the solid material filtered. The precipitate was re-washed with ether and the filtrates combined and evaporated. The crude material (ca. 30 g) was dissolved in DMSO:methanol (1:1) and purified by chromatography on a reverse phase ($C_{18}$) column (330 g) using a gradient of 25-65% acetonitrile (+0.1% TFA)-water(+0.1% TFA) over 8 column volumes, the fractions were immediately neutralised with saturated aqueous sodium carbonate solution. Appropriate fractions were combined and partitioned between dichloromethane and saturated aqueous sodium hydrogen carbonate. The organic phase was dried by passage through a hydrophobic frit, filtered and evaporated to give the title compound as a pale cream foam (14.97 g).

LCMS (System B): $t_{RET}$=2.21 min; $MH^+$306

Method B

Sodium t-butoxide (206 g, 2.144 mol) was added to (S)-2-pentanol (720 ml, 6.58 mol) (available from, for example, Julich Chiral Solutions, Germany) in a 2 L round bottomed flask. The mixture was stirred at 50° C. until all the sodium t-butoxide had dissolved. 2-Fluoro-9-(tetrahydro-2H-pyran-2-yl)-9H-purin-6-amine (130 g, 548 mmol) was then added in portions over 5 mins. After 3 hours LCMS analysis indicated complete consumption of the starting material and the mixture was poured into ice/water (3 L) and then extracted with methyl t-butyl ether. This resulted in emulsion formation and the mixture was filtered through Celite and the organic phase was separated. The aqueous layer was then treated with solid NaCl and then re-extracted with methyl t-butyl ether. The organic extracts were combined and washed with brine, dried over magnesium sulfate, filtered and then evaporated to yield the title compound as a pale brown gum (158.59 g).

LCMS (System D): $t_{RET}$=2.65 min; $MH^+$306

Intermediate 10: 8-Bromo-2-{[(1S)-1-methylbutyl]oxy}-9-(tetrahydro-2H-pyran-2-yl)-9H-purin-6-amine

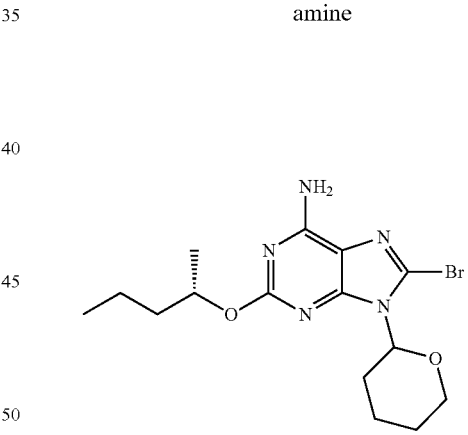

N-Bromosuccinimide (12.16 g, 68.3 mmol) was added portionwise over 5 mins. to a stirred solution of 2-{[(1S)-1-methylbutyl]oxy}-9-(tetrahydro-2H-pyran-2-yl)-9H-purin-6-amine (14.9 g, 48.8 mmol) in chloroform (80 ml) at <5° C. under an atmosphere of nitrogen. The reaction mixture was stirred at <5° C. for 5 hours then washed with saturated sodium hydrogen carbonate solution (80 ml) then water (80 ml). The foam was dissolved in DCM (50 ml) and washed with water (50 ml) then brine (50 ml). The combined aqueous phases were washed with DCM (50 ml). The combined organic layers were dried through a hydrophobic frit, and the solvent removed in vacuo to yield the title compound as an orange foam (18.5 g).

LCMS (System D): $t_{RET}$=3.06 min; $MH^+$384/386

Intermediate 11: 2-{[(1S)-1-Methylbutyl]oxy}-8-(methyloxy)-9-(tetrahydro-2H-pyran-2-yl)-9H-purin-6-amine

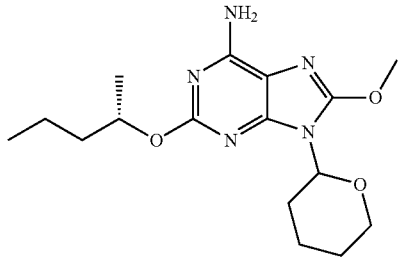 [SMILES: CCC[C@H](C)Oc1nc(N)c2nc(OC)n(C3CCCCO3)c2n1]

8-Bromo-2-{[(1S)-1-methylbutyl]oxy}-9-(tetrahydro-2H-pyran-2-yl)-9H-purin-6-amine (7.1 g, 18.48 mmol) was dissolved in anhydrous methanol (70 ml) and a solution of sodium methoxide (25%) in methanol (8 ml) was added dropwise under an atmosphere of nitrogen. The solution was heated to reflux at 90° C. for 4 hours under an atmosphere of nitrogen. Additional sodium methoxide in methanol (25% solution, 3 ml) was added and the reaction was stirred at 60° C. for a further 16 hours. An additional portion of sodium methoxide in methanol (25% solution, 5 ml) was added and the reaction was stirred at 90° C. for a further 7 hours. The solvent was removed on the rotary evaporator and the crude product was partitioned between EtOAc (75 ml) and saturated ammonium chloride solution (75 ml). The organic layer was washed with brine (75 ml). The solvent was removed on the rotary evaporator to yield the title compound as a pale orange foam (6 g).

LCMS (System C): $t_{RET}$=1.14 min; MH$^+$336, 337

Intermediate 12: 2-{[(1S)-1-Methylbutyl]oxy}-8-(methyloxy)-9H-burin-6-amine trifluoroacetate salt

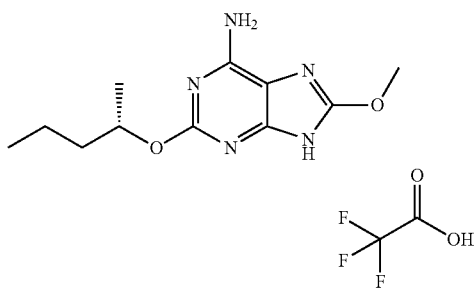 [SMILES: CCC[C@H](C)Oc1nc(N)c2nc(OC)[nH]c2n1 ; O=C(O)C(F)(F)F]

2-{[(1S)-1-Methylbutyl]oxy}-8-(methyloxy)-9-(tetrahydro-2H-pyran-2-yl)-9H-purin-6-amine (6 g, 17.89 mmol) was dissolved in methanol (50 ml). Trifluoroacetic acid (20.67 ml, 268 mmol) was added dropwise, and the mixture stirred at 20° C. for 72 hours under an atmosphere of nitrogen. The solvent was removed in vacuo, and the resulting solid was washed with ethyl acetate and filtered. The filtrate was stripped and the residue washed with ethyl acetate. The combined solid residues were dried in the vacuum oven for 2 hours to give the title compound as an off white solid (5.3 g).

LCMS (System C): $t_{RET}$=0.76 min; MH$^+$252, 253

Intermediate 13: 2-(Butyloxy)-9-(3-chloropropyl)-8-(methyloxy)-9H-purin-6-amine

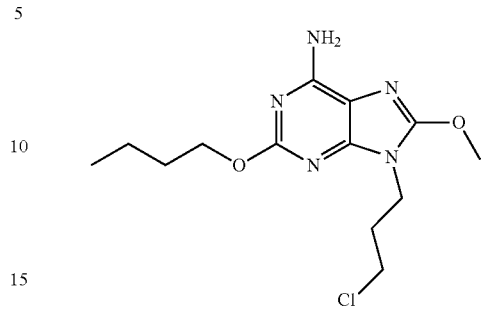

2-(Butyloxy)-8-(methyloxy)-9H-purin-6-amine trifluoroacetate (4.7 g, 13.38 mmol) and potassium carbonate (4.62 g, 33.4 mmol) in dry DMF (50 ml) were stirred and heated at 50° C., under nitrogen, for 75 mins. The mixture was allowed to cool to room temperature and then cooled to 0° C. and 1-bromo-3-chloropropane (2.106 g, 13.38 mmol) was added. The mixture was stirred at 0 to 10° C. for approximately 5 hours then allowed to warm to room temperature and stirred for approximately a further 40 hours when LCMS indicated approximately 70% of the desired product. The mixture was allowed to settle and the supernatant was pipetted off and the solvent evaporated on a rotary evaporator using a high vacuum pump at about 23° C. Chloroform and water was added to the combined residues which were stirred and the phases separated using a hydrophobic frit. The aqueous layer was re-extracted with further portions of chloroform and the combined chloroform extracts were evaporated under high vacuum at 23° C. to give a yellow solid (2.798 g). This crude material was combined with similar material obtained from two similar preparations (0.56 g and 0.995 g) and purified by flash column chromatography on silica using 2:1 ethyl acetate/chloroform as eluant to give the title compound as an off-white solid. (3.011 g).

LCMS (System D): $t_{RET}$=2.79 min; MH$^+$314, 316

Intermediate 14: 2-(Butyloxy)-9-(4-chlorobutyl)-8-(methyloxy)-9H-purin-6-amine

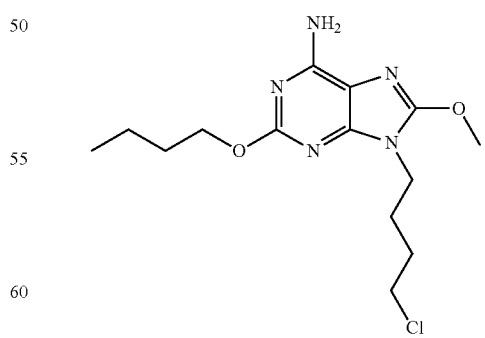

2-(Butyloxy)-8-(methyloxy)-9H-purin-6-amine trifluoroacetate (2 g, 5.69 mmol) and potassium carbonate (1.967 g, 14.23 mmol) were suspended in DMF (20 ml) and heated to 50° C., under nitrogen for 30 mins. The mixture was cooled to room temperature, 1-bromo-4-chlorobutane (0.656 ml, 5.69 mmol) was added and stirring continued at room temperature for 20 hours. The solvent was evaporated under reduced pressure and the residue was partitioned between DCM (40 ml) and water (40 ml). The layers were separated using a hydrophobic frit and the aqueous layer washed with DCM (10 ml). The combined organic extracts were concentrated in vacuo to give crude material that was purified by silica chromatography using the FlashMaster (70 g cartridge) eluting with a cyclohexane:ethyl acetate 0-100% gradient over 30 mins. The product-containing fractions were combined and evaporated to give the title compound as a white solid (1.4 g).

LCMS (System D): $t_{RET}$=2.92 min; MH$^+$=328, 330

Intermediate 15: 2-(Butyloxy)-9-(5-chloropentyl)-8-(methyloxy)-9H-purin-6-amine

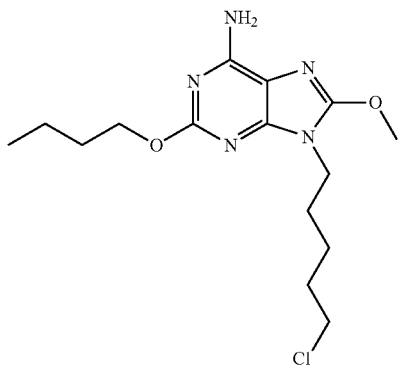 [SMILES: CCCCOc1nc(N)c2nc(OC)n(CCCCCCl)c2n1]

2-(Butyloxy)-8-(methyloxy)-9H-purin-6-amine trifluoroacetate (2 g, 5.69 mmol) and potassium carbonate (1.967 g, 14.23 mmol) were suspended in DMF (20 ml) and heated to 50° C., under nitrogen for 1 hour. The mixture was cooled to room temperature, 1-bromo-5-chloropentane (0.75 ml, 5.69 mmol) was added and stirring was continued at room temperature for 18 hours. The reaction mixture was partitioned between DCM (40 ml) and water (40 ml) and the layers were separated using a hydrophobic frit. The aqueous layer was extracted again with DCM (10 ml) and the combined organics were washed with saturated lithium chloride solution, separated (hydrophobic frit) and concentrated in vacuo to give the title compound as a yellow oil (1.946 g).

LCMS (System B): $t_{RET}$=2.58 min; MH$^+$=342, 344

Intermediate 16: 2-(Butyloxy)-9-(5-chlorohexyl)-8-(methyloxy)-9H-purin-6-amine

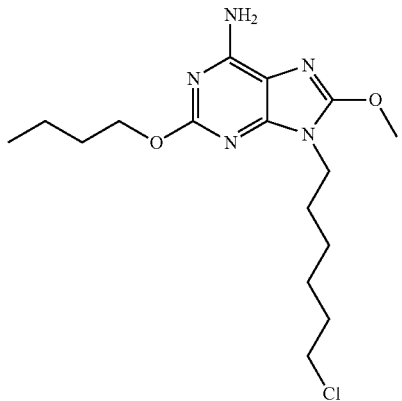 [SMILES: CCCCOc1nc(N)c2nc(OC)n(CCCCCCCl)c2n1]

To a solution of 2-(butyloxy)-8-(methyloxy)-9H-purin-6-amine trifluoroacetate salt (3 g, 8.54 mmol) in DMF (30 ml) was added potassium carbonate (2.95 g, 21.35 mmol) and the mixture stirred at 60° C. for 1 hour under an atmosphere of nitrogen. The mixture was then cooled to room temperature and 1-bromo-6-chlorohexane (1.27 ml, 8.54 mmol) was added and the reaction heated to 50° C. and stirred overnight under an atmosphere of nitrogen. The reaction mixture was diluted with water (ca. 50 ml) and extracted with ethyl acetate (2×70 ml). The combined organic extracts were dried (MgSO$_4$), filtered and the filtrate concentrated to give an orange oil (ca.3.5 g). This material was dissolved in dichloromethane and purified on a FlashmasterII (70 g aminopropyl cartridge) using a 0-100% ethyl acetate in cyclohexane gradient over 60 mins. The appropriate fractions were combined and evaporated in vacuo to give the title compound as a yellow oil which solidified to a pale yellow solid (1.2 g).

LCMS (System D): $t_{RET}$=3.59 min; MH$^+$=356, 358

Intermediate 17: N$^2$-Butyl-9-(3-chloropropyl)-8-(methyloxy)-9H-purine-2,6-diamine

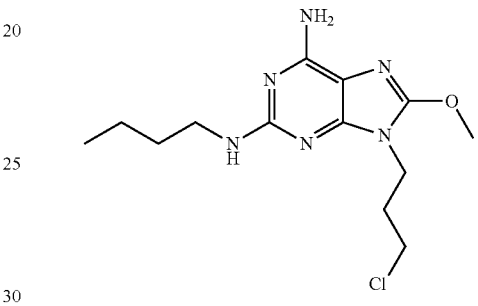

N$^2$-Butyl-8-(methyloxy)-9H-purine-2,6-diamine trifluoroacetate (701 mg, 2.001 mmol) and potassium carbonate (690 mg, 4.99 mmol) were suspended in DMF (10 ml) and the mixture heated at 50° C. under nitrogen for 2 hours. The mixture was allowed to cool and then 1-bromo-3-chloropropane (198 μl, 2.002 mmol) was added and the reaction mixture stirred at ambient temperature overnight. After 16 hours the reaction mixture was partitioned between water and DCM (25 ml of each). The aqueous phase was extracted with further DCM (2×20 ml). The combined DCM extracts were dried over magnesium sulphate and concentrated in vacuo to give the impure title compound as a pale yellow oil with some solid present (0.76 g) which was used without further purification.

LCMS (System D): $t_{RET}$=2.75 min; MH$^+$=313, 315

Intermediate 18: N$^2$-Butyl-9-(4-chlorobutyl)-8-(methyloxy)-9H-purine-2,6-diamine

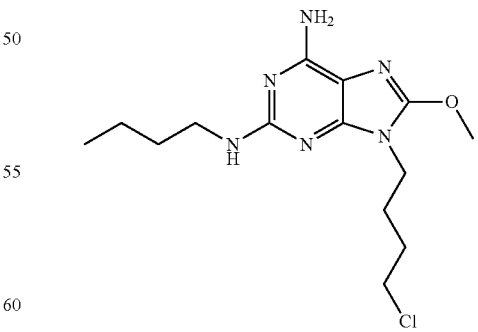

N$^2$-Butyl-8-(methyloxy)-9H-purine-2,6-diamine trifluoroacetate (5 g, 14.27 mmol) and potassium carbonate (4.93 g, 35.7 mmol) were suspended in DMF (40 ml) and heated to 50° C. under nitrogen for 30 mins. The mixture was cooled to room temperature, 1-bromo-4-chlorobutane (1.645 ml, 14.27 mmol) was added and stirring was continued at room temperature for 20 hours. The solvent was concentrated under vacuum and the residue was partitioned between DCM (100 ml) and water (100 ml). The layers were separated using a hydrophobic frit and the aqueous phase was re-extracted with DCM (100 ml). The combined organics extracts were concentrated in vacuo and the residue purified by chromatography using a FlashMaster apparatus (100 g silica cartridge) and using a DCM:methanol 0-25% gradient over 40 mins. The desired fractions were combined and concentrated under vacuum to give the impure title compound as a yellow oil (5.1 g).

LCMS (System D): $t_{RET}$=2.88 min; MH$^+$=327, 329

Intermediate 19: 9-(5-Chloropentv1)-2-{[(1S)-1-methylbutyl]oxy}-8-(methyloxy)-9H-purin-6-amine

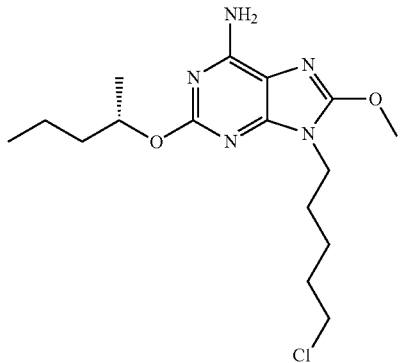 [SMILES: CCC[C@H](C)Oc1nc(N)c2nc(OC)n(CCCCCCl)c2n1]

2-{[(1S)-1-Methylbutyl]oxy}-8-(methyloxy)-9H-purin-6-amine trifluoroacetate (600 mg, 1.642 mmol) and potassium carbonate (567 mg, 4.11 mmol) were stirred at 60° C. in DMF (10 ml) for 1 hour under nitrogen. The reaction was cooled to room temperature when 1-bromo-5-chloropentane (0.216 ml, 1.642 mmol) and triethylamine (0.343 ml, 2.464 mmol) were added and the mixture stirred at 20° C. under nitrogen for 16 hours. The mixture was then diluted with water (10 ml) and brine (10 ml) and extracted with DCM (2×10 ml). The combined organic extracts were evaporated and the residue dissolved in DCM and purified by column chromatography using the Flashmaster II (70 g aminopropyl cartridge) with a 0-100% ethyl acetate in cyclohexane gradient over 40 mins. The appropriate fractions were combined and evaporated in vacuo to give the title compound as a yellow gum (430 mg).

LCMS (System D): $t_{RET}$=4.15 min; MH$^+$=356, 358

Intermediate 20: 9-[3-(1-Azetidinyl)propyl]-2-(butyloxy)-8-(methyloxy)-9H-purin-6-amine

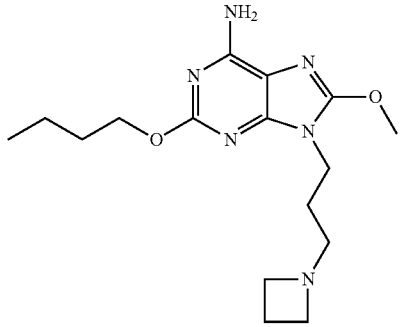 [SMILES: CCCCOc1nc(N)c2nc(OC)n(CCCN3CCC3)c2n1]

2-(Butyloxy)-8-(methyloxy)-1H-purin-6-amine trifluoroacetate (100 mg, 0.285 mmol) was dissolved in DMF (1 ml) and potassium carbonate (98 mg, 0.712 mmol) was added. The reaction mixture was stirred at 50° C. under nitrogen for 1 hour and then cooled to room temperature. 1,3-Dibromopropane (0.029 ml, 0.285 mmol) was added and after stirring for a further 40 mins. azetidine (0.038 ml, 0.569 mmol) and triethylamine (0.079 ml, 0.569 mmol) in DMF (1 ml) were added. The reaction mixture was then stirred for a further 18 hours. The solvent was removed and the residue was partitioned between dichloromethane (2 ml) and water (2 ml). The layers were separated using a hydrophobic frit and the aqueous phase was re-extracted with DCM (2 ml). The combined organic extracts were concentrated and the residue was dissolved in 1:1 MeOH:DMSO (1 ml) and purified by MDAP (Method A). The product containing fractions were evaporated under a stream of nitrogen to give the title compound as a white solid (13 mg).

LCMS (System B): $t_{RET}$=1.07 min; MH$^+$=335

Intermediate 21: 2-(Butyloxy)-8-(methyloxy)-9-[3-(1-pyrrolidinyl)propy]-9H-purin-6-amine

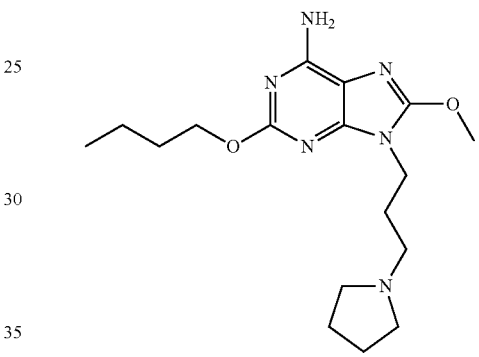

Prepared similarly to Intermediate 20 from 2-(butyloxy)-8-(methyloxy)-1H-purin-6-amine trifluoroacetate, 1,3-dibromopropane and pyrrolidine.

LCMS (System C): $t_{RET}$=0.60 min; MH$^+$=349

Intermediate 22: 2-(Butyloxy)-9-[3-(hexahydro-1H-azepin-1-yl)propyl]-8-(methyloxy)-9H-purin-6-amine

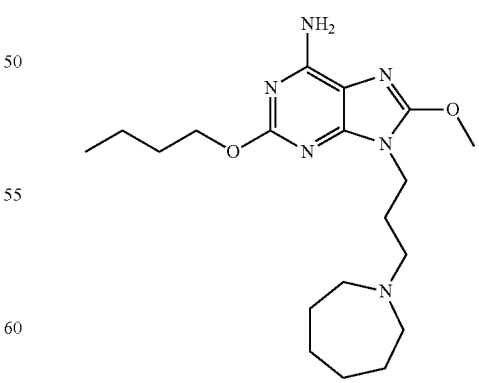

Prepared similarly to Intermediate 20 from 2-(butyloxy)-8-(methyloxy)-1H-purin-6-amine trifluoroacetate, 1,3-dibromopropane and hexahydro-1H-azepine.

LCMS (System B): $t_{RET}$=1.24 min; MH$^+$=377

Intermediate 23: 9-[4-(1-Azetidinyl)butyl]-2-(butyloxy)-8-(methyloxy)-9H-purin-6-amine

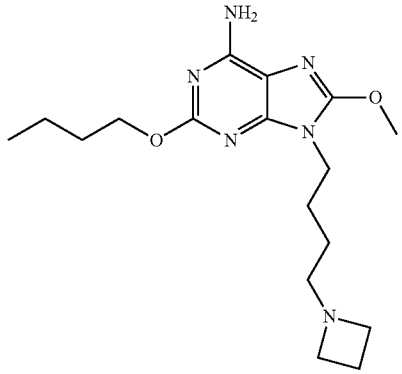 [SMILES: CCCCOc1nc(N)c2nc(OC)n(CCCCN3CCC3)c2n1]

2-(Butyloxy)-9-(4-chlorobutyl)-8-(methyloxy)-9H-purin-6-amine (100 mg, 0.305 mmol), azetidine (0.021 ml, 0.305 mmol) and N,N-diisopropylethylamine (0.107 ml, 0.610 mmol) were dissolved in DMF (2 ml) and heated at 50° C. for 48 hours. LCMS indicated the reaction to be incomplete and additional azetidine (0.021 ml, 0.305 mmol) and N,N-diisopropylethylamine (0.107 ml, 0.610 mmol) were added and the reaction mixture heated at 50° C. for a further 48 hours. The mixture was then partitioned between DCM (4 ml) and water (4 ml) and the layers separated using a hydrophobic frit. The aqueous phase was re-extracted with DCM (4 ml) and the combined organic extracts were concentrated and the residue purified by MDAP (Method A). The product-containing fractions were evaporated under a stream of nitrogen to give the title compound as a clear gum (7.6 mg).

LCMS (System B): $t_{RET}$=1.15 min; MH$^+$=349

Intermediate 24: 2-(Butyloxy)-8-(methyloxy)-9-[4-(1-pyrrolidinyl)butyl]-9H-purin-6-amine formic acid salt

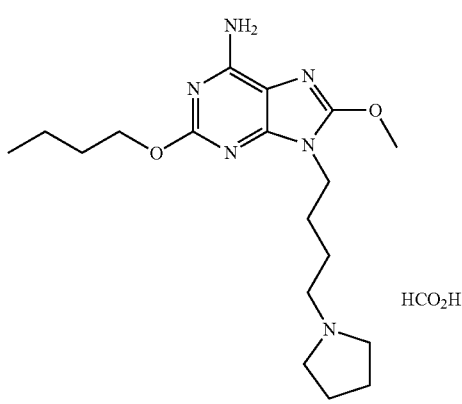 [SMILES: CCCCOc1nc(N)c2nc(OC)n(CCCCN3CCCC3)c2n1 ; "HCO2H"]

Prepared similarly to Intermediate 20 from 2-(butyloxy)-8-(methyloxy)-1H-purin-6-amine trifluoroacetate, 1,4-dibromobutane and pyrrolidine but with mass directed autopreparation using Method D.

LCMS (System B): $t_{RET}$=1.19 min; MH$^+$=363

Intermediate 25: 2-(Butyloxy)-8-(methyloxy)-9-[4-(1-piperidinyl)butyl]-9H-purin-6-amine formic acid salt

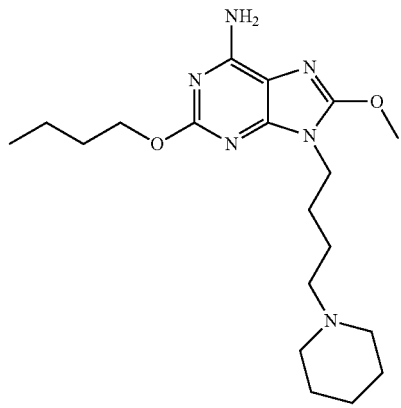

Prepared similarly to Intermediate 20 from 2-(butyloxy)-8-(methyloxy)-1H-purin-6-amine trifluoroacetate, 1,4-dibromobutane and piperidine but with sequential mass directed autopreparations using Method A followed by Method D.

LCMS (System B): $t_{RET}$=1.22 min; MH$^+$=377

Intermediate 26: 2-(Butyloxy)-9-[4-(hexahydro-1H-azepin-1-yl)butyl]-8-(methyloxy)-9H-Aurin-6-amine

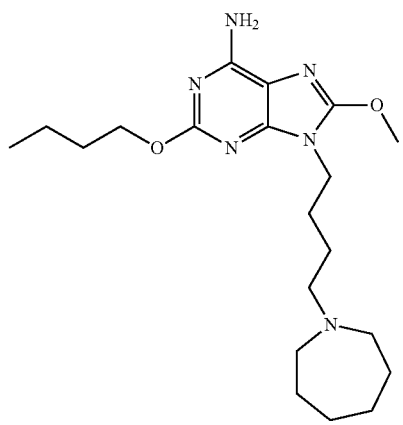 [SMILES: CCCCOc1nc(N)c2nc(OC)n(CCCCN3CCCCCC3)c2n1]

Prepared similarly to Intermediate 20 from 2-(butyloxy)-8-(methyloxy)-1H-purin-6-amine trifluoroacetate, 1,4-dibromobutane and hexahydro-1H-azepine.

LCMS (System B): $t_{RET}$=1.30 min; MH$^+$=391

Intermediate 27: 9-[5-(1-Azetidinyl)pentyl]-2-(butyloxy)-8-(methyloxy)-9H-purin-6-amine

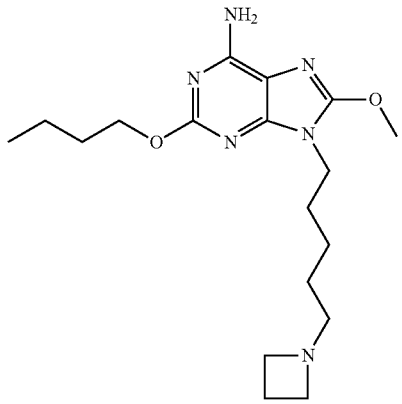 [SMILES: CCCCOc1nc(N)c2nc(OC)n(CCCCCN3CCC3)c2n1]

2-(Butyloxy)-9-(5-chloropentyl)-8-(methyloxy)-9H-purin-6-amine (100 mg, 0.293 mmol), azetidine (0.020 ml, 0.293 mmol) and N,N-diisopropylethylamine (0.102 ml, 0.585 mmol) were dissolved in DMF (2 ml) and heated at 50° C. for 72 hours. The solvent was removed in vacuo and the residue partitioned between DCM (5 ml) and water (5 ml) and the layers separated using a hydrophobic frit. The aqueous phase was re-extracted with DCM (5 ml) and the combined organic extracts concentrated and the residue dissolved in 1:1 MeOH:DMSO (1 ml) and purified by MDAP (Method A). The product-containing fractions were evaporated under a stream of nitrogen to give the title compound as a clear gum (6.8 mg).

LCMS (System B): $t_{RET}$=1.26 min; MH$^+$=363

Intermediate 28: 2-(Butyloxy)-8-(methyloxy)-9-[5-(1-pyrrolidinyl)pentyl]-9H-purin-6-amine

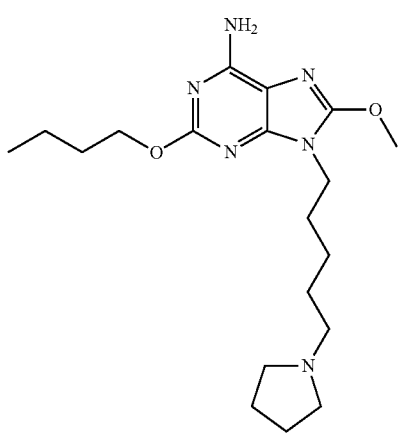 [SMILES: CCCCOc1nc(N)c2nc(OC)n(CCCCCN3CCCC3)c2n1]

Prepared similarly to Intermediate 27 from 2-(butyloxy)-9-(5-chloropentyl)-8-(methyloxy)-9H-purin-6-amine and pyrrolidine.

LCMS (System B): $t_{RET}$=1.27 min; MH$^+$=377

Intermediate 29: 2-(Butyloxy)-8-(methyloxy)-9-[5-(1-Diperidinyl)pentyl]-9H-purin-6-amine

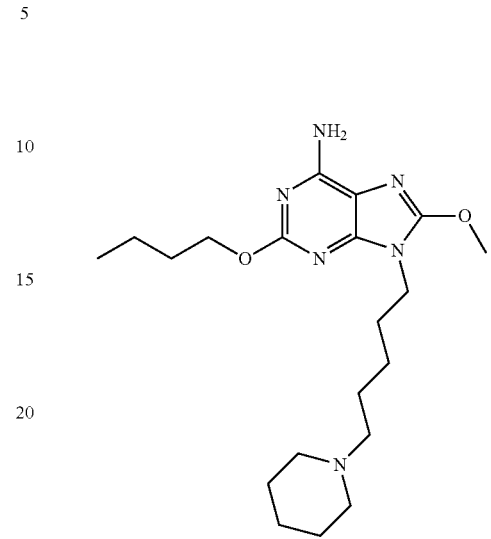

Prepared similarly to Intermediate 27 from 2-(butyloxy)-9-(5-chloropentyl)-8-(methyloxy)-9H-purin-6-amine and piperidine.

LCMS (System B): $t_{RET}$=1.33 min; MH$^+$=391

Intermediate 30: 2-(Butyloxy)-9-[5-(hexahydro-1H-azepin-1-yl)pentyl]-8-(methyloxy)-9H-purin-6-amine

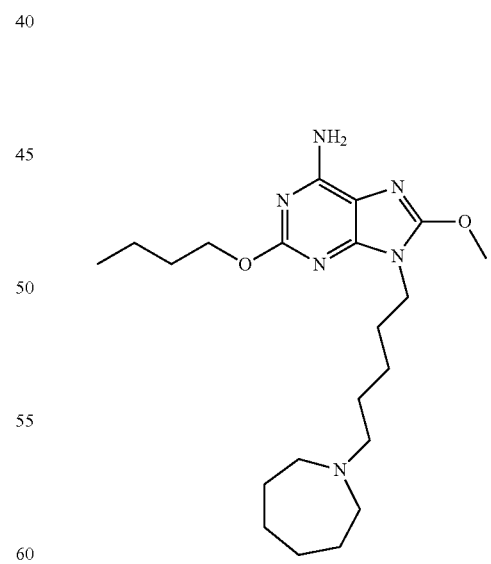

Prepared similarly to Intermediate 27 from 2-(butyloxy)-9-(5-chloropentyl)-8-(methyloxy)-9H-purin-6-amine and hexahydro-1H-azepine but with sequential purifications by MDAPs using Method A followed by Method E.

LCMS (System B): $t_{RET}$=1.38 min; MH$^+$=405

Intermediate 31: 2-(Butyloxy)-9-[5-(hexahydro-1 (2H)-azocinyl)pentyl]-8-(methyloxy)-9H-purin-6-amine

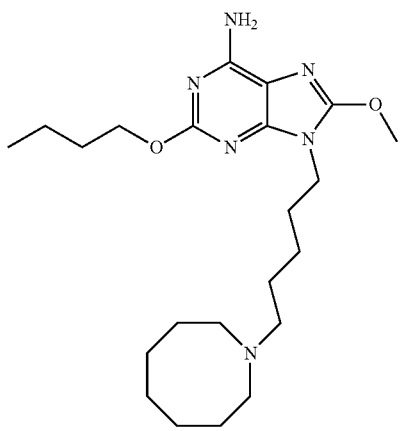 [SMILES: CCCCOc1nc(N)c2nc(OC)n(CCCCCN3CCCCCCC3)c2n1]

Prepared similarly to Intermediate 38 from 2-(butyloxy)-9-(5-chloropentyl)-8-(methyloxy)-9H-purin-6-amine and octahydroazocine.

LCMS (System B): $t_{RET}$=1.45 min; MH$^+$=419

Intermediate 32: 2-(Butyloxy)-8-(methyloxy)-9-[6-(1-pyrrolidinyl)hexyl]-9H-purin-6-amine

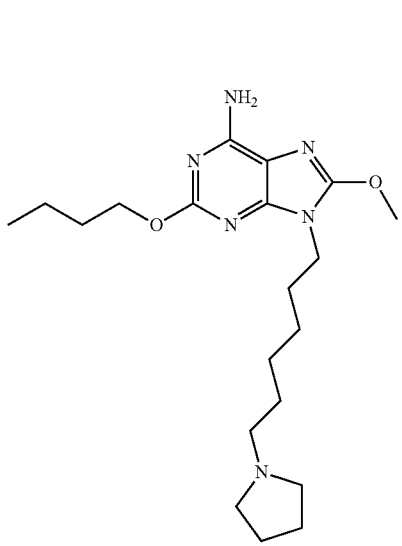 [SMILES: CCCCOc1nc(N)c2nc(OC)n(CCCCCCN3CCCC3)c2n1]

Prepared similarly to Intermediate 38 from 2-(butyloxy)-9-(6-chlorohexyl)-8-(methyloxy)-9H-purin-6-amine and pyrrolidine.

LCMS (System D): $t_{RET}$=2.97 min; MH$^+$=391

Intermediate 33: 2-(Butyloxy)-8-(methyloxy)-9-[6-(1-piperidinyl)hexyl]-9H-purin-6-amine

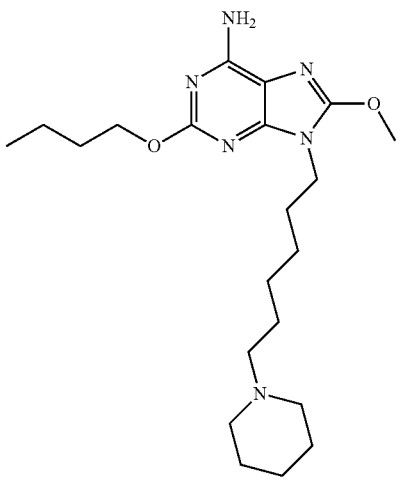 [SMILES: CCCCOc1nc(N)c2nc(OC)n(CCCCCCN3CCCCC3)c2n1]

Prepared similarly to Intermediate 38 from 2-(butyloxy)-9-(6-chlorohexyl)-8-(methyloxy)-9H-purin-6-amine and piperidine.

LCMS (System D): $t_{RET}$=3.12 min; MH$^+$=405

Intermediate 34: 2-(Butyloxy)-9-[6-(hexahydro-1H-azepin-1-yl)hexyl]-8-(methyloxy)-9H-purin-6-amine

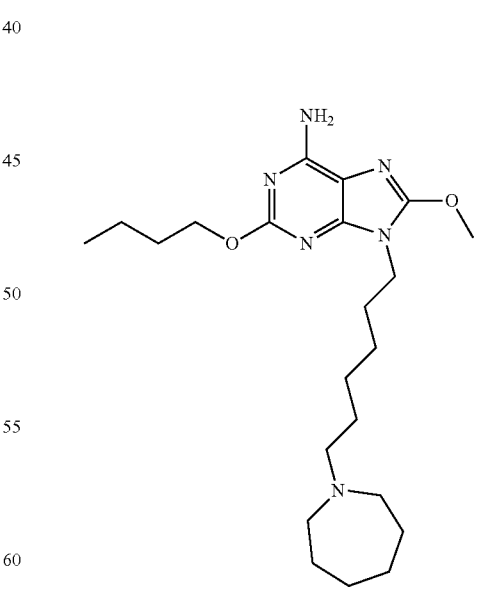

Prepared similarly to Intermediate 38 from 2-(butyloxy)-9-(6-chlorohexyl)-8-(methyloxy)-9H-purin-6-amine and hexahydro-1H-azepine.

LCMS (System D): $t_{RET}$=3.20 min; MH$^+$=419

Intermediate 35: N²-Butyl-8-(methyloxy)-9-[4-(1-piperidinyl)butyl]-9H-purine-2,6-diamine

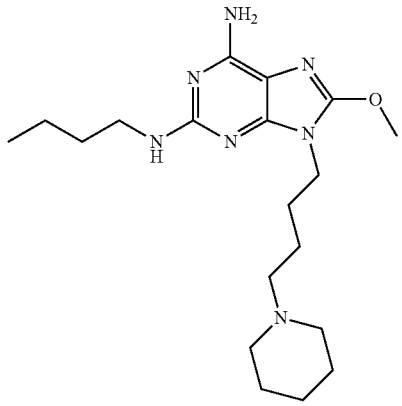 [SMILES: CCCCNc1nc(N)c2nc(OC)n(CCCCN3CCCCC3)c2n1]

N²-Butyl-8-(methyloxy)-3H-purine-2,6-diamine trifluoroacetate (192 mg, 0.547 mmol) and potassium carbonate (189 mg, 1.368 mmol) were suspended in DMF (3 ml) and heated to 60° C. for 1 hour. The reaction mixture was cooled to room temperature, 1-bromo-4-chlorobutane (0.063 ml, 0.547 mmol) added and the reaction stirred for a further 18 hours. Piperidine (0.054 ml, 0.547 mmol) and triethylamine (0.076 ml, 0.547 mmol) were added and the reaction mixture heated to 60° C. for 72 hours. The solvent was removed in vacuo and the residue partitioned between DCM (2 ml) and water (2 ml). The aqueous phase was re-extracted with DCM (2 ml) and the combined organic extracts were concentrated. The residue (ca.200 mg) was dissolved in 1:1 MeOH:DMSO (1 ml) and purified by MDAP (Method A). The product containing fractions were evaporated in vacuo to give the impure title compound as a yellow gum (106 mg) which was used without further purification.

LCMS (System B): $t_{RET}$=1.11 min; MH⁺=376

Intermediate 36: N²-Butyl-9-[4-(hexahydro-1H-azepin-1-yl)butyl]-8-(methyloxy)-9H-purine-2,6-diamine

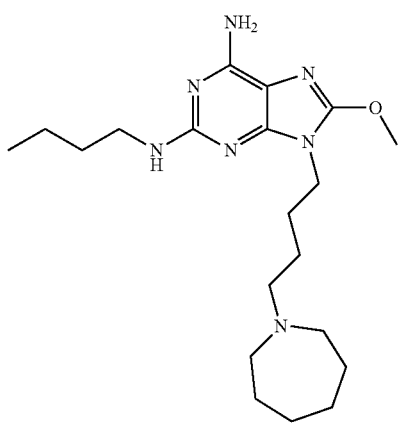 [SMILES: CCCCNc1nc(N)c2nc(OC)n(CCCCN3CCCCCC3)c2n1]

N²-Butyl-8-(methyloxy)-3H-purine-2,6-diamine trifluoroacetate (192 mg, 0.547 mmol) and potassium carbonate (189 mg, 1.368 mmol) were suspended in DMF (3 ml) and heated to 60° C. for 1 hour. The reaction mixture was cooled to room temperature, 1-bromo-4-chlorobutane (0.063 ml, 0.547 mmol) was added and the reaction stirred for a further 18 hours. Hexahydro-1H-azepine (54.2 mg, 0.547 mmol) and triethylamine (0.076 ml, 0.547 mmol) were added and the reaction mixture heated to 60° C. for 18 hours. The solvent was removed in vacuo and the residue was partitioned between DCM (5 ml) and water (5 ml). The aqueous phase was re-extracted with DCM (5 ml) and the combined organic extracts were concentrated in vacuo. The residue was dissolved in 1:1 MeOH:DMSO (2 ml) and purified in 2 injections by MDAP (Method B). This provided material (74 mg) that was still impure and which was repurified by MDAP (Method A). The product containing fractions were evaporated under a stream of nitrogen to give the title compound as a clear gum (13 mg).

LCMS (System B): $t_{RET}$=1.12 min; MH⁺=390

Intermediate 37: 9-[4-(Hexahydro-1H-azepin-1-yl)butyl]-2-{[(1S)-1-methylbutyl]oxy}-8-(methyloxy)-9H-purin-6-amine

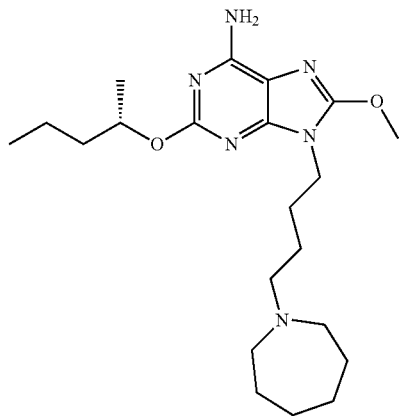 [SMILES: CCC[C@H](C)Oc1nc(N)c2nc(OC)n(CCCCN3CCCCCC3)c2n1]

Prepared similarly to Intermediate 36 from 2-{[(1S)-1-methylbutyl]oxy}-8-(methyloxy)-1H-purin-6-amine trifluoroacetate, 1-bromo-4-chlorobutane, and hexahydro-1H-azepine but with three sequential MDAPs using Method B followed by Method A (x2).

LCMS (System B): $t_{RET}$=1.41 min; MH⁺=405

Intermediate 38: 2-{[(1S)-1-Methylbutyl]oxy}-8-(methyloxy)-9-[5-(1-piperidinyl)pentyl]-9H-purin-6-amine

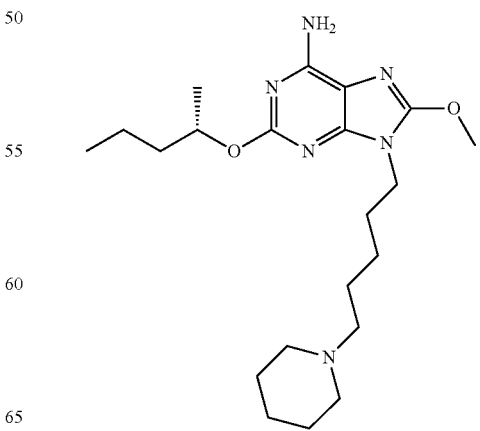

9-(5-Chloropentyl)-2-{[(1S)-1-methylbutyl]oxy}-8-(methyloxy)-9H-purin-6-amine (80 mg, 0.225 mmol), triethylamine (0.031 ml, 0.225 mmol) and piperidine (0.045 ml, 0.45 mmol) were suspended in DMF (3 ml) and the mixture heated to 70° C. for 18 hours. The solvent was removed and the residue partitioned between DCM (4 ml) and saturated sodium bicarbonate (4 ml). The aqueous phase was re-extracted with further DCM and the combined organic extracts were concentrated and the residue dissolved in 1:1 MeOH:DMSO (1 ml) and purified by MDAP (Method A). The product -containing fractions were combined and evaporated under a stream of nitrogen to give the title compound (47.2 mg).

LCMS (System D): $t_{RET}$=3.11 min; MH$^+$=405

Intermediate 39: 2-Fluoro-9-(tetrahydro-2H-pyran-2-yl)-9H -purin-6-amine

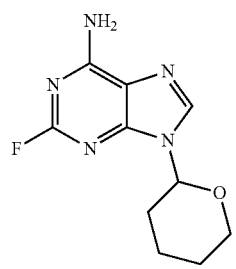 [SMILES: Nc1nc(F)nc2c1ncn2C1CCCCO1]

N,O-bis(trimethylsilyl)acetamide (975 mL, 3.988 mol) was added to a stirred suspension of 2-fluoro-1H-purin-6-amine (200 g, 1.306 mmol) (available from, for example, AlliedSignal, US) in anhydrous acetonitrile (4 L) in a 10 L controlled lab reactor and the resulting mixture heated to reflux and maintained at that temperature for 2 hours. The circulator was then re-programmed and the reaction mixture cooled to 0° C. A solution of tetrahydropyranyl acetate (preparation described in Tetrahedron Letters 2006, 47(27), 4741) (282 g, 1.959 mol) in anhydrous acetonitrile (500 ml) was then added slowly via a dropping funnel followed by trimethylsilyl trifluoromethanesulfonate (283 mL, 1.567 mol) dropwise via a dropping funnel. No sigificant exotherm was observed. The circulator temperature was re-adjusted to 10° C. and stirring maintained for a further 1 hour. The mixture was then quenched by addition of 1M sodium carbonate (4 L). A solid precipitate was observed and the pH checked to be basic. Additional water was added to the suspension (1 L) and on standing the layers separated with the aqueous layer containing significant solid inorganics. The majority of the aqueous and inorganic solid was separated. The organic layer still contained significant solid and was cooled to 0° C. with stirring to encourage further precipitation. The solid was the collected by filtration and the pad was washed very well with water then dried in vacuo at 40° C. overnight to give the title compound as a cream coloured solid (152.8 g).

LCMS (System D): $t_{RET}$=1.71 min; MH$^+$=238

Intermediate 40: 2-{[(1S)-1-Methylpropyl]oxy}-9-(tetrahydro-2H-pyran-2-yl)-9H-purin-6-amine

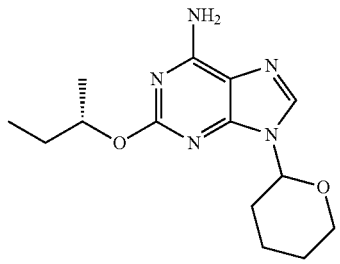 [SMILES: CC[C@H](C)Oc1nc(N)c2ncn(C3CCCCO3)c2n1]

Sodium tert-butoxide (3.24 g, 33.7 mmol) was added portionwise with stirring to (2S)-2-butanol (10 g, 135 mmol). 2-Fluoro-9-(tetrahydro-2H-pyran-2-yl)-9H-purin-6-amine (2 g, 8.43 mmol) was added to the resulting suspension and the mixture heated to 50° C. for 6 hours when LCMS showed complete reaction. After cooling the mixture was diluted with ethyl acetate (100 ml), and washed with water (50 ml) and the aqueous layer extracted again with ethyl acetate (50 ml). The combined organic extracts were washed with brine, dried using a hydrophobic frit and evaporated in vacuo (at 62° C. to remove the excess alcohol). The residue (2.52 g) was dissolved in dichloromethane and purified on an aminopropyl cartridge (110 g) using a FlashmasterII apparatus and eluting with a 0-100% ethyl acetate in cyclohexane gradient over 60 mins. The appropriate fractions were combined and evaporated in vacuo to give the title compound as a white solid (1.935 g).

LCMS (System D): $t_{RET}$=2.41 min; MH$^+$=292

Intermediate 41: 8-Bromo-2-{[(1S)-1-methylpropyl]oxy}-9-(tetrahydro-2H-pyran-2-yl)-9H-burin-6-amine

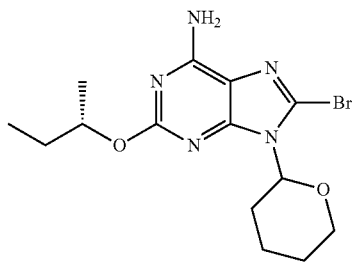 [SMILES: CC[C@H](C)Oc1nc(N)c2nc(Br)n(C3CCCCO3)c2n1]

N-Bromosuccinimide (1.182 g, 6.64 mmol) was added portionwise to a solution of 2-{[(1S)-1-methylpropyl]oxy}-9-(tetrahydro-2H-pyran-2-yl) -9H-purin-6-amine (1.935 g, 6.64 mmol) in chloroform (50 ml) at 0-5° C. The resulting green solution was stirred at 0-5° C. for 1 hour during which time it turned red and the mixture was then allowed to warm to room temperature and stirred overnight. The resulting green solution was washed with water (2×20 ml), separated using a hydrophobic frit and concentrated.

The residue was dissolved in dichloromethane and purified by silica gel chromatography (100 g cartridge) using a Flashmaster II apparatus and a 0-100% ethyl acetate-cyclohexane gradient over 60 mins. The appropriate fractions were combined and evaporated in vacuo to give the title compound as a yellow foam (1.79 g).

LCMS (System B): $t_{RET}$=2.58 min; MH$^+$=370/372

Intermediate 42: 8-(Methyloxy)-2-{[(1S)-1-methylpropyl]oxy}-9-(tetrahydro-2H-pyran-2-yl)-9H-purin-6-amine

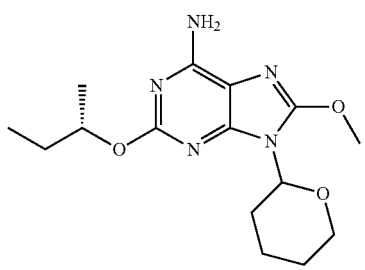 [SMILES: CC[C@H](C)Oc1nc(N)c2nc(OC)n(C3CCCCO3)c2n1]

8-Bromo-2-{[(1S)-1-methylpropyl]oxy}-9-(tetrahydro-2H-pyran-2-yl)-9H-purin-6-amine (1.79 g, 4.83 mmol) was dissolved in methanol (15 ml) and 25% sodium methoxide in methanol (3.2 ml, 4.83 mmol) was added and the mixture heated to reflux for 2.5 hours. The reaction mixture was left standing at room temperature overnight and then concentrated in vacuo and the residue partitioned between dichloromethane (40 ml) and saturated ammonium chloride solution (40 ml). The layers were separated using a hydrophobic frit and the aqueous phase was re-extracted with dichloromethane (40 ml). The combined organic extracts were concentrated in vacuo to give the title compound as a yellow foam (1.65 g).

LCMS (System B): $t_{RET}$=2.11 min; MH$^+$=322

Intermediate 43: 8-(Methyloxy)-2-{[(1S)-1-methylpropyl]oxy}-1H-purin-6-amine trifluoroacetate

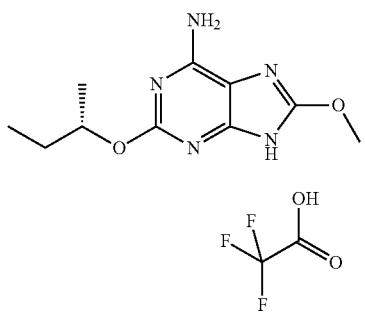 [SMILES: CC[C@H](C)Oc1nc(N)c2nc(OC)[nH]c2n1 ; O=C(O)C(F)(F)F]

Prepared similarly to Intermediate 12 from 8-(methyloxy)-2-{[(1S)-1-methylpropyl]oxy}-9-(tetrahydro-2H-pyran-2-yl)-9H-purin-6-amine.

LCMS (System B): $t_{RET}$=1.19 min; MH$^+$=238

Intermediate 44: 9-(4-Chlorobutyl)-8-(methyloxy)-2-{[(1S)-1-methylpropyl]oxy}-9H-purin-6-amine

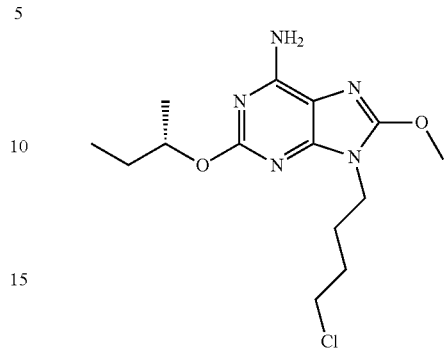

Prepared similarly to Intermediate 18 from 8-(methyloxy)-2-{[(1S)-1-methylpropyl]oxy}-1H-purin-6-amine trifluoroacetate and 1-bromo-4-chlorobutane with purification on an aminopropyl (NH$_2$) cartridge using a 0-100% ethyl acetate-cyclohexane gradient.

LCMS (System D): $t_{RET}$=2.83 min; MH$^+$=328/330

Intermediate 45: 2-{[(1S)-1-Methylpentyl]oxy}-9-(tetrahydro-2H-pyran-2-yl)-9H-purin-6-amine

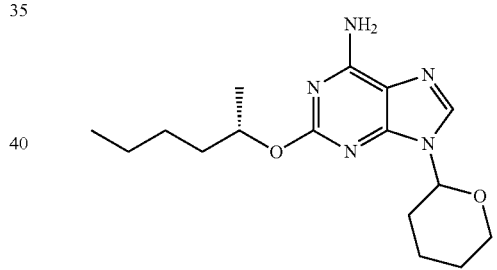

Sodium t-butoxide (4.86 g, 50.6 mmol) was added portionwise to a stirred mixture of (S)-2-hexanol (12 g, 117 mmol) and 1,2-dimethoxyethane (12 ml). The resultant mixture was heated to 50° C. under an atmosphere of nitrogen and then 2-fluoro-9-(tetrahydro-2H-pyran-2-yl)-9H-purin-6-amine (3 g, 12.65 mmol) was added. The resultant mixture was maintained at 50° C. for 20 hours when LCMS indicated complete reaction. The mixture was cooled to room temperature and partitioned between ethyl acetate (100 ml) and water (100 ml). The organic phase was washed with water (100 ml) then saturated brine (50 ml), dried over anhydrous magnesium sulphate, filtered and evaporated. The residue was dissolved in dichloromethane and purified on an aminopropyl (NH$_2$) cartridge (100 g) eluting with a 0-100% ethyl acetate in cyclohexane gradient over 40 mins. The appropriate fractions were combined and evaporated in vacuo to give the title compound as a white foam (1.665 g).

LCMS (System D): $t_{RET}$=2.88 min; MH$^+$=320

Intermediate 46: 8-Bromo-2-{[(1S)-1-methylpentyl]oxy}-9-(tetrahydro-2H-pyran-2-yl)-9H-purin-6-amine

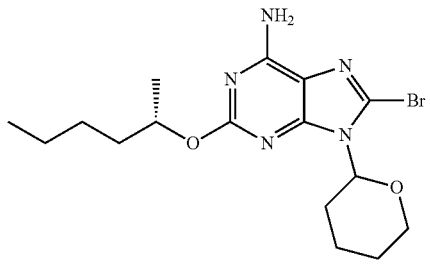 [SMILES: CCCC[C@H](C)Oc1nc(N)c2nc(Br)n(C3CCCCO3)c2n1]

N-Bromosuccinimide (1.504 g, 8.45 mmol) was added portionwise to a stirred solution of 2-{[(1S)-1-methylpentyl]oxy}-9-(tetrahydro-2H-pyran-2-yl)-9H-purin-6-amine (2.453 g, 7.68 mmol) in chloroform (40 ml) under at atmosphere of nitrogen cooled in an ice-bath. After 3 hours LCMS indicated the reaction to be 80% complete and more N-bromosuccinimide (0.68 g) was added and stirring continued for a further 2 hours. Water (40 ml) was added and the phases separated using a hydrophobic frit. The organic phase was evaporated and the residue dissolved in dichloromethane and purified on an aminopropyl (NH$_2$) cartridge (100 g) using a 0-100% ethyl acetate in cyclohexane gradient followed by a 0-20% methanol (+1% triethylamine) gradient over 60 mins. The appropriate fractions were combined and evaporated in vacuo to the title compound as a white foam (2.38 g).

LCMS (System D): $t_{RET}$=3.24 min; MH$^+$=398/400

Intermediate 47: 8-(Methyloxy)-2-{[(1S)-1-methylpentyl]oxy}-9-(tetrahydro-2H-pyran-2-yl)-9H-purin-6-amine

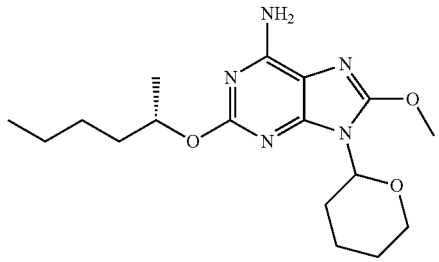 [SMILES: CCCC[C@H](C)Oc1nc(N)c2nc(OC)n(C3CCCCO3)c2n1]

A solution of sodium methoxide in methanol (0.5M, 20 ml, 10 mmol) was added to a solution of 8-bromo-2-{[(1S)-1-methylpentyl]oxy}-9-(tetrahydro-2H-pyran-2-yl)-9H-purin-6-amine (2.368 g, 5.95 mmol) in methanol (10 ml) and the mixture heated under reflux for 5 hours. More sodium methoxide in methanol (4 ml, 2 mmol) was added and the mixture refluxed for a further 2 hours and then cooled and evaporated. The residue was partitioned between ethyl acetate (100 ml) and water (100 ml). The organic phase was separated, washed with saturated brine, dried over anhydrous magnesium sulphate, filtered and evaporated. The residue was dissolved in dichloromethane and purified on an aminopropyl (NH$_2$) cartridge (100 g) using a 0-100% ethyl acetate in cyclohexane gradient over 40 mins. The appropriate fractions were combined and evaporated in vacuo to give the title compound as a white foam (1.725 g).

LCMS (System D): $t_{RET}$=3.06 min; MH$^+$=350

Intermediate 48: 8-(Methyloxy)-2-{[(1S)-1-methylpentyl]oxy}-1H-purin-6-amine trifluoroacetate

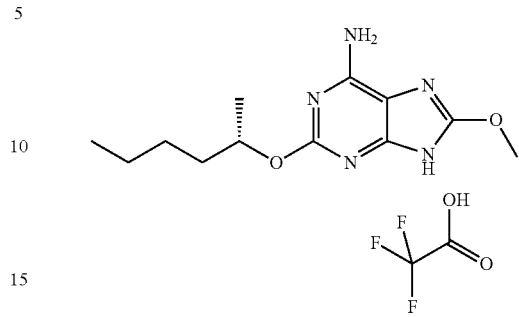

Trifluoroacetic acid (2.3 ml, 3.40 g, 29.9 mmol) was added to a stirred solution of 8-(methyloxy)-2-{[(1S)-1-methylpentyl]oxy}-9-(tetrahydro-2H-pyran-2-yl)-9H-purin-6-amine (1.479 g, 4.23 mmol) in methanol (25 ml). The resultant mixture was stirred for 66 hours under an atmosphere of nitrogen and then evaporated and dried in vacuo to give the title compound as a white solid (1.65 g).

LCMS (System D): $t_{RET}$=2.14 min; MH$^+$=266

Intermediate 49: 9-(4-Chlorobutyl)-8-(methyloxy)-2-{[(1S)-1-methylpentyl]oxy}-9H-purin-6-amine

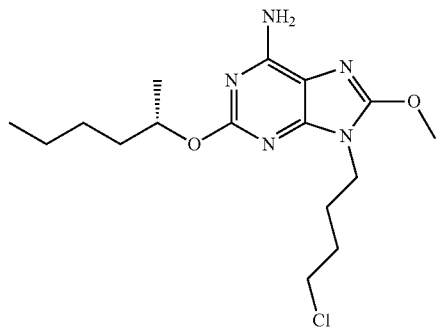 [SMILES: CCCC[C@H](C)Oc1nc(N)c2nc(OC)n(CCCCCl)c2n1]

Prepared similarly to Intermediate 44 from 8-(methyloxy)-2-{[(1S)-1-methylpentyl]oxy}-1H-purin-6-amine trifluoroacetate and 1-bromo-4-chlorobutane.

LCMS (System D): $t_{RET}$=3.22 min; MH$^+$=356/358

Intermediate 50: 2-[(1-Methylethyl)oxy]-9-(tetrahydro-2H-pyran-2-yl)-9H-purin-6-amine

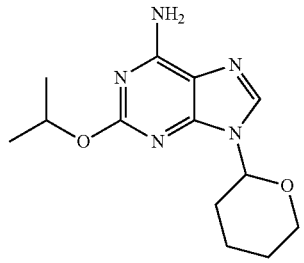 [SMILES: CC(C)Oc1nc(N)c2ncn(C3CCCCO3)c2n1]

Sodium t-butoxide (1.30 g, 13.53 mmol) was added to 2-propanol (16.95 ml, 220 mmol) portionwise with stirring over 5 mins. 2-Fluoro-9-(tetrahydro-2H-pyran-2-yl)-9H-purin-6-amine (2 g, 8.43 mmol) was added and the reaction mixture heated and stirred at 50° C. for 4 hours and then allowed to cool to room temperature. The reaction mixture was then diluted with ethyl acetate (75 ml), washed with water (3×25 ml) and the combined aqueous layers extracted again with ethyl acetate (2×25 ml). The combined organic layers were dried by passage through a hydrophobic frit, filtered and evaporated to give an off-white solid (2.30 g). This material was dissolved in dichloromethane and purified using an aminopropyl SPE cartridge (70 g) eluted with a 0-100% ethyl acetate in cyclohexane gradient. The appropriate fractions were combined and evaporated to give a white solid (1.6 g) which was further purified by column chromatography using a reverse phase ($C_{18}$) Flashmaster II system loading in 1:1 MeOH/DMSO and eluting with 0-50% acetonitrile (+0.1% TFA) in water (+0.1% TFA) gradient over 40 mins. collecting fractions in vials containing ca. 2 mL of saturated aqueous sodium bicarbonate solution. The appropriate fractions were combined, and extracted with dichloromethane (3×100 mL). The combined organic extracts were dried by passage through a hydrophobic frit and evaporated to give the title compound as a white solid (888 mg).

LCMS (System B): $t_{RET}$=1.76 min; MH$^+$=278

Intermediate 51: 8-Bromo-2-[(1-methylethyl)oxy]-9-(tetrahydro-2H-pyran-2-yl)-9H-purin-6-amine

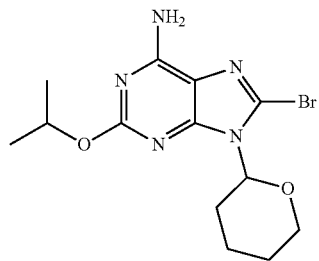 [SMILES: CC(C)Oc1nc(N)c2nc(Br)n(C3CCCCO3)c2n1]

N-Bromosuccinimide (604 mg, 3.39 mmol) was added to a solution of 2-[(1-methylethyl)oxy]-9-(tetrahydro-2H-pyran-2-yl)-9H-purin-6-amine (888 mg, 3.20 mmol) in chloroform (30 ml) at 0-5° C. under nitrogen. The mixture was stirred at 0-5° C. for 1 hour during which time it became reddish brown in colour and it was then warmed to room temperature and stirred for a further 4 hours. LCMS indicated the reaction to be incomplete and more N-bromosuccinimide (114 mg, 0.641 mmol) was added and the reaction mixture stirred at room temperature overnight. The reaction mixture was then diluted with chloroform (30 ml), washed with water (2×20 ml) and the layers were separated using a hydrophobic frit and the organic layer was evaporated to give a red solid (1.16 g). This material was dissolved in dichloromethane and purified by silica gel chromatography on an SPE cartridge (50 g) using a 0-100% ethyl acetate in cyclohexane gradient as eluent. The appropriate fractions were combined and evaporated to give the title compound as a pale yellow solid 712 mg.

LCMS (System B): $t_{RET}$=2.36 min; MH$^+$=356/358

Intermediate 52: 2-[(1-Methylethyl)oxy]-8-(methyloxy)-9-(tetrahydro-2H-pyran-2-yl)-9H-purin-6-amine

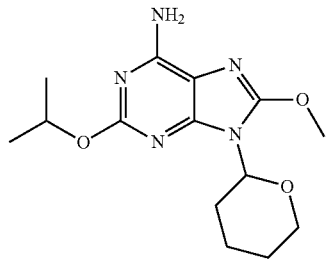 [SMILES: COc1nc2c(N)nc(OC(C)C)nc2n1C1CCCCO1]

To a stirred suspension of 8-bromo-2-[(1-methylethyl)oxy]-9-(tetrahydro-2H-pyran-2-yl)-9H-purin-6-amine (690 mg, 1.937 mmol) in methanol (15 ml) was added sodium methoxide (30% wt/v solution in methanol, 2.4 ml) and the reaction mixture heated at 50° C. for 2 hours. The reaction mixture was then heated to 70° C. and stirred for 2.5 hours. The solvent was evaporated and the residue partioned between saturated aqueous ammonium chloride solution (15 ml) and ethyl acetate (20 mL). The layers were separated, the aqueous phase was extracted with additional ethyl acetate (2×10 mL) and the organic extracts were combined, dried by passage through a hydrophobic frit and evaporated to give the title compound as a yellow solid (573 mg).

LCMS (System B): $t_{RET}$=1.92 min; MH$^+$=308

Intermediate 53: 2-[(1-Methylethyl)oxy]-8-(methyloxy)-1H-purin-6-amine trifluoroacetate

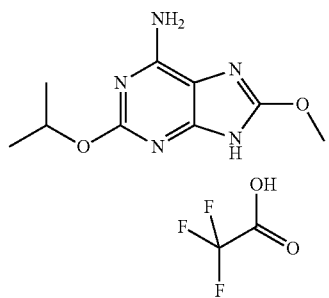

Trifluoroacetic acid (1 ml, 12.98 mmol) was added to a stirred solution of 2-[(1-methylethyl)oxy]-8-(methyloxy)-9-(tetrahydro-2H-pyran-2-yl)-9H-purin-6-amine (568 mg, 1.848 mmol) in methanol (10 ml) and the mixture was stirred at room temperature overnight. More trifluoroacetic acid (0.2 ml) was added and the reaction mixture stirred ar room temperature for a further 1.5 hours and then evaporated in vacuo. The solid residue was triturated with ethyl acetate, collected by filtration, washed with ethyl acetate and dried in vacuo overnight to give the title compound as a white solid (405 mg).

LCMS (System B): $t_{RET}$=1.02 min; MH$^+$=224

Intermediate 54: 9-(5-Chlorobentyl)-2-[(1-methylethyl)oxy]-8-(methyloxy)-9H-purin-6-amine

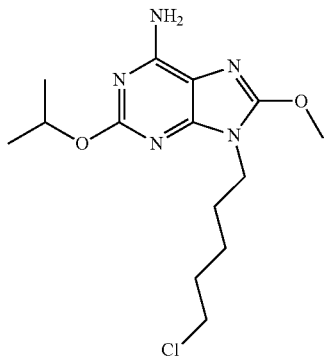 [SMILES: COc1nc2c(N)nc(OC(C)C)nc2n1CCCCCCl]

Prepared similarly to Intermediate 44 from 2-[(1-methylethyl)oxy]-8-(methyloxy)-1H-purin-6-amine trifluoroacetate and 1-bromo-5-chloropentane.

LCMS (System A): $t_{RET}$=0.93 min; MH$^+$=328/330

Intermediate 55: 2-(Cyclobutyloxy)-9-(tetrahydro-2H-pyran-2-yl)-9H-purin-6-amine

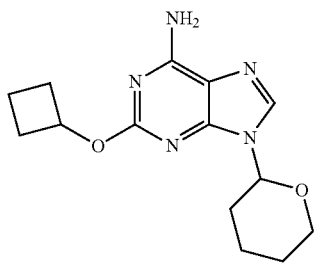 [SMILES: Nc1nc(OC2CCC2)nc2c1ncn2C1CCCCO1]

Sodium t-butoxide (3.31 g, 34.2 mmol) was added portionwise to cyclobutanol (10 ml) at room temperature. The mixture became very thick and was heated to 50° C. 2-Fluoro-9-(tetrahydro-2H-pyran-2-yl)-9H-purin-6-amine (2 g, 8.43 mmol) was added followed by 1,2-dimethoxyethane (3 ml) and the mixture stirred at 50° C. for 90 mins. and then cooled and partitioned between ethyl acetate (50 ml) and water (50 ml). A precipitate that failed to dissolve in either phase was removed by filtration. The organic phase was separated, washed with saturated brine, dried over anhydrous magnesium sulphate, filtered and evaporated to give a cream foam. This material was dissolved in dichloromethane and purified on an aminopropyl (NH$_2$) cartridge (110 g) using a 0-100% ethyl acetate in cyclohexane gradient followed by a 0-20% methanol (+1% triethylamine) gradient over 40 mins. The appropriate fractions were combined and evaporated in vacuo to give the title compound as an off-white solid (0.655 g).

LCMS (System B): $t_{RET}$=1.98 min; MH$^+$=290

Intermediate 56: 8-Bromo-2-(cyclobutyloxy)-9-(tetrahydro-2H-pyran-2-yl)-9H-purin-6-amine

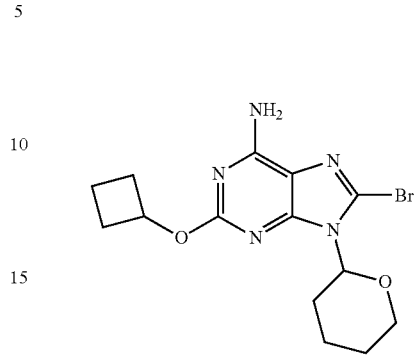

N-Bromosuccinimide (1.152 g, 6.47 mmol) was added to a stirred solution of 2-(cyclobutyloxy)-9-(tetrahydro-2H-pyran-2-yl)-9H-purin-6-amine (1.248 g, 4.31 mmol) in chloroform (15 ml) at 0° C. The mixture was warmed to room temperature and left overnight when water (15 ml) was added and the phases separated. The aqueous layer was extracted with dichloromethane and the organic extracts were combined, washed with brine, dried over anhydrous magnesium sulphate and evaporated to give the title compound as an orange foam (1.79 g).

LCMS (System D): $t_{RET}$=2.72 min; MH$^+$=368/370

Intermediate 57: 2-(Cyclobutyloxy)-8-(methyloxy)-9-(tetrahydro-2H-pyran-2-yl)-9H-purin-6-amine

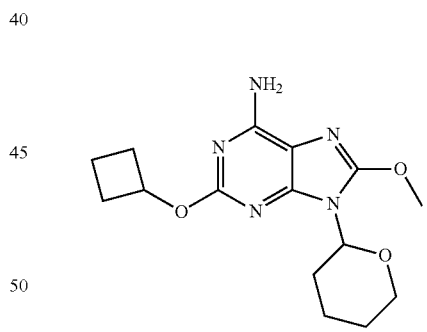

8-Bromo-2-(cyclobutyloxy)-9-(tetrahydro-2H-pyran-2-yl)-9H-purin-6-amine (1.79 g, 4.86 mmol) was dissolved in anhydrous methanol (25 ml) and 25% sodium methoxide in methanol (2.274 ml, 9.72 mmol) was added under nitrogen. The mixture was heated at 67° C. for 24 hours and then cooled to room temperature. Ethyl acetate and water were added and the layers separated. The aqueous layer was extracted twice more with ethyl acetate, and the organic extracts were combined, washed with brine, dried over anhydrous magnesium sulfate, and evaporated to give the title compound as a cream foam (1.27 g).

LCMS (System D): $t_{RET}$=2.53 min; MH$^+$=320

Intermediate 58: 2-(Cyclobutyloxy)-8-(methyloxy)-1H-purin-6-amine trifluoroacetate

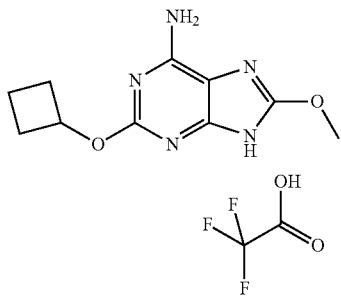

Trifluoroacetic acid (3 ml, 38.9 mmol) was added to a solution of 2-(cyclobutyloxy)-8-(methyloxy)-9-(tetrahydro-2H-pyran-2-yl)-9H-purin-6-amine (1.27 g, 3.98 mmol) in methanol (50 ml) and the mixture stirred at 20° C. under an atmosphere of nitrogen for 21 hours. The solvent was removed in vacuo, and the residual solid was triturated with 1,1-dimethylethyl methyl ether and then collected by filtration and dried in vacuo to give the title compound as a cream solid (1.0922 g).

LCMS (System D): $t_{RET}$=1.17 min; $MH^+$=236

Intermediate 59: 9-(4-Chlorobutyl)-2-(cyclobutyloxy)-8-(methyloxy)-9H-purin-6-amine

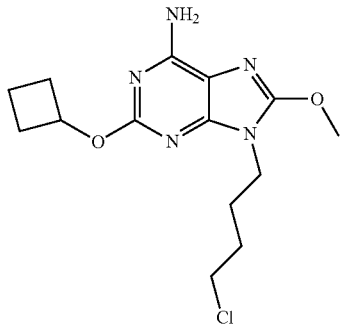 [SMILES: COc1nc2c(N)nc(OC3CCC3)nc2n1CCCCCl]

Prepared similarly to Intermediate 44 from 2-(cyclobutyloxy)-8-(methyloxy)-1H-purin-6-amine trifluoroacetate and 1-bromo-4-chlorobutane.

LCMS (System D): $t_{RET}$=2.76 min; $MH^+$=326/328

Intermediate 60: 2-(Cyclopentyloxy)-9-(tetrahydro-2H-pyran-2-yl)-9H-purin-6-amine

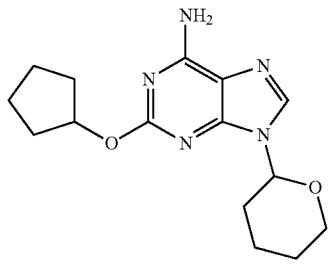 [SMILES: Nc1nc(OC2CCCC2)nc2c1ncn2C1CCCCO1]

Cyclopentanol (25 ml, 275 mmol) was added to sodium tert-butoxide (4.05 g, 42.2 mmol) to give a thick suspension which was diluted with 1,2-dimethoxyethane (35 ml) and heated to 50° C. 2-Fluoro-9-(tetrahydro-2H-pyran-2-yl)-9H-purin-6-amine (2.5 g, 10.54 mmol) was added to the resulting solution which was then stirred under nitrogen at 50° C. for 20 hours. The mixture was cooled and water and ethyl acetate were added. The layers separated and the aqueous layer washed again with ethyl acetate. The organic extracts were combined, washed with brine, dried over anhydrous magnesium sulphate and concentrated under reduced pressure at 40° C. The residue was loaded in cyclohexane (50 ml) onto 330 g silica cartridge and eluted firstly with a 0-100% ethyl acetate in cyclohexane gradient over 10 column volumes and then with a 0-30% methanol in ethyl acetate gradient. Product-containing fractions were combined and evaporated to give the title compound as a white foam (2.51 g).

LCMS (System D): $t_{RET}$=2.51 min; $MH^+$=304

Intermediate 61: 8-Bromo-2-(cyclopentyloxy)-9-(tetrahydro-2H-pyran-2-yl)-9H-purin-6-amine

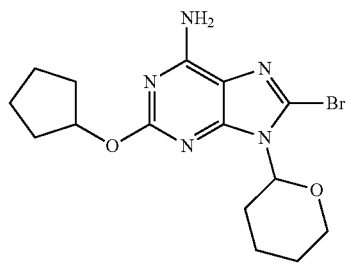 [SMILES: Nc1nc(OC2CCCC2)nc2c1nc(Br)n2C1CCCCO1]

Prepared similarly to Intermediate 56 from 2-(cyclopentyloxy)-9-(tetrahydro-2H-pyran-2-yl)-9H-purin-6-amine.

LCMS (System D): $t_{RET}$=2.88 min; $MH^+$=382/384

Intermediate 62: 2-(Cyclooentyloxy)-8-(methyloxy)-9-(tetrahydro-2H-pyran-2-yl)-9H-purin-6-amine

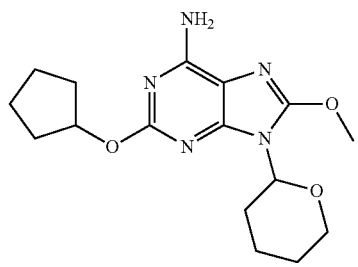 [SMILES: COc1nc2c(N)nc(OC3CCCC3)nc2n1C1CCCCO1]

Prepared similarly to Intermediate 57 from 8-bromo-2-(cyclopentyloxy)-9-(tetrahydro-2H-pyran-2-yl)-9H-purin-6-amine.

LCMS (System C): $t_{RET}$=1.11 m in; $MH^+$=334

Intermediate 63: 2-(Cyclooentyloxy)-8-(methyloxy)-1H-purin-6-amine trifluoroacetate

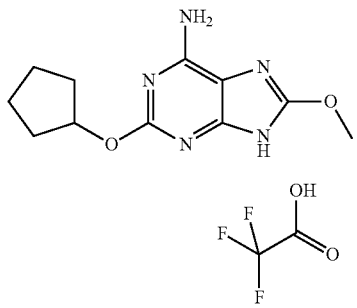 [SMILES: COc1nc2c(N)nc(OC3CCCC3)nc2[nH]1 ; O=C(O)C(F)(F)F]

Prepared similarly to Intermediate 58 from 2-(cyclopentyloxy)-8-(methyloxy)-9-(tetrahydro-2H-pyran-2-yl)-9H-purin-6-amine.

LCMS (System B): $t_{RET}$=1.27 min; MH$^+$=250

Intermediate 64: 9-(4-Chlorobutyl)-2-(cyclopentyloxy)-8-(methyloxy)-9H-purin-6-amine

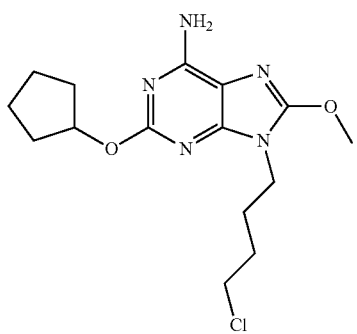 [SMILES: COc1nc2c(N)nc(OC3CCCC3)nc2n1CCCCCl]

Prepared similarly to Intermediate 44 from 2-(cyclopentyloxy)-8-(methyloxy)-1H-purin-6-amine trifluoroacetate and 1-bromo-4-chlorobutane.

LCMS (System D): $t_{RET}$=2.90 min; MH$^+$=340/342

Intermediate 65: 2-(Cyclohexyloxy)-9-(tetrahydro-2H-pyran-2-yl)-9H-purin-6-amine

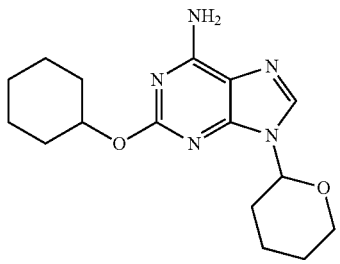 [SMILES: Nc1nc(OC2CCCCC2)nc2c1ncn2C1CCCCO1]

Sodium tert-butoxide (3.29 g, 34.2 mmol) was added portionwise to cyclohexanol (15 ml) at room temperature. The mixture became very thick and more cyclohexanol (10 ml) was added and the mixture heated to 50° C. 2-Fluoro-9-(tetrahydro-2H-pyran-2-yl)-9H-purin-6-amine (2 g, 8.43 mmol) was added and the mixture heated at 50° C. for 1 hour and then warmed to 60° C. and heated for a further 2 hours at which point LCMS showed complete reaction. The mixture was cooled to room temperature and partitioned between ethyl acetate (150 ml) and water (150 ml). The organic phase was separated, washed with saturated brine, dried over anhydrous magnesium sulphate, filtered and evaporated on a water bath at 60° C. The residue was dissolved in dichloromethane and purified on a 70 g aminopropyl (NH$_2$) cartridge using a 0-100% ethyl acetate in cyclohexane gradient followed by a 0-20% methanol (+1% triethylamine) gradient over 30 mins. Some product-containing fractions were contaminated with cyclohexanol and these were re-purified on a 70 g silica cartridge using a 0-100% ethyl acetate-cyclohexane gradient over 40 mins. Product-containing fractions from the two purifications were combined and evaporated in vacuo to give the title compound as a pale yellow foam (1.59 g).

LCMS (System D): $t_{RET}$=2.65 min; MH$^+$=318

Intermediate 66: 8-Bromo-2-(cyclohexyloxy)-9-(tetrahydro-2H-pyran-2-yl)-9H-purin-6-amine

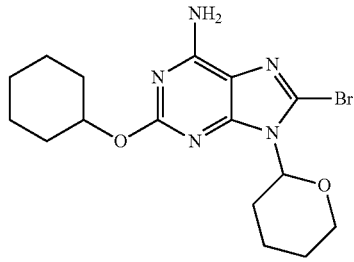 [SMILES: Nc1nc(OC2CCCCC2)nc2c1nc(Br)n2C1CCCCO1]

N-Bromosuccinimide (0.214 g, 1.2 mmol) was added to a stirred solution of 2-(cyclohexyloxy)-9-(tetrahydro-2H-pyran-2-yl)-9H-purin-6-amine (0.254 g, 0.80 mmol) in chloroform (5 ml) at 0° C. The resultant mixture was stirred at 0° C. for 1.5 hours and then warmed to room temperature and stirred for a further 2 hours. Water (5 ml) was added and the phases separated using a hydrophobic frit. The organic phase was evaporated and the residue dissolved in dichloromethane and purified on a 70 g aminopropyl (NH$_2$) cartridge eluting with a 0-100% ethyl acetate in cyclohexane gradient over 40 mins. The appropriate fractions were combined and evaporated in vacuo to give the title compound as a white solid (0.252 g).

LCMS (System B): $t_{RET}$=2.83 min; MH$^+$=396/398

Intermediate 67: 2-(Cyclohexyloxy)-8-(methyloxy)-9-(tetrahydro-2H-ovran-2-yl)-9H-purin-6-amine

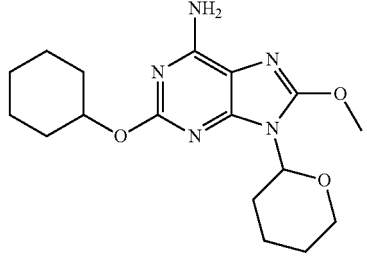 [SMILES: COc1nc2c(N)nc(OC3CCCCC3)nc2n1C1CCCCO1]

Prepared similarly to Intermediate 57 from 8-bromo-2-(cyclohexyloxy)-9-(tetrahydro-2H-pyran-2-yl)-9H-purin-6-amine.

LCMS (System D): $t_{RET}$=2.86 min; MH$^+$=348

Intermediate 68: 2-(Cyclohexlyoxy)-8-(methyloxy)-1H-purin-6-amine trifluoroacetate

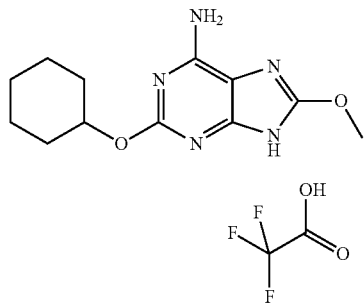 [SMILES: COc1nc2c(N)nc(OC3CCCCC3)nc2[nH]1 ; O=C(O)C(F)(F)F]

Prepared similarly to Intermediate 58 from 2-(cyclohexyloxy)-8-(methyloxy) -9-(tetrahydro-2H-pyran-2-yl)-9H-purin-6-amine.

LCMS (System B): $t_{RET}$=1.43 min; $MH^+$=264

Intermediate 69: 9-(4-Chlorobutyl)-2-(cyclohexyloxy)-8-(methyloxy)-9H-purin-6-amine

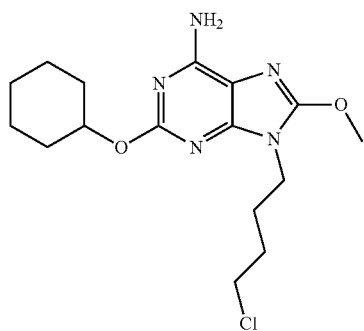 [SMILES: COc1nc2c(N)nc(OC3CCCCC3)nc2n1CCCCCl]

Prepared similarly to Intermediate 44 from 2-(cyclohexyloxy)-8-(methyloxy) -1H-purin-6-amine trifluoroacetate and 1-bromo-4-chlorobutane.

LCMS (System D): $t_{RET}$=3.05 min; $MH^+$=354/356

Intermediate 70: $N^2$-[(1R)-1-Methylbutyl]-9-(tetrahydro-2H-pyran-2-yl)-9H-purine-2,6-diamine

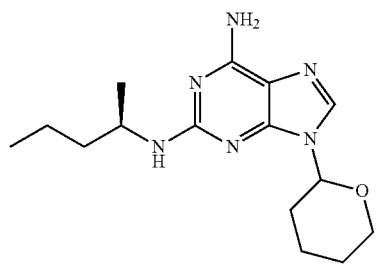

A crude sample of (2R)-2-pentanamine containing dichloromethane (11.12 g containing ca 3.1 g, 35.6 mmol of amine) was added to a suspension of 2-fluoro -9-(tetrahydro-2H-pyran-2-yl)-9H-purin-6-amine (5.00 g, 21.08 mmol) in ethylene glycol (50 ml). The mixture was heated at 110° C. for 20 hours and then cooled to room temperature and partitioned between water (200 ml) and ethyl acetate (200 ml). The organic phase was separated, washed with saturated brine, dried over anhydrous magnesium sulphate, filtered and evaporated. The residue was dissolved in dichloromethane and purified on a 110 g aminopropyl ($NH_2$) cartridge using a 0-100% ethyl acetate-cyclohexane gradient over 40 mins. The appropriate fractions were combined and evaporated in vacuo and the residue triturated with diethyl ether and some insoluble starting material removed by filtration. Evaporation of the ether filtrate afforded the title compound as an off-white foam (2.34 g).

LCMS (System D): $t_{RET}$=2.63 min; $MH^+$=305

Intermediate 71: 8-Bromo-$N^2$-[(1R)-1-methylbutyl]-9-(tetrahydro-2H-pyran-2-yl)-9H-purine-2,6-diamine

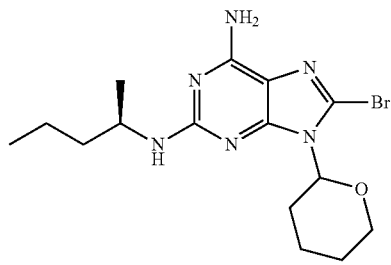 [SMILES: CCC[C@@H](C)Nc1nc(N)c2nc(Br)n(C3CCCCO3)c2n1]

N-Bromosuccinimide (2.08 g, 11.69 mmol) was added portionwise to a stirred solution of $N^2$-[(1R)-1-methylbutyl]-9-(tetrahydro-2H-pyran-2-yl) -9H-purine-2,6-diamine (2.27 g, 7.46 mmol) in chloroform (30 ml) at 0° C. under at atmosphere of nitrogen. The reaction mixture was allowed to stir for 1.5 hours when chloroform (20 ml) and water (50 ml) were added. After mixing the layers were separated using a hydrophobic frit, the aqueous layer was washed with an additional portion of chloroform and the combined organic extracts were evaporated. The residue was dissolved in dichloromethane and purified on a 110 g aminopropyl ($NH_2$) cartridge using a 0-100% ethyl acetate in cyclohexane gradient over 40 mins. The appropriate fractions were combined and evaporated in vacuo to give the title compound as an off-white foam (0.846 g).

LCMS (System D): $t_{RET}$=3.05 min; $MH^+$=383/385

Intermediate 72: $N^2$-[(1R)-1-Methylbutyl]-8-(methyloxy)-9-(tetrahydro-2H-pyran-2-yl)-9H-purine-2,6-diamine

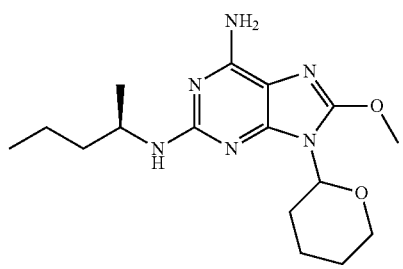 [SMILES: CCC[C@@H](C)Nc1nc(N)c2nc(OC)n(C3CCCCO3)c2n1]

A solution of sodium methoxide in methanol (0.5M, 9 ml, 4.5 mmol) was added to a solution of 8-bromo-N²-[(1R)-1-methylbutyl]-9-(tetrahydro-2H-pyran-2-yl)-9H-purine-2,6-diamine (0.844 g, 2.20 mmol) in methanol (12 ml) and the resulting solution heated under reflux for 23.5 hours. More sodium methoxide in methanol (0.5M, 4.5 ml) was then added and refluxing continued for a further 4 hours. More sodium methoxide in methanol (0.5M, 4.5 ml) was again added and refluxing continued for a further 16.5 hours when LCMS indicated reaction to be complete. The reaction mixture was cooled to room temperature, evaporated and the residue partitioned between ethyl acetate (75 ml) and water (75 ml). The aqueous phase was re-extracted with ethyl acetate (75 ml) and the combined organic phases were washed with saturated brine, dried over anhydrous magnesium sulphate, filtered and evaporated. The residue was dissolved in dichloromethane and purified on a 100 g aminopropyl (NH$_2$) cartridge using a 0-100% ethyl acetate in cyclohexane gradient followed by a 0-20% methanol (+1% triethylamine) gradient over 15 mins. Product-containing fractions were combined and evaporated in vacuo to give the title compound as a white foam (0.614 g).

LCMS (System D): $t_{RET}$=2.83 min; MH⁺=335

Intermediate 73: N²-[(1R)-1-Methylbutyl]-8-(methyloxy)-3H-purine-2,6-diamine trifluoroacetate

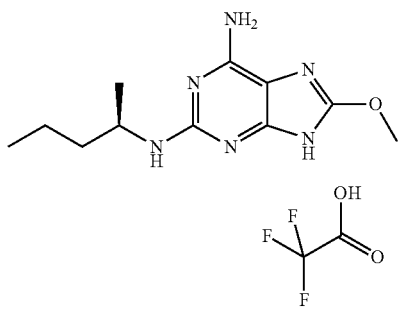 [SMILES: CCC[C@@H](C)Nc1nc(N)c2nc(OC)[nH]c2n1 ; O=C(O)C(F)(F)F]

Trifluoroacetic acid (1 ml, 1.48 g, 7.08 mmol) was added to a stirred solution of N₂-[(1R)-1-methylbutyl]-8-(methyloxy)-9-(tetrahydro-2H-pyran-2-yl)-9H-purine-2,6-diamine (0.613 g, 1.833 mmol) in methanol (10 ml). The resultant mixture was stirred for 66 hours under an atmosphere of nitrogen and then evaporated to give the title compound as an off-white solid (0.690 g).

LCMS (System D): $t_{RET}$=1.89 min; MH⁺=251

Intermediate 74: 9-(4-Chlorobutyl)-N²-[(1R)-1-methylbutyl]-8-(methyloxy)-9H-purine-2 6-diamine

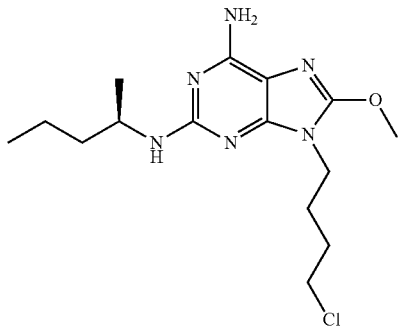 [SMILES: CCC[C@@H](C)Nc1nc(N)c2nc(OC)n(CCCCCl)c2n1]

Prepared similarly to Intermediate 44 from N²-[(1R)-1-methylbutyl]-8-(methyloxy)-3H-purine-2,6-diamine trifluoroacetate and 1-bromo-4-chlorobutane.

LCMS (System D): $t_{RET}$=3.02 min; MH⁺=341/343

Intermediate 75: N²-[(1S)-1-Methylbutyl]-9-(tetrahydro-2H-pyran-2-yl)-9H-purine-2,6-diamine

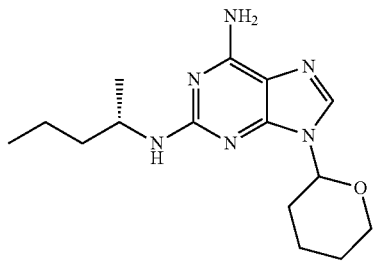 [SMILES: CCC[C@H](C)Nc1nc(N)c2ncn(C3CCCCO3)c2n1]

Prepared similarly to Intermediate 70 from 2-fluoro-9-(tetrahydro-2H-pyran-2-yl)-9H-purin-6-amine and (2S)-2-pentanamine.

LCMS (System D): $t_{RET}$=2.63 min; MH⁺=305

Intermediate 76: 8-Bromo-N²-[(1S)-1-methylbutyl]-9-(tetrahydro-2H-pyran-2-yl)-9H-purine-2,6-diamine

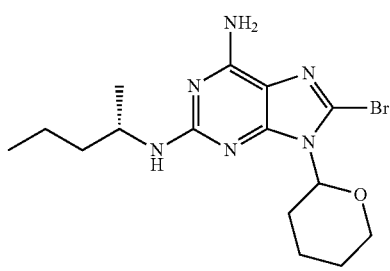 [SMILES: CCC[C@H](C)Nc1nc(N)c2nc(Br)n(C3CCCCO3)c2n1]

Prepared similarly to Intermediate 71 from N²-[(1S)-1-methylbutyl]-9-(tetrahydro-2H-pyran-2-yl)-9H-purine-2,6-diamine.

LCMS (System D): $t_{RET}$=3.05 min; MH⁺=383/385

Intermediate 77: N²-[(1S)-1-Methylbutyl]-8-(methyloxy)-9-(tetrahydro-2H-pyran-2-yl)-9H-purine-2,6-diamine

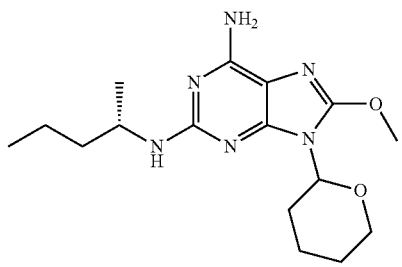 [SMILES: CCC[C@H](C)Nc1nc(N)c2nc(OC)n(C3CCCCO3)c2n1]

A solution of sodium methoxide in methanol (0.5M, 13 ml, 6.5 mmol) was added to a solution of 8-bromo-N²-[(1S)-1-methylbutyl]-9-(tetrahydro-2H-pyran-2-yl)-9H-purine-2,6-diamine (1.26 g, 3.29 mmol) in methanol (10 ml) and the resulting solution heated under reflux for 4 hours. More sodium methoxide in methanol (0.5M, 12 ml, 6 mmol) was then added and refluxing continued for a further 18 hours. The mixture was cooled and evaporated and the residue partitioned between ethyl acetate (75 ml) and water (75 ml). The aqueous phase was re-extracted with ethyl acetate (75 ml) and the combined organic phases were washed with saturated brine, dried over anhydrous magnesium sulphate and evaporated. The residue was dissolved in dichloromethane and purified on a 100 g aminopropyl ($NH_2$) cartridge using a 0-100% ethyl acetate in cyclohexane gradient followed by a 0-20% methanol (+1% triethylamine) gradient over 15 mins. The product-containing fractions were combined and evaporated in vacuo to give the title compound as a white foam (0.848 g).

LCMS (System D): $t_{RET}$=2.83 min; $MH^+$=335

Intermediate 78: $N^2$-[(1S)-1-Methylbutyl]-8-(methyloxy)-3H-purine-2,6-diamine trifluoroacetate

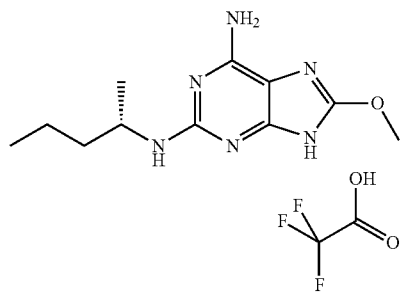

Prepared similarly to Intermediate 73 from $N^2$-[(1S)-1-methylbutyl]-8-(methyloxy)-9-(tetrahydro-2H-pyran-2-yl)-9H-purine-2,6-diamine.

LCMS (System D): $t_{RET}$=1.89 min; $MH^+$=251

Intermediate 79: 9(4-Chlorobutyl)-$N^2$-[(1S)-1-methylbutyl]-8-(methyloxy)-9H-purine-2 6-diamine

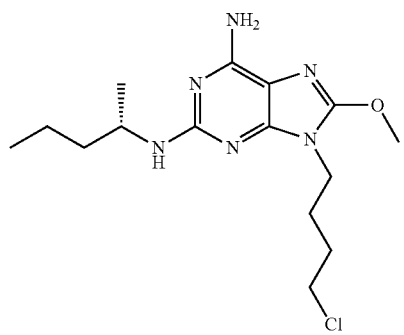 [SMILES: CCC[C@H](C)Nc1nc(N)c2nc(OC)n(CCCCCl)c2n1]

Prepared similarly to Intermediate 44 from $N^2$-[(1S)-1-methylbutyl]-8-(methyloxy)-3H-purine-2,6-diamine trifluoroacetate and 1-bromo-4-chlorobutane.

LCMS (System D): $t_{RET}$=3.02 min; $MH^+$=341/343

Intermediate 80: 9(3-Chloropropyl)-2-{[(1S)-1-methylbutyl]oxy}-8-(methyloxy)-9H-purin-6-amine

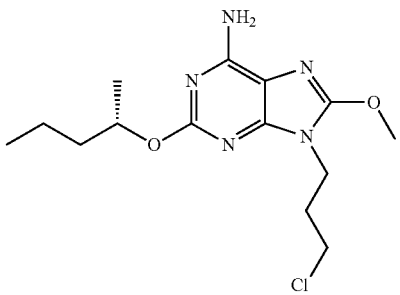 [SMILES: CCC[C@H](C)Oc1nc(N)c2nc(OC)n(CCCCl)c2n1]

Prepared similarly to Intermediate 44 from 2-{[(1S)-1-methylbutyl]oxy}-8-(methyloxy)-9H-purin-6-amine trifluoroacetate and 1-bromo-3-chloropropane.

LCMS (System D): $t_{RET}$=2.90 min; $MH^+$=328/330

Intermediate 81: 9-(5-Chloropentyl)-8-(methyloxy)-2-{[(1S)-1-methylpropyl]oxy}-9H-purin-6-amine

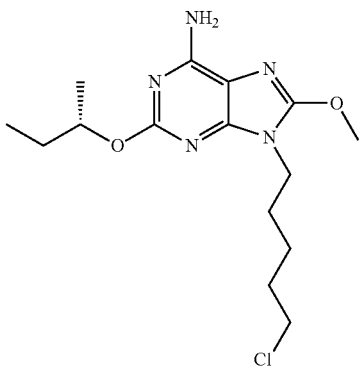 [SMILES: CC[C@H](C)Oc1nc(N)c2nc(OC)n(CCCCCCl)c2n1]

Prepared similarly to Intermediate 14 from 8-(methyloxy)-2-{[(1S)-1-methylpropyl]oxy}-1H-purin-6-amine trifluoroacetate and 1-bromo-5-chloropentane.

LCMS (System A): $t_{RET}$=1.00 min; $MH^+$=342/344

Intermediate 82: 8-(Methyloxy)-2-{[(1S)-1-methylpropyl]oxy}-9-[5-(1-piperidinyl)pentyl]-9H-purin-6-amine

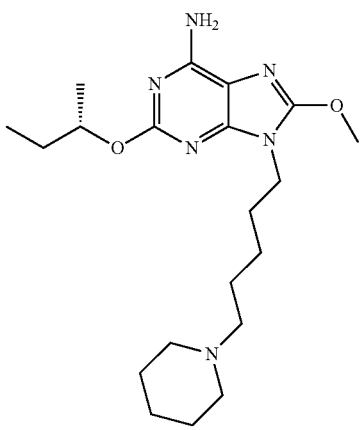 [SMILES: CC[C@H](C)Oc1nc(N)c2nc(OC)n(CCCCCN3CCCCC3)c2n1]

Prepared similarly to Intermediate 38 from 9-(5-chloropentyl)-8-(methyloxy)-2-{[(1S)-1-methylpropyl]oxy}-9H- purin-6-amine and piperidine but with purification on silica using a 0-25% methanol in dichloromethane gradient.

LCMS (System A): $t_{RET}$=0.61 min; MH$^+$=391

Intermediate 83: 2-(Butyloxy)-8-(methyloxy)-9-[3-(1-piperidinyl)propyl]-9H-purin-6-amine, formic acid salt

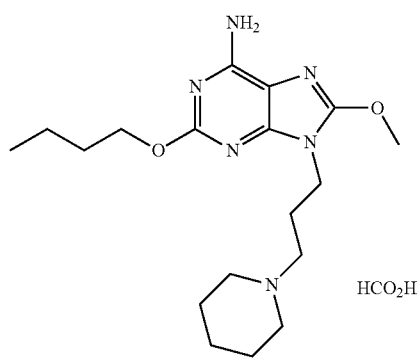 [SMILES: CCCCOc1nc(N)c2nc(OC)n(CCCN3CCCCC3)c2n1 ; "HCO2H"]

Prepared similarly to Intermediate 20 from 2-(butyloxy)-8-(methyloxy)-1H-purin-6-amine trifluoroacetate, 1,3-dibromopropane and piperidine but with sequential purifications by MDAP using Method A followed by Method D.

LCMS (System B): $t_{RET}$=1.16 min; MH$^+$=363

Example 1

6-Amino-9-[3-(1-azetidinyl)propyl]-2-(butyloxy)-7,9-dihydro-8H-purin-8-one

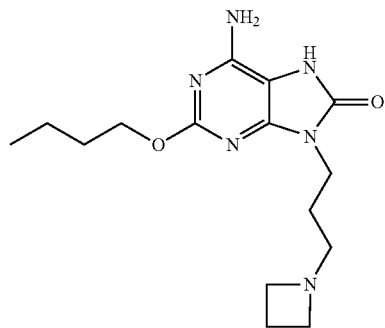 [SMILES: CCCCOc1nc(N)c2[nH]c(=O)n(CCCN3CCC3)c2n1]

9-[3-(1-Azetidinyl)propyl]-2-(butyloxy)-8-(methyloxy)-9H-purin-6-amine (13 mg, 0.039 mmol) was dissolved in methanol (3 ml) and 4M hydrogen chloride in 1,4-dioxane (0.243 ml, 0.972 mmol) was added and the mixture stirred at room temperature for 18 hours. The solvent was removed in vacuo and the residue was dissolved in methanol and loaded onto an aminopropyl SPE cartridge (2 g). The cartridge was eluted with methanol and the solvent removed to give the title compound as a white solid (13 mg).

LCMS (System B): $t_{RET}$=1.12 min; MH$^+$=321

Example 2

6-Amino-2-(butyloxy)-9-[3-(1-pyrrolidinyl)propyl]-7,9-dihydro-8H-purin-8-one

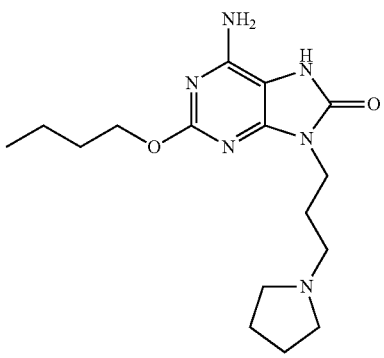 [SMILES: CCCCOc1nc(N)c2[nH]c(=O)n(CCCN3CCCC3)c2n1]

2-(Butyloxy)-8-(methyloxy)-9-[3-(1-pyrrolidinyl)propyl]-9H-purin-6-amine (49 mg, 0.141 mmol) was dissolved in methanol (5 ml) and 4M hydrogen chloride in 1,4-dioxane (0.879 ml, 3.52 mmol) was added and the mixture stirred at room temperature for 5 hours. The solvent was removed in vacuo to give a cream solid which was dissolved in methanol and loaded onto an aminopropyl SPE cartridge (2 g) and eluted with methanol. The solvent was evaporated to give the title compound as a white solid (43 mg).

LCMS (System C): $t_{RET}$=0.70 min; MH$^+$=335

Example 3

6-Amino-2-(butyloxy)-9-[3-(hexahydro-1H-azepin-1-yl)propyl]-7,9-dihydro-8H-purin-8-one

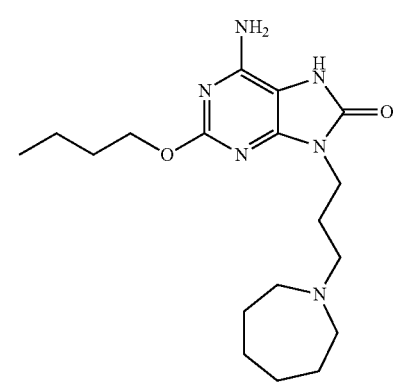 [SMILES: CCCCOc1nc(N)c2[nH]c(=O)n(CCCN3CCCCCC3)c2n1]

Prepared similarly to Example 1 from 2-(butyloxy)-9-[3-(hexahydro-1H-azepin-1-yl)propyl]-8-(methyloxy)-9H-purin-6-amine.

LCMS (System B): $t_{RET}$=1.33 min; MH$^+$=363

Example 4

6-Amino-9-[4-(1-azetidinyl)butyl]-2-(butyloxy)-7,9-dihydro-8H-purin-8-one

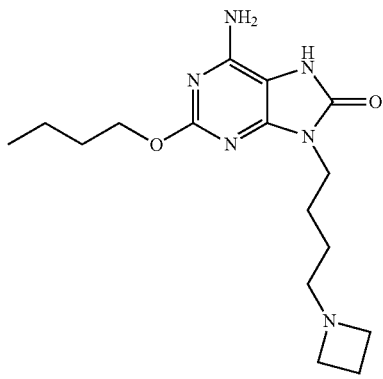 [SMILES: CCCCOc1nc(N)c2[nH]c(=O)n(CCCCN3CCC3)c2n1]

Prepared similarly to Example 1 from 9-[4-(1-azetidinyl)butyl]-2-(butyloxy)-8-(methyloxy)-9H-purin-6-amine.

LCMS (System B): $t_{RET}$=1.16 min; MH$^+$=335

Example 5

6-Amino-2-(butyloxy)-9-[4-(1-pyrrolidinyl)butyl]-7,9-dihydro-8H-purin-8-one

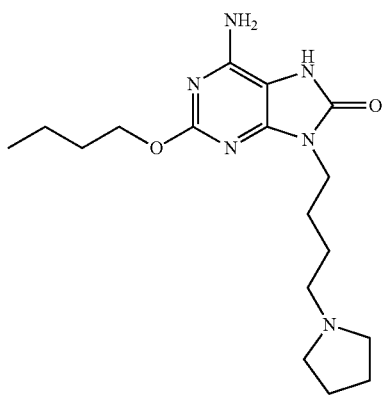 [SMILES: CCCCOc1nc(N)c2[nH]c(=O)n(CCCCN3CCCC3)c2n1]

Prepared similarly to Example 1 from 2-(butyloxy)-8-(methyloxy)-9-[4-(1-pyrrolidinyl)butyl]-9H-purin-6-amine formic acid salt.

LCMS (System B): $t_{RET}$=1.23 min; MH$^+$=349

Example 6

6-Amino-2-(butyloxy)-9-[4-(1-piperidinyl)butyl]-7,9-dihydro-8H-purin-8-one

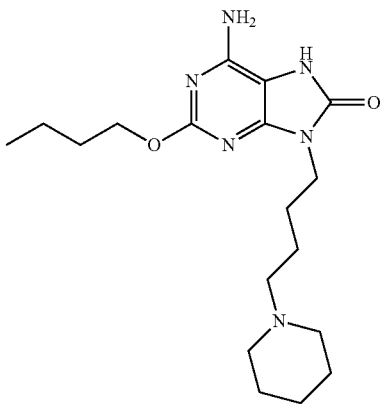 [SMILES: CCCCOc1nc(N)c2[nH]c(=O)n(CCCCN3CCCCC3)c2n1]

Prepared similarly to Example 1 from 2-(butyloxy)-8-(methyloxy)-9-[4-(1-piperidinyl)butyl]-9H-purin-6-amine formic acid salt.

LCMS (System B): $t_{RET}$=1.29 min; MH$^+$=363

Example 7

6-Amino-2-(butyloxy)-9-[4-(hexahydro-1H-azepin-1-yl)butyl]-7,9-dihydro-8H-purin-8-one

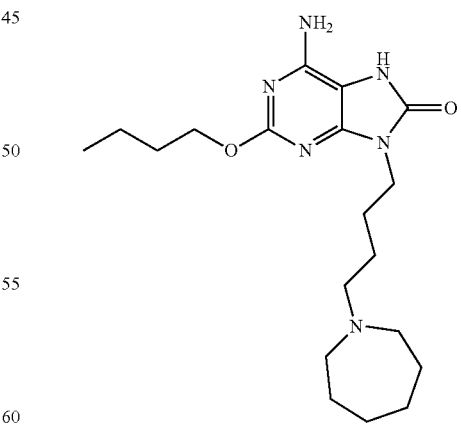

Prepared similarly to Example 1 from 2-(butyloxy)-9-[4-(hexahydro-1H-azepin-1-yl)butyl]-8-(methyloxy)-9H-purin-6-amine.

LCMS (System B): $t_{RET}$=1.37 min; MH$^+$=377

Example 8

6-Amino-9-[5-(1-azetidinyl)pentyl]-2-(butyloxy)-7,9-dihydro-8H-purin-8-one

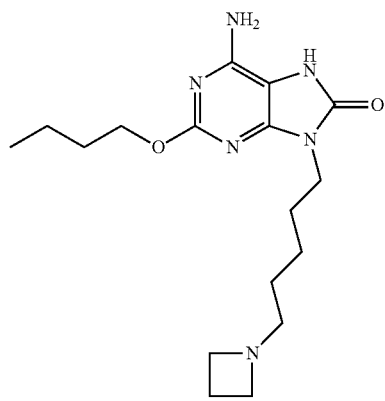 [SMILES: CCCCOc1nc(N)c2[nH]c(=O)n(CCCCCN3CCC3)c2n1]

Prepared similarly to Example 1 from 9-[5-(1-azetidinyl)pentyl]-2-(butyloxy)-8-(methyloxy)-9H-purin-6-amine.

LCMS (System B): $t_{RET}$=1.25 min; MH$^+$=349

Example 9

6-Amino-2-(butyloxy)-9-[5-(1-pyrrolidinyl)pentyl]-7,9-dihydro-8H-purin-8-one

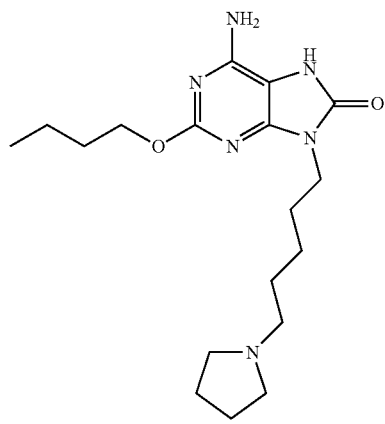 [SMILES: CCCCOc1nc(N)c2[nH]c(=O)n(CCCCCN3CCCC3)c2n1]

Prepared similarly to Example 1 from 2-(butyloxy)-8-(methyloxy)-9-[5-(1-pyrrolidinyl)pentyl]-9H-purin-6-amine.

LCMS (System B): $t_{RET}$=1.28 min; MH$^+$=363

Example 10

6-Amino-2-(butyloxy)-9-[5-(1-piperidinyl)pentyl]-7,9-dihydro-8H-purin-8-one

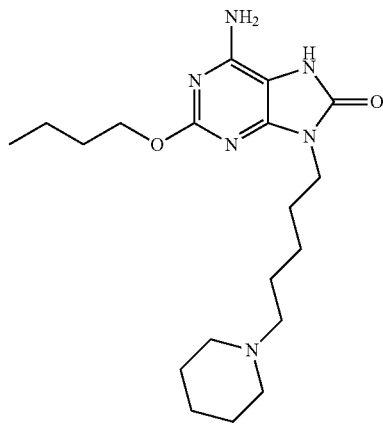 [SMILES: CCCCOc1nc(N)c2[nH]c(=O)n(CCCCCN3CCCCC3)c2n1]

Prepared similarly to Example 1 from 2-(butyloxy)-8-(methyloxy)-9-[5-(1-piperidinyl)pentyl]-9H-purin-6-amine.

LCMS (System B): $t_{RET}$=1.35 min; MH$^+$=377

Example 11

6-Amino-2-(butyloxy)-9-[5-(hexahydro-1H-azepin-1-yl)pentyl]-7,9-dihydro-8H-purin-8-one

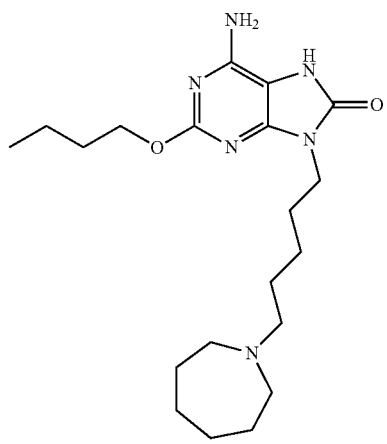 [SMILES: CCCCOc1nc(N)c2[nH]c(=O)n(CCCCCN3CCCCCC3)c2n1]

Method A

Prepared similarly to Example 2 from 2-(butyloxy)-9-[5-(hexahydro-1H-azepin-1-yl)pentyl]-8-(methyloxy)-9H-purin-6-amine.

LCMS (System B): $t_{RET}$=1.55 min; MH$^+$=391

Method B

Prepared similarly to Example 19 from 2-(butyloxy)-8-(methyloxy)-1H-purin-6-amine trifluoroacetate, 1-bromo-5-chloropentane and hexahydro-1H-azepine.

LCMS (System B): $t_{RET}$=1.54 min; MH$^+$=391

Example 12

6-Amino-2-(butyloxy)-9-[5-(hexahydro-1(2H)-azocinyl)pentyl]-7,9-dihydro-8H-purin-8-one

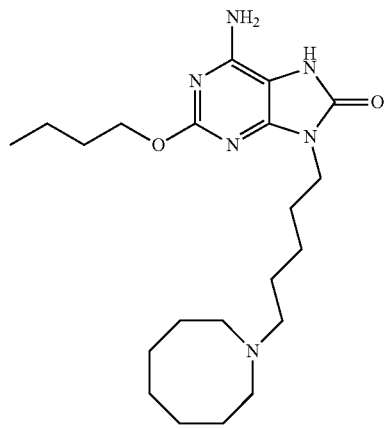 [SMILES: CCCCOc1nc(N)c2[nH]c(=O)n(CCCCCN3CCCCCCC3)c2n1]

Prepared similarly to Example 1 from 2-(butyloxy)-9-[5-(hexahydro-1(2H)-azocinyl)pentyl]-8-(methyloxy)-9H-purin-6-amine.

LCMS (System D): $t_{RET}$=3.17 min; MH$^+$=405

Example 13

6-Amino-2-(butyloxy)-9-[6-(1-pyrrolidinyl)hexyl]-7,9-dihydro-8H-purin-8-one

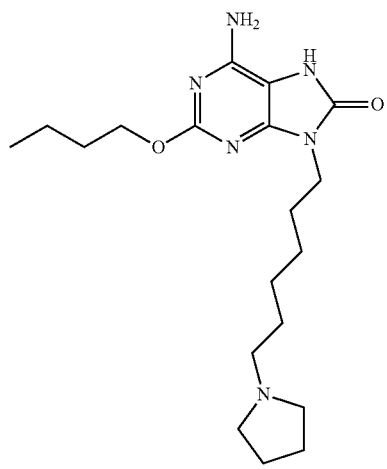 [SMILES: CCCCOc1nc(N)c2[nH]c(=O)n(CCCCCCN3CCCC3)c2n1]

Prepared similarly to Example 1 from 2-(butyloxy)-8-(methyloxy)-9-[6-(1-pyrrolidinyl)hexyl]-9H-purin-6-amine.

LCMS (System D): $t_{RET}$=2.47 min; MH$^+$=377

Example 14

6-Amino-2-(butyloxy)-9-[6-(1-piperidinyl)hexyl]-7,9-dihydro-8H-purin-8-one

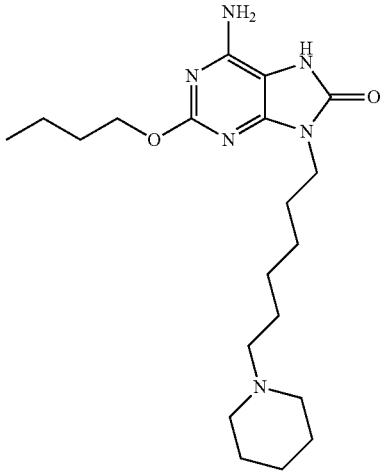 [SMILES: CCCCOc1nc(N)c2[nH]c(=O)n(CCCCCCN3CCCCC3)c2n1]

Prepared similarly to Example 1 from 2-(butyloxy)-8-(methyloxy)-9-[6-(1-piperidinyl)hexyl]-9H-purin-6-amine.

LCMS (System D): $t_{RET}$=2.68 min; MH$^+$=391

Example 15

6-Amino-2-(butyloxy)-9-[6-(hexahydro-1H-azepin-1-yl)hexyl]-7,9-dihydro-8H-purin-8-one

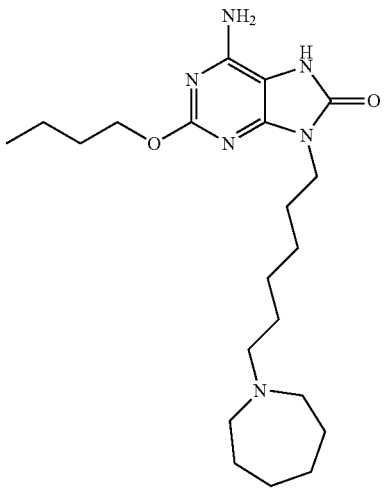 [SMILES: CCCCOc1nc(N)c2[nH]c(=O)n(CCCCCCN3CCCCCC3)c2n1]

Prepared similarly to Example 1 from 2-(butyloxy)-9-[6-(hexahydro-1H-azepin-1-yl)hexyl]-8-(methyloxy)-9H-purin-6-amine.

LCMS (System D): $t_{RET}$=2.76 min; MH$^+$=405

Example 16

6-Amino-2-(butylamino)-9-[3-(1-piperidinyl)propyl]-7,9-dihydro-8H-purin-8-one

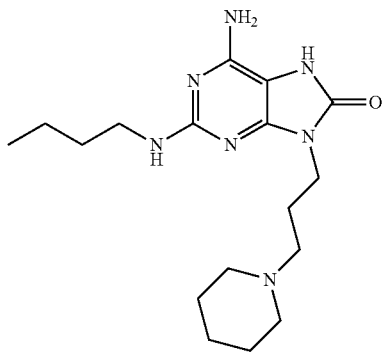 [SMILES: CCCCNc1nc(N)c2[nH]c(=O)n(CCCN3CCCCC3)c2n1]

A mixture of N²-butyl-9-(3-chloropropyl)-8-(methyloxy)-9H-purine-2,6-diamine (250 mg, 0.8 mmole), piperidine (340 mg, 4 mmole) and sodium iodide (360 mg, 2,4 mmole) in THF (8 ml) was heated under reflux for 48 hours. The solvent was evaporated and the residue purified by preparative TLC then dissolved in methanol (5 ml). Hydrogen chloride in methanol (0.5 ml) was added and the mixture stirred at room temperature for 16 hours. The solvent was then evaporated and the pH of the residue was adjusted to 7-8 by addition of sodium bicarbonate solution. The product was extracted into ethyl acetate and the extract was evaporated and the residue purified by preparative HPLC to give the title compound (16 mg).

LCMS (System A): $t_{RET}$=0.55 min; MH⁺=348

Example 17

6-Amino-2-(butylamino)-9-[4-(1-piperidinyl)butyl]-7,9-dihydro-8H-purin-8-one

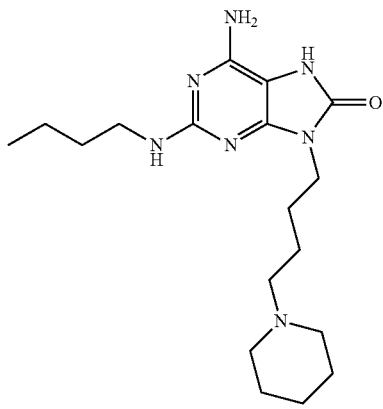 [SMILES: CCCCNc1nc(N)c2[nH]c(=O)n(CCCCN3CCCCC3)c2n1]

Prepared similarly to Example 1 from N²-butyl-8-(methyloxy)-9-[4-(1-piperidinyl)butyl]-9H-purine-2,6-diamine.

LCMS (System B): $t_{RET}$=0.96 min; MH⁺=362

Example 18

6-Amino-2-(butylamino)-9-[4-(hexahydro-1H-azepin-1-yl)butyl]-7,9-dihydro-8H-purin-8-one

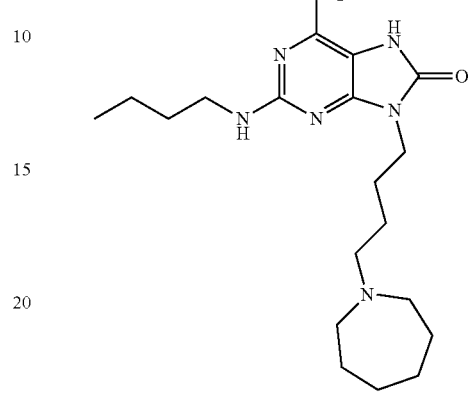

Prepared similarly to Example 1 from N²-butyl-9-[4-(hexahydro-1H-azepin-1-yl)butyl]-8-(methyloxy)-9H-purine-2,6-diamine.

LCMS (System B): $t_{RET}$=1.12 min; MH⁺=376

Example 19

6-Amino-2-(butylamino)-9-[5-(hexahydro-1H-azepin-1-yl)pentyl]-7,9-dihydro-8H-purin-8-one

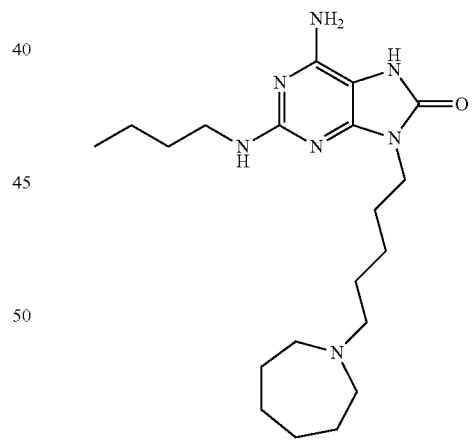

N²-Butyl-8-(methyloxy)-3H-purine-2,6-diamine trifluoroacetate (192 mg, 0.547 mmol) and potassium carbonate (189 mg, 1.368 mmol) were suspended in DMF (3 ml) and heated to 60° C. for 1 hour. The reaction mixture was cooled to room temperature and 1-bromo-5-chloropentane (0.072 ml, 0.547 mmol) was added and the reaction stirred for a further 18 hours. Hexahydro-1H-azepine (54.2 mg, 0.547 mmol) and triethylamine (0.076 ml, 0.547 mmol) were added and the reaction mixture heated to 70° C. for 24 hours. LCMS showed a major peak with MH⁺ 404 consistent with the formation of N²-butyl-9-[5-(hexahydro-1H-azepin-1-yl)pentyl]-8-(methyloxy)-9H-purine-2,6-diamine. The solvent was removed in vacuo and the residue partitioned between DCM (2 ml) and water (2 ml). The aqueous was extracted again with DCM (2 ml) and the combined organic extracts were concentrated and the residue was dissolved in 1:1 MeOH:DMSO (2 ml) and purified by MDAP (Method C). Evaporation of the product containing fractions gave a residual TFA salt which LCMS indicated had undergone hydrolysis of the 8-methoxy group, presumably on concentration in the presence of TFA. This crude material was dissolved once more in 1:1 MeOH:DMSO (2 ml) and re-purified by MDAP (Method A). Product-containing fractions were evaporated under a stream of nitrogen to give the title compound as a white solid (39 mg).

LCMS (System B): $t_{RET}$=1.18 min; MH$^+$=390

Example 20

6-Amino-2-{[(1S)-1-methylbutyl]oxy}-9-[4-(1-piperidinyl)butyl]-7,9-dihydro-8H-purin-8-one

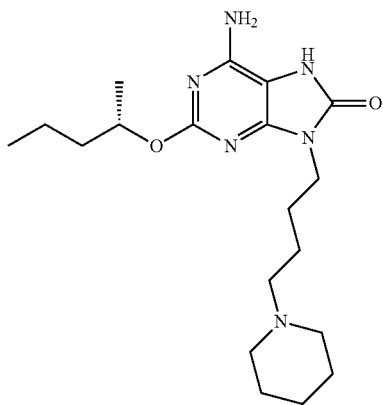 [SMILES: CCC[C@H](C)Oc1nc(N)c2[nH]c(=O)n(CCCCN3CCCCC3)c2n1]

Prepared similarly to Example 19 from 2-{[(1S)-1-methylbutyl]oxy}-8-(methyloxy)-1H-purin-6-amine trifluoroacetate, 1-bromo-4-chlorobutane and piperidine.

LCMS (System B): $t_{RET}$=1.38 min; MH$^+$=377

Example 21

6-Amino-9-[4-(hexahydro-1H-azepin-1-yl)butyl]-2-{[(1S)-1-methylbutyl]oxy}-7,9-dihydro-8H-purin-8-one

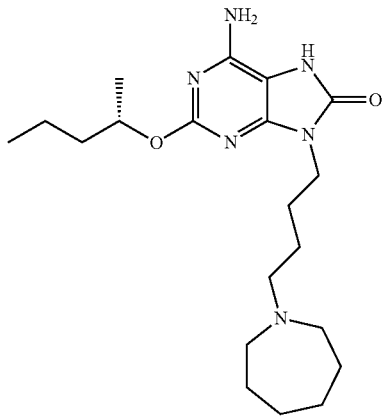 [SMILES: CCC[C@H](C)Oc1nc(N)c2[nH]c(=O)n(CCCCN3CCCCCC3)c2n1]

Prepared similarly to Example 1 from 9-[4-(hexahydro-1H-azepin-1-yl)butyl]-2-{[(1S)-1-methylbutyl]oxy}-8-(methyloxy)-9H-purin-6-amine.

LCMS (System B): $t_{RET}$=1.48 min; MH$^+$=391

Example 22

6-Amino-2-{[(1S)-1-methylbutyl]oxy}-9-[5-(1-piperidinyl)pentyl]-7,9-dihydro-8H-purin-8-one

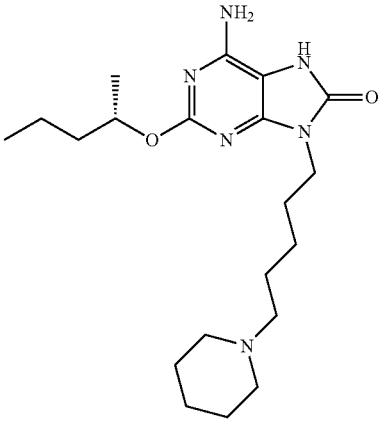 [SMILES: CCC[C@H](C)Oc1nc(N)c2[nH]c(=O)n(CCCCCN3CCCCC3)c2n1]

Prepared similarly to Example 1 from 2-{[(1S)-1-Methylbutyl]oxy}-8-(methyloxy)-9-[5-(1-piperidinyl)pentyl]-9H-purin-6-amine as follows:

A solution of hydrogen chloride in dioxane (4M, 0.71 ml) was added to a solution of 2-{[(1S)-1-methylbutyl]oxy}-8-(methyloxy)-9-[5-(1-piperidinyl)pentyl]-9H-purin-6-amine (0.046 g, 0.126 mmol) in methanol (3 ml). The resultant mixture was allowed to stand overnight at room temperature and then blown down under nitrogen. The residue was dissolved in methanol and loaded onto a 2 g aminopropyl SPE cartridge (pre-conditioned with methanol), eluted with methanol and the resultant solution blown down under nitrogen to give the title compound as a yellow solid (40.97 mg).

LCMS (System D): $t_{RET}$=2.70 min; MH$^+$=391

A similarly prepared sample (1.7 g) was recrystallised from ethyl acetate (ca 50 ml). The crystals were collected, washed with ice-cold ethyl acetate (15 ml) and dried in vacuo at 50° C. for 3 hours to give the title compound as a cream crystalline solid (1.33 g).

Melting point onset (DSC): 207.4° C. (see FIG. 2)

XRPD: (see FIG. 1 and Table 1)

Example 23

6-Amino-9-[5-(hexahydro-1H-azepin-1-yl)pentyl]-2-{[(1S)-1-methylbutyl]oxy}-7,9-dihydro-8H-purin-8-one

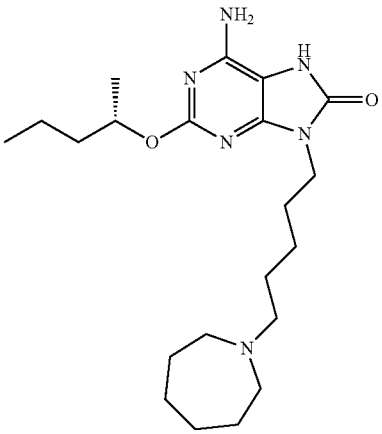 [SMILES: CCC[C@H](C)Oc1nc(N)c2[nH]c(=O)n(CCCCCN3CCCCCC3)c2n1]

Prepared similarly to Example 19 from 2-{[(1S)-1-methylbutyl]oxy}-8-(methyloxy)-1H-purin-6-amine trifluoroacetate, 1-bromo-5-chloropentane and hexahydro-1H-azepine.
LCMS (System B): $t_{RET}$=1.54 min; MH$^+$=405

Example 24

6-Amino-2-{[(1S)-1-methylpropyl]oxy}-9-[4-(1-piperidinyl)butyl]-7,9-dihydro-8H-purin-8-one

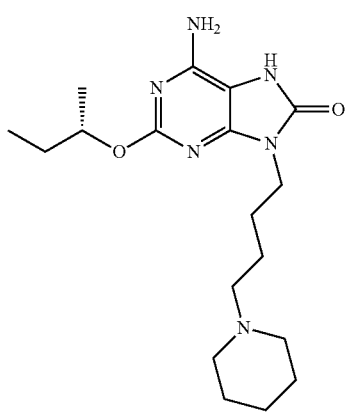 [SMILES: CC[C@H](C)Oc1nc(N)c2[nH]c(=O)n(CCCCN3CCCCC3)c2n1]

Prepared similarly to Example 29 from 9-(4-chlorobutyl)-8-(methyloxy)-2-{[(1S)-1-methylpropyl]oxy}-9H-purin-6-amine and piperidine.
LCMS (System D): $t_{RET}$=2.27 min; MH$^+$=363
A sample of the intermediate 8-methoxy derivative 8-(methyloxy)-2-{[(1S)-1-methylpropyl]oxy}-9-[4-(1-piperidinyl)butyl]-9H-purin-6-amine was also isolated.
LCMS (System D): $t_{RET}$=2.56 min; MH$^+$=377

Example 25

6-Amino-2-{[(1S)-1-methylpentyl]oxy}-9-[4-(1-piperidinyl)butyl]-7,9-dihydro-8H-purin-8-one

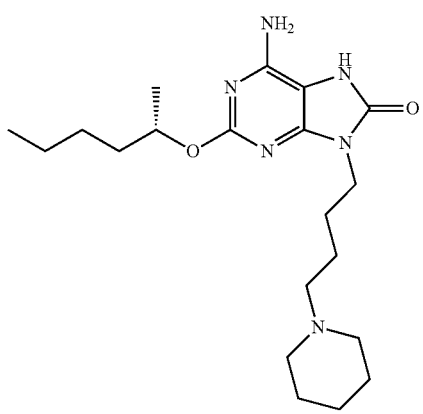 [SMILES: CCCC[C@H](C)Oc1nc(N)c2[nH]c(=O)n(CCCCN3CCCCC3)c2n1]

Prepared similarly to Example 29 from 9-(4-chlorobutyl)-8-(methyloxy) -2-{[(1S)-1-methylpentyl]oxy}-9H-purin-6-amine and piperidine.
LCMS (System D): $t_{RET}$=2.72 min; MH$^+$=391
A sample of the intermediate 8-methoxy derivative 8-(methyloxy)-2-{[(1S)-1-methylpentyl]oxy}-9-[4-(1-piperidinyl)butyl]-9H-purin-6-amine was also isolated.
LCMS (System D): $t_{RET}$=3.01 min; MH$^+$=405

Example 26

6-Amino-2-[(1-methylethyl)oxy]-9-[5-(1-piperidinyl)pentyl]-7,9-dihydro-8H-purin-8-one

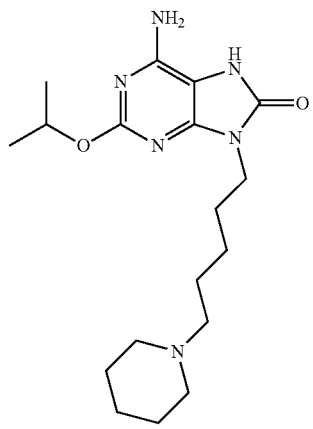 [SMILES: CC(C)Oc1nc(N)c2[nH]c(=O)n(CCCCCN3CCCCC3)c2n1]

Prepared similarly to Example 29 from 9-(5-chloropentyl)-2-[(1-methylethyl)oxy]-8-(methyloxy)-9H-purin-6-amine and piperidine.
LCMS (System D): $t_{RET}$=2.18 min; MH$^+$=363
A sample of the intermediate 8-methoxy derivative 2-[(1-methylethyl)oxy]-8-(methyloxy)-9-[5-(1-piperidinyl)pentyl]-9H-purin-6-amine was also isolated.
LCMS (System D): $t_{RET}$=2.43 min; MH$^+$=377

Example 27

6-Amino-2-(cyclobutyloxy)-9-[4-(1-piperidinyl)butyl]-7,9-dihydro-8H-purin-8-one

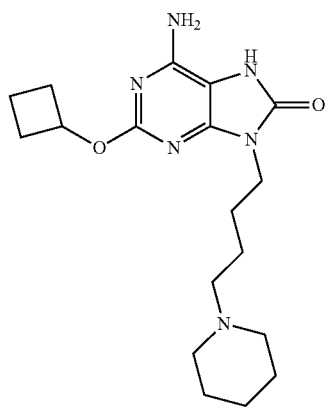 [SMILES: Nc1nc(OC2CCC2)nc2c1[nH]c(=O)n2CCCCN1CCCCC1]

Prepared similarly to Example 29 from 9-(4-chlorobutyl)-2-(cyclobutyloxy)-8-(methyloxy)-9H-purin-6-amine and piperidine.
LCMS (System D): $t_{RET}$=2.24 min; MH$^+$=361
A sample of the intermediate 8-methoxy derivative 2-(cyclobutyloxy)-8-(methyloxy)-9-[4-(1-piperidinyl)butyl]-9H-purin-6-amine was also isolated.
LCMS (System D): $t_{RET}$=2.49 min; MH$^+$=375

Example 28

6-Amino-2-(cyclopentyloxy)-9-[4-(1-piperidinyl)butyl]-7,9-dihydro-8H-purin-8-one

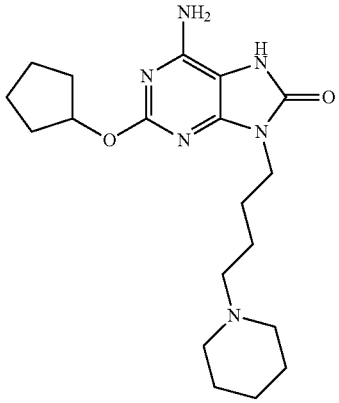 [SMILES: Nc1nc(OC2CCCC2)nc2c1[nH]c(=O)n2CCCCN1CCCCC1]

Prepared similarly to Example 29 from 9-(4-chlorobutyl)-2-(cyclopentyloxy)-8-(methyloxy)-9H-purin-6-amine and piperidine.

LCMS (System D): $t_{RET}$=2.38 min; MH$^+$=375

A sample of the intermediate 8-methoxy derivative 2-(cyclopentyloxy)-8-(methyloxy)-9-[4-(1-piperidinyl)butyl]-9H-purin-6-amine was also isolated.

LCMS (System D): $t_{RET}$=2.64 min; MH$^+$=389

Example 29

6-Amino-2-(cyclohexyloxy)-9-[4-(1-piperidinyl)butyl]-7,9-dihydro-8H-purin-8-one

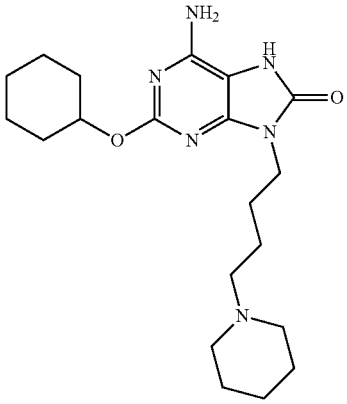 [SMILES: Nc1nc(OC2CCCCC2)nc2c1[nH]c(=O)n2CCCCN1CCCCC1]

Sodium iodide (0.006 g, 0.04 mmol) was added to a stirred mixture of 9-(4-chlorobutyl)-2-(cyclohexyloxy)-8-(methyloxy)-9H-purin-6-amine (0.103 g, 0.303 mmol), N,N-diisopropylethylamine (0.105 ml, 0.079 g, 0.609 mmol) and piperidine (0.120 ml, 0.103 g, 1.215 mmol) in DMF (1.5 ml). The resultant mixture was heated at 80° C. for 20 hours when LCMS showed the formation of two products, one corresponding to displacement of the chloride by piperidine and the second corresponding to concomitant hydrolysis of the 8-methoxy moiety. The reaction mixture was partitioned between dichloromethane (6 ml) and water (6 ml) and the phases separated using a hydrophobic frit. The solvent was removed from the organic phase under a stream of nitrogen in a blow-down unit and the residue was dissolved in 1:1 MeOH:DMSO (2 ml) and separated by mass directed autopreparation (Method A) to afford the title compound as a white solid (16.6 mg).

LCMS (System D): $t_{RET}$=2.53 min; MH$^+$=389

The intermediate 2-(cyclohexyloxy)-8-(methyloxy)-9-[4-(1-piperidinyl)butyl]-9H-purin-6-amine was also isolated as a colourless solid (55.2 mg).

LCMS (System D): $t_{RET}$=2.80 min; MH$^+$=403

Example 30

6-Amino-2-{[(1R)-1-methylbutyl]amino}-9-[4-(1-piperidinyl)butyl]-7,9-dihydro-8H-purin-8-one

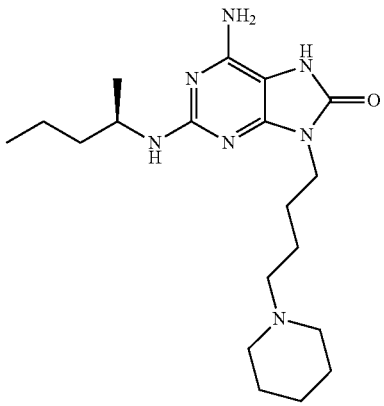 [SMILES: CCC[C@@H](C)Nc1nc(N)c2[nH]c(=O)n(CCCCN3CCCCC3)c2n1]

Prepared similarly to Example 29 from 9-(4-chlorobutyl)-N$^2$-[(1R)-1-methylbutyl]-8-(methyloxy)-9H-purine-2,6-diamine and piperidine.

LCMS (System D): $t_{RET}$=2.47 min; MH$^+$=376

A sample of the intermediate 8-methoxy derivative N$^2$-[(1R)-1-methylbutyl]-8-(methyloxy)-9-[4-(1-piperidinyl)butyl]-9H-purine-2,6-diamine was also isolated.

LCMS (System D): $t_{RET}$=2.76 min; MH$^+$=390

Example 31

6-Amino-2-{[(1S)-1-methylbutyl]amino}-9-[4-(1-piperidinyl)butyl]-7,9-dihydro-8H-purin-8-one

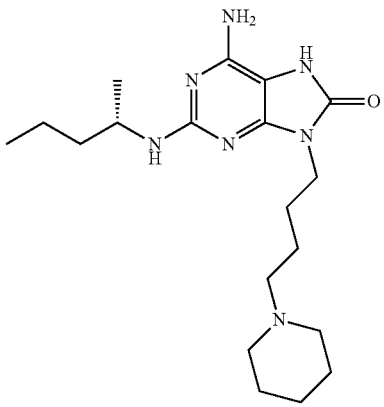

Prepared similarly to Example 29 from 9-(4-chlorobutyl)-N$^2$-[(1S)-1-methylbutyl]-8-(methyloxy)-9H-purine-2,6-diamine and piperidine.

LCMS (System D): $t_{RET}$=2.47 min; MH$^+$=376

A sample of the intermediate 8-methoxy derivative N$^2$-[(1S)-1-methylbutyl]-8-(methyloxy)-9-[4-(1-piperidinyl)butyl]-9H-purine-2,6-diamine was also isolated.

LCMS (System D): $t_{RET}$=2.76 min; MH$^+$=390

Example 32

6-Amino-2-{[(1S)-1-methylbutyl]oxy}-9-[3-(1-piperidinyl)propyl]-7,9-dihydro-8H-purin-8-one

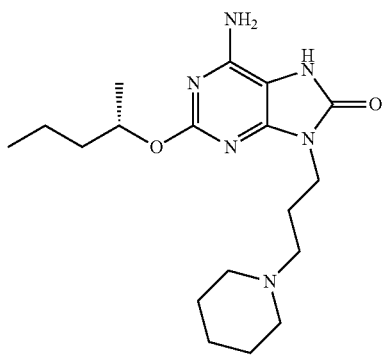 [SMILES: CCC[C@H](C)Oc1nc(N)c2[nH]c(=O)n(CCCN3CCCCC3)c2n1]

Prepared similarly to Example 29 from 9-(3-chloropropyl)-2-{[(1S)-1-methylbutyl]oxy}-8-(methyloxy)-9H-purin-6-amine and piperidine.

LCMS (System D): $t_{RET}$=2.52 min; MH$^+$=363

A sample of the intermediate 8-methoxy derivative 2-{[(1S)-1-methylbutyl]oxy}-8-(methyloxy)-9-[3-(1-piperidinyl)propyl]-9H-purin-6-amine was also isolated.

LCMS (System D): $t_{RET}$=2.87 min; MH$^+$=377

Example 33

6-Amino-2-{[(1S)-1-methylpropyl]oxy}-9-[5-(1-piperidinyl)pentyl]-7,9-dihydro-8H-purin-8-one

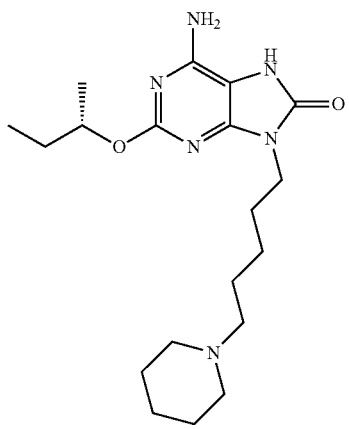 [SMILES: CC[C@H](C)Oc1nc(N)c2[nH]c(=O)n(CCCCCN3CCCCC3)c2n1]

Prepared similarly to Example 1 from 8-(methyloxy)-2-{[(1S)-1-methylpropyl]oxy}-9-[5-(1-piperidinyl)pentyl]-9H-purin-6-amine.

LCMS (System D): $t_{RET}$=2.39 min; MH$^+$=377

Example 34

6-Amino-2-(butyloxy)-9-[3-(1-piperidinyl)propyl]-7,9-dihydro-8H-purin-8-one

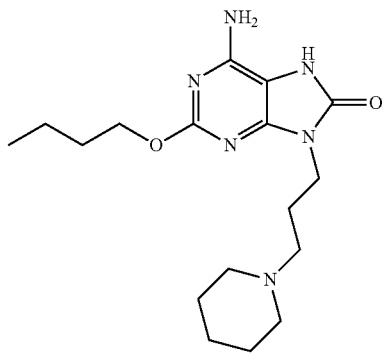 [SMILES: CCCCOc1nc(N)c2[nH]c(=O)n(CCCN3CCCCC3)c2n1]

Prepared similarly to Example 1 from 2-(butyloxy)-8-(methyloxy)-9-[3-(1-piperidinyl)propyl]-9H-purin-6-amine.

LCMS (System B): $t_{RET}$=1.23 min; MH$^+$=349

Polymorphism

X-ray powder diffraction (XRPD) and differential scanning calorimetry (DSC) were performed on 6-amino-2-{[(1S)-1-methylbutyl]oxy}-9-[5-(1-piperidinyl)pentyl]-7,9-dihydro-8H-purin-8-one according to the following methods.

XRPD

XRPD data were acquired on a PANalytical X'Pert Pro powder diffractometer, equipped with an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ. The time per step was 31.750 s. The sample was prepared by mounting a few milligrams of sample on a Si wafer (zero background) plate, resulting in a thin layer of powder.

Characteristic peak positions and calculated d-spacings are summarised in Table 1. These were calculated from the raw data using Highscore software. The experimental error in the peak positions is approximately ±0.1° 2θ. Relative peak intensities will vary due to preferred orientation.

TABLE 1

Characteristic XRPD Peak Positions for Solid-state Form 1 of 6-Amino-2-{[(1S)-1-methylbutyl]oxy}-9-[5-(1-piperidinyl)pentyl]-7,9-dihydro-8H-purin-8-one Form 1

| 2θ/° | d-spacing/Å |
|---|---|
| 5.0 | 17.6 |
| 10.0 | 8.8 |
| 12.7 | 7.0 |
| 13.5 | 6.5 |
| 13.8 | 6.4 |
| 16.6 | 5.3 |
| 18.9 | 4.7 |
| 20.0 | 4.4 |
| 22.2 | 4.0 |
| 23.3 | 3.8 |
| 24.2 | 3.7 |
| 26.1 | 3.4 |

A representative XRPD diffractogram of 6-amino-2-{[(1S)-1-methylbutyl]oxy}-9-[5-(1-piperidinyl)pentyl]-7,9-dihydro-8H-purin-8-one is shown in FIG. 1.

DSC

The DSC thermogram was obtained using a TA Instruments calorimeter. The sample was weighed into an aluminium pan, a pan lid placed on top and lightly crimped without sealing the pan. The experiment was conducted using a heating rate of $10°$ C. $min^{-1}$.

A representative DSC thermogram of 6-amino-2-{[(1S)-1-methylbutyl]oxy}-9-[5-(1-piperidinyl)pentyl]-7,9-dihydro-8H-purin-8-one is shown in FIG. 2.

Biological Data

Compounds of the invention were tested for in vitro biological activity in accordance with the following assays, or similar assays:

Assay for the Induction of Interferon-α using Cryopreserved Human Peripheral Blood Mononuclear Cells (PBMCs)

Compound Preparation

Compounds were dissolved in DMSO. Serial 2-fold dilutions with DMSO were prepared and 0.25 µl dispensed into 384-well clear Greiner polypropylene plates.

Preparation of PBMCs

Blood samples of up to 200 ml were obtained from healthy human donors. Whole blood in 25 ml volumes was overlaid onto 15 ml Ficoll gradients in Leucosep tubes, and centrifuged at 1000 g for 20 min. Cells in the band at the plasma/histopaque interface were carefully removed and washed twice with PBS (centrifuged at 400 g for 5 min to harvest). The final pellet was resuspended in freezing medium (90% Heat-inactivated serum, 10% DMSO) to a cell concentration of $4 \times 10^7$ cells/ml. The resuspended cells were then cryopreserved (frozen) using a rate controlled freezer, and stored at $-140°$ C. for up to 4 months.

Incubation and Assay for Interferon-α

Immediately prior to assay, vials of cryopreserved (frozen) PBMCs were thawed rapidly in a water bath at $37°$ C. A 1:10 dilution of the cells in trypan blue was prepared and counted. The PBMCs were then diluted in growth media [RPMI 1640 containing 10% fetal calf serum (invitrogen), Penicillin+Streptavidin (Gibco cat. # 25030-024, 1:50), L-Glutamine 2 mM, and 1000 units/ml recombinant human IFN-gamma (Preprotech catalogue #300-02)] to a density of $1 \times 10^6$ cells/ml, and 50 ul/well dispensed to 384-well clear Greiner polypropylene plates containing 0.25 µl DMSO or test compound in 0.25 µl DMSO. Top final concentration of compound was typically 50 uM or 5 uM (to obtain curve fit for highly active compounds). Plates were incubated for 24 h at $37°$ C. in 5% $CO_2$.

A multi-isoform immunoassay was used to quantify IFN-α in PBMC supernatants. Rabbit polyclonal antibody against human IFN-α (catalogue number 31101, Stratech Scientific) was diluted 1:10000 in assay buffer (RPMI 1640 containing 10% fetal calf serum, Invitrogen) and 20 µl was added to each well of an MSD (Meso-Scale Discovery) single small-spot 384-well GAR (goat anti-rabbit antibody coated) plate. The plate was incubated for 1 h at room temperature with vigorous shaking. Following three washes with PBS, 20 µl of cell supernatant were added to each well of the plate. The plate was then incubated for 1 h at room temperature with vigorous shaking. A pair of monoclonal antibodies to IFN-α (catalogue numbers 21100 and 21112, Stratech Scientific) were labelled with sulfo-TAG (MSD), diluted 1:1000 in assay buffer and 20 µl added to each well of the plate. The plate was further incubated for 1 h at room temperature with vigorous shaking. Following three washes with PBS, 30 µl of x2 T buffer (MSD) was added to each well and the plate was read on an MSD Sector 6000 plate reader.

Data were normalised to internal plate controls of 1 uM resiquimod (n=16) and DMSO (n=16). pEC50 values were derived by 4-parameter curve fit with IRLS in ActivityBase, from 11-point, two-fold serial dilution of test compounds.

Results

Examples 1 to 34 had a mean $pEC_{50}$ of >5.5.

Assay for the Induction of Interferon-α and TNF-α using Fresh Human Peripheral Blood Mononuclear Cells (PBMCs)

Compound Preparation

Compounds were dissolved and serially diluted in DMSO to give 100× the required concentration range using a Biomek 2000. 1 ul of test compound was transferred into 96-well tissue culture plates using a Biomek FX. Each compound was assayed in duplicate for each donor. Each plate contained a dilution series of the TLR7/8 agonist resiquimod as standard and Column 11 contained 1 µl of 200 µM resiquimod (giving a 2 µM final concentration, used to define the approximate maximal response to resiquimod).

Preparation of PBMCs

Blood samples from two human donors were collected into sodium heparin (10 U/ml). 25 ml volumes of whole blood were overlaid onto 15 mls Histopaque in Leucosep tubes which were centrifuged at 800 g for 20 min and the band at the plasma/histopaque interface carefully removed. The collected cells were centrifuged at 2500 rpm for 10 min and the pellet resuspended in 10 ml of media (RPMI 1640 (Low endotoxin) supplemented with 10% v/v foetal calf serum (FCS, low endotoxin) 100 U/ml penicillin G, 100 µg/ml streptomycin, 10 mM L-glutamine and 1× non-essential amino acids). A 1:20 dilution of the cells was prepared using trypan blue & the cells counted using a haemocytometer. The PBMCs were diluted to give a final concentration of $2 \times 10^6$/ml and 100 ul of this cells suspension was added to wells containing 1 µl of diluted test compound.

Incubation and Assays for Interferon-α and TNF-α

The cell preparations were incubated for 24 hr ($37°$ C., 95% air, 5% $CO_2$) after which a sample of the supernatant was removed using the Biomek FX and assayed for both IFN-α and TNF-α using the MSD (Mesoscale Discovery) electrochemiluminescence assay platform. The IFN-α assay was carried out similarly to that described above. The TNF-α assay was carried out as per kit instructions (Cat No K111BHB). Cytokine released was expressed as a percentage of the 2 µM resiquimod control (column 11). This percentage was plotted against compound concentration and the pEC50 for the response determined by non-linear least squares curve fitting. For the IFN-α responses generally a 4 parameter logistic model was selected. For the TNF responses where a clear maximum response was obtained (i.e. a well defined plateau in the response was observed) then a 4 parameter model was generally used. If the upper asymptote of the curve wasn't well defined then the curve fitting was generally constrained to a maximal response of 100% (i.e. to the response to 2 µM resiquimod) or to the response of the highest concentration tested if this was greater than the resiquimod response. Some curves were bell shaped for one or both cytokines and the cytokine data on the down slope of the bell shaped response (i.e. concentrations above those giving the maximal response) were generally excluded from the fit, usually with the exception of the concentration immediately above the peak response. Curve fitting thus concentrated on the up slope of the dose response curve.

Results

Examples 5 and 9 showed mean $pEC_{50}$s for induction of IFN-α and TNF-α of >7.5 and <5.5 respectively. Examples 6, 7, 10 to 12, 14, and 18 showed mean $pEC_{50}$s for induction of IFN-α and TNF-α of ≥8 and <6 respectively. Examples 13, 15 and 20 to 23 showed mean $pEC_{50}$s for induction of IFN-α and TNF-α of ≥9 and ≤6 respectively.

Allergen-driven Cytokine Assay using Fresh Human Peripheral Blood Mononuclear Cells (PBMCs) from Atopic Volunteers An assay based on co-culture of atopic human donor derived peripheral blood mononuclear cells (PBMCs) with allergen and test compounds was developed. After 5-6 days culture, cell supernatants were assayed for a range of cytokines.

Compound Preparation

Compounds were dissolved in DMSO, then serially diluted in growth medium (RPM! 1640 medium supplemented with 100 U/ml penicillin G, 100 µg/ml streptomycin, 10 mM L-glutamine) to give 4× the required concentration range in the presence of 0.04% DMSO. Each compound was assayed in triplicate at all concentrations.

Preparation of PBMCs

Defibrinated human blood from volunteers known to be allergic to Timothy grass was centrifuged at 2500 rpm for 15 minutes. The upper layer of serum was collected and heat-inactivated at 56° C. for 30 minutes (HI-autologous serum). The lower layer of cells was resuspended in 50 ml PBS (+Ca +Mg), 25 ml diluted blood were overlaid onto 20 ml Lymphoprep in 50 ml tubes then centrifuged at 2500 rpm for 20 minutes at RT. The band at the serum/Lymphoprep interface was carefully removed. The collected cells were washed with PBS and re-suspended at $4 \times 10^6$/ml in growth medium with HI-autologous serum. PBMCs were seeded at $0.4 \times 10^6$ cells/well in flat-bottomed 96 well plates in the presence of 10 ug/ml Timothy Grass antigen (Alk Abello) and test compounds at appropriate concentrations in a total volume of 200 ul.

Incubation and Cytokine Assays

Plates were incubated at 37° C. in 5% $CO_2$ for up to 6 days. The cell medium from each well was harvested and stored at −20° C. prior to analysis. Cytokines and chemokines in supernatants were detected using Meso Scale Discovery 10 spot plates for Human TH1/Th2 cytokines.

In the above assay, data from separate studies with PBMCs from three allergic donors showed Example 22 to reduce production of the Th2 cytokines IL-5 and IL-13 in a dose response manner with ≥50% reduction observed at 0.04 µM compared to the allergen control.

Examples 21 and 22 of the invention were also tested for in vivo biological activity in the following model:

Assay for the Induction of Interferon-α Following Intranasal Dosing in the Mouse.

Compounds were dissolved in 0.2% Tween 80 in saline and administered intranasally (5 µl in total between the nostrils) to female BALB/c mice (n=6) under general anaesthesia. Animals were euthanased 2 hours after dosing and a terminal blood sample was taken and serum levels of Interferon-α measured using an ELISA assay.

In this model Example 21 showed mean serum levels of Interferon-α of 20326 pg/ml and Example 22 showed mean serum levels of Interferon-α of 21029 pg/ml. No Interferon-α was detected in vehicle treated controls.

The invention claimed is:

1. A compound of formula (I):

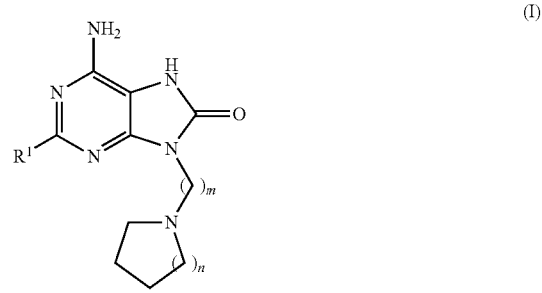

wherein;
$R^1$ is (1S)-1-methylbutyloxy;
m is an integer having a value of 4 to 6;
n is an integer having a value of 2 to 4;
or a salt thereof.

2. A compound or a salt thereof selected from the list consisting of:
6-amino-2-{[(1S)-1-methylbutyl]oxy}-9-[4-(1-piperidinyl)butyl]-7,9-dihydro-8H-purin-8-one;
6-amino-9-[4-(hexahydro-1H-azepin-1-yl)butyl]-2-{[(1S)-1-methylbutyl]oxyl}-7,9-dihydro-8H-purin-8-one, and;
6-amino-9-[5-(hexahydro-1H-azepin-1-yl)pentyl]-2-{[(1S)-1-methylbutyl]oxy}-7,9-dihydro-8H-purin-8-one;
and salts thereof.

3. A salt of a compound of Formula (I) according to claim 1 wherein said salt is a pharmaceutically acceptable salt.

4. A compound of Formual (I) according to claim 1 wherein said compound is a free base.

5. A pharmaceutical composition comprising a compound as defined in claim 1, or a pharmaceutically acceptable salt thereof, and one or more pharmaceutically acceptable diluents or carriers.

6. A combination comprising a compound as defined in claim 1, or a pharmaceutically acceptable salt thereof, together with at least one other therapeutically active agent.

* * * * *